United States Patent
Famili et al.

(10) Patent No.: US 11,891,437 B2
(45) Date of Patent: Feb. 6, 2024

(54) METHODS OF TREATING OCULAR DISORDERS BY ADMINISTERING A VEGF-BINDING ANTIBODY COVALENTLY LINKED TO A HYALURONIC ACID POLYMER

(71) Applicant: Genentech, Inc., South San Francisco, CA (US)

(72) Inventors: Amin Famili, South San Francisco, CA (US); Germaine Fuh, Pacifica, CA (US); Patrick Koenig, San Francisco, CA (US); Chingwei Vivian Lee, Foster City, CA (US); Karthikan Rajagopal, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 15 days.

(21) Appl. No.: 17/392,943

(22) Filed: Aug. 3, 2021

(65) Prior Publication Data
US 2021/0363231 A1 Nov. 25, 2021

Related U.S. Application Data

(60) Division of application No. 16/572,822, filed on Sep. 17, 2019, now Pat. No. 11,111,291, which is a continuation of application No. PCT/US2018/023812, filed on Mar. 22, 2018.

(60) Provisional application No. 62/475,163, filed on Mar. 22, 2017.

(51) Int. Cl.
| | |
|---|---|
| *C07K 16/22* | (2006.01) |
| *A61K 47/61* | (2017.01) |
| *A61K 9/00* | (2006.01) |
| *A61K 9/06* | (2006.01) |
| *A61K 9/08* | (2006.01) |

(52) U.S. Cl.
CPC ............ *C07K 16/22* (2013.01); *A61K 9/0014* (2013.01); *A61K 9/0019* (2013.01); *A61K 9/0048* (2013.01); *A61K 9/06* (2013.01); *A61K 9/08* (2013.01); *A61K 47/61* (2017.08); *C07K 2317/24* (2013.01); *C07K 2317/31* (2013.01); *C07K 2317/55* (2013.01); *C07K 2317/56* (2013.01); *C07K 2317/76* (2013.01); *C07K 2317/92* (2013.01)

(58) Field of Classification Search
CPC ............... C07K 16/22; C07K 2317/24; C07K 2317/55; C07K 2317/56; C07K 2317/76; C07K 2317/92; A61K 9/0048; A61K 9/08; A61K 47/61
See application file for complete search history.

(56) References Cited

U.S. PATENT DOCUMENTS

| | | | |
|---|---|---|---|
| 8,703,130 B2 | 4/2014 | Baehner et al. | |
| 2012/0076787 A1 | 3/2012 | Adamson et al. | |

FOREIGN PATENT DOCUMENTS

| | | |
|---|---|---|
| CN | 1538809 A | 10/2004 |
| JP | 2003-113113 A | 4/2003 |
| JP | 2005-514500 A | 5/2005 |
| JP | 2007-526756 A | 9/2007 |
| JP | 2008-510024 A | 4/2008 |
| KR | 101359142 B1 | 2/2014 |
| KR | 10-2014-0103099 A | 8/2014 |
| WO | WO-02/092131 A2 | 11/2002 |
| WO | WO-02/098232 A1 | 12/2002 |
| WO | WO-03/059973 A2 | 7/2003 |
| WO | WO-2005/012359 A2 | 2/2005 |
| WO | WO-2005/016974 A1 | 2/2005 |
| WO | WO-2005/044853 A2 | 5/2005 |
| WO | WO-2006/016161 A1 | 2/2006 |
| WO | WO-2011/014432 A1 | 2/2011 |
| WO | WO-2011/066417 A2 | 6/2011 |
| WO | WO-2013053856 A1 | 4/2013 |
| WO | WO-2016/008817 A1 | 1/2016 |
| WO | WO-2016/073894 A1 | 5/2016 |
| WO | WO-2017/053807 A2 | 3/2017 |

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983 (doi: 10.1073/pnas.79.6.1979).*
Colman, PM (1994) Research in Immunology, Elsevier, NY, 145(1):33-36.*
Bendig M. M. (1995) Methods: A Companion to Methods in Enzymology, 8:83-93.*
MacCallum et al. (Oct. 11, 1996) J. Mol. Biol., 262(5):732-745. (doi: 10.1006/jmbi.1996.0548).*
Casset et al (2003) Biochemical and Biophysical Research Communications, 307:198-205. (doi:10.1016/S0006-291X(03)01131-8).*
Chen et al. (1995) Embo J., 14(12):2784-2794. (doi: 10.1002/j.1460-2075.1995.tb07278.x).*
Kalam MA (2016) International Journal of Biological Macromolecules. 89:127-136.*
Wallace B, et al. (Mar. 15, 2018) Am J Respir Crit Care Med. 197(6): 776-787.*
Rane SS and Choi P (2005) Chem Mat. 17:926.*
Notice of Reasons for Rejection for Japanese Patent Application No. 2019-551352, dated Apr. 12, 2022 (8 pages).

(Continued)

*Primary Examiner* — Robert S Landsman
(74) *Attorney, Agent, or Firm* — Clark & Elbing LLP; Karen L. Elbing

(57) ABSTRACT

The present invention provides antibody conjugates that include antibodies (e.g., anti-VEGF antibodies) covalently linked to polymers (e.g., hyaluronic acid (HA) polymers), cysteine engineered antibodies, pharmaceutical compositions thereof, and uses thereof, for example for treatment of disorders associated with pathological angiogenesis (e.g., ocular disorders).

22 Claims, 18 Drawing Sheets
Specification includes a Sequence Listing.

(56) References Cited

OTHER PUBLICATIONS

Office Action for Chinese Patent Application No. 201880031184.4, dated Nov. 15, 2022 (8 pages).
Altiok et al., "Multivalent hyaluronic acid bioconjugates improve sFlt-1 activity in vitro," Biomaterials. 93:95-105 (2016).
Altiok et al., "sFlt Multivalent Conjugates Inhibit Angiogenesis and Improve Half-Life In Vivo," PLoS One. 11(6):e0155990 (2016) (14 pages).
Famili et al., "Hyaluronic Acid-Antibody Fragment Bioconjugates for Extended Ocular Pharmacokinetics," Bioconjug Chem. 30(11):2782-9 (2019).
Oh et al., "Anti-Flt1 peptide—hyaluronate conjugate for the treatment of retinal neovascularization and diabetic retinopathy," Biomaterials. 32(11):3115-23 (2011).
Sun et al., "Biological activities of cytokine-neutralizing hyaluronic acid-antibody conjugates," Wound Repair Regen. 18(3):302-10 (2010).
Examination Report for Gulf Cooperation Council Patent Application No. 2018-34998, dated Oct. 21, 2019 (3 pages).
International Preliminary Report on Patentability for International Patent Application No. PCT/US2018/023812, dated Sep. 24, 2019 (7 pages).
International Search Report and Written Opinion for International Patent Application No. PCT/US2018/023812, dated Jun. 21, 2018 (15 pages).
Notification for Vietnamese Patent Application No. 1-2019-05814, dated Nov. 19, 2019 (3 pages).
Notice of Rejection for Iranian Patent Application No. 139850140003005518, dated Aug. 24, 2020 (13 pages).
Office Action for Colombian Patent Application No. NC2019/0011582, dated Dec. 22, 2021 (6 pages).
Brown et al., "Recombinant Production of Hyaluronic Acid," Current Pharmaceutical Biotechnology. 9(4):239-41 (2008).
Notice of Preliminary Rejection for Korean Patent Application No. 10-2019-7027884, dated Sep. 5, 2023 (23 pages).

* cited by examiner

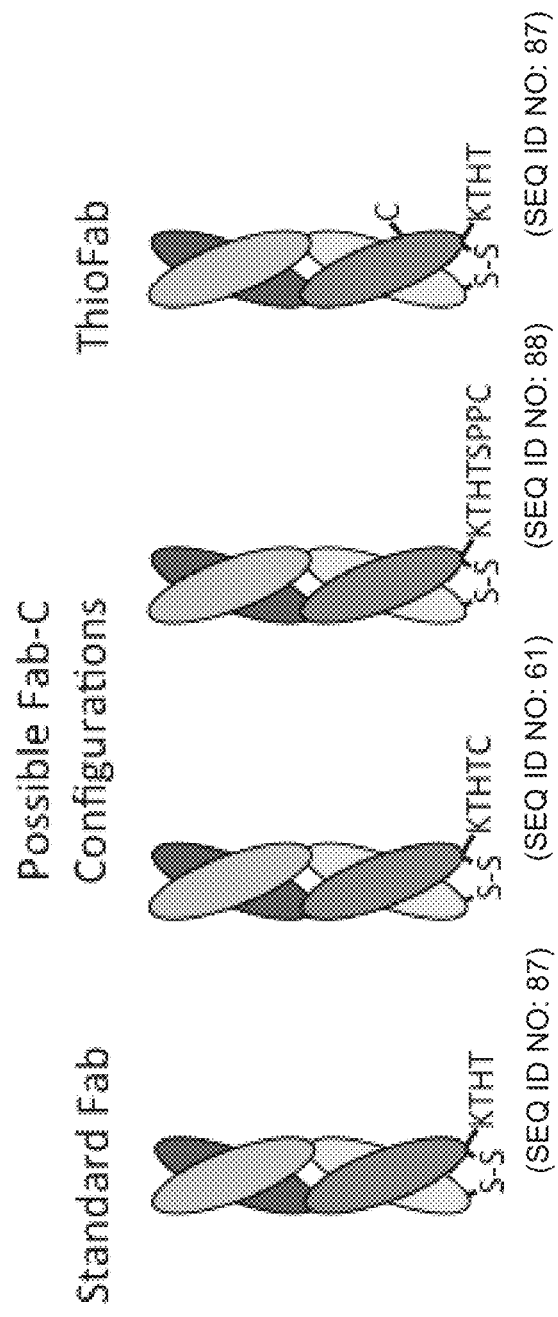

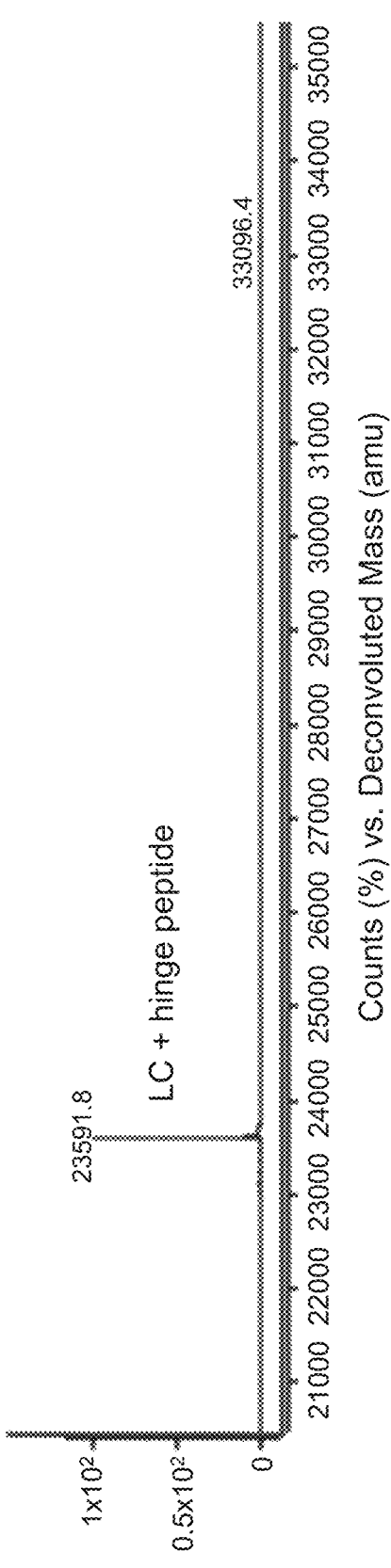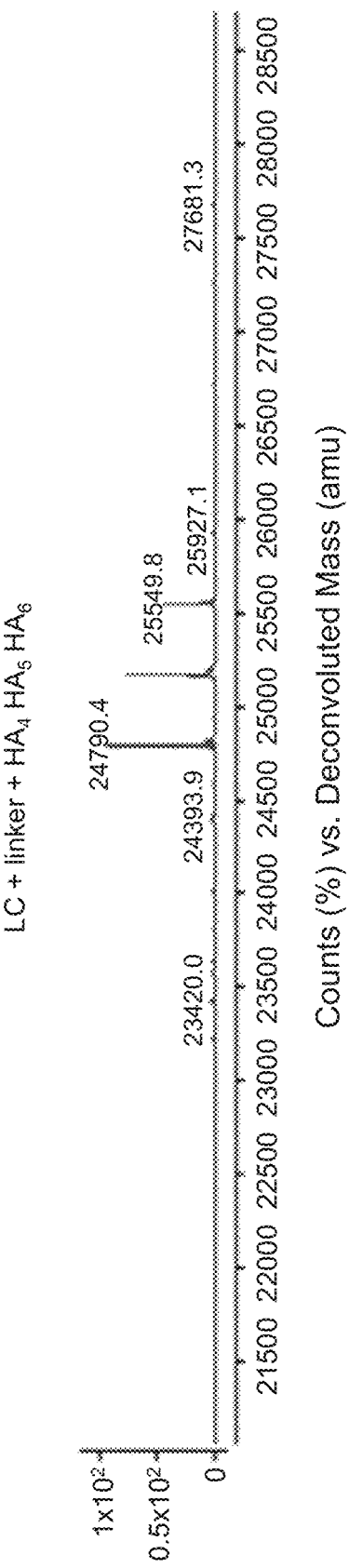
FIG. 10A
FIG. 10B

FIG. 13A

| LC amino acid | GNE Seq. # | LC amino acid | GNE Seq. # | LC amino acid | GNE Seq. # | LC amino acid | GNE Seq. # | LC amino acid | GNE Seq. # |
|---|---|---|---|---|---|---|---|---|---|
| D | 1 | S | 50 | G | 99 | W | 148 | T | 197 |
| I | 2 | A | 51 | Q | 100 | K | 149 | H | 198 |
| Q | 3 | S | 52 | G | 101 | V | 150 | Q | 199 |
| M | 4 | F | 53 | T | 102 | D | 151 | G | 200 |
| T | 5 | L | 54 | K | 103 | N | 152 | L | 201 |
| Q | 6 | Y | 55 | V | 104 | A | 153 | S | 202 |
| S | 7 | S | 56 | E | 105 | L | 154 | S | 203 |
| P | 8 | G | 57 | I | 106 | Q | 155 | P | 204 |
| S | 9 | V | 58 | K | 107 | S | 156 | V | 205 |
| S | 10 | P | 59 | R | 108 | G | 157 | T | 206 |
| L | 11 | S | 60 | T | 109 | N | 158 | K | 207 |
| S | 12 | R | 61 | V | 110 | S | 159 | S | 208 |
| A | 13 | F | 62 | A | 111 | Q | 160 | F | 209 |
| S | 14 | S | 63 | A | 112 | E | 161 | N | 210 |
| V | 15 | G | 64 | P | 113 | S | 162 | R | 211 |
| G | 16 | S | 65 | S | 114 | V | 163 | G | 212 |
| D | 17 | R | 66 | V | 115 | T | 164 | E | 213 |
| R | 18 | S | 67 | F | 116 | E | 165 | C | 214 |
| V | 19 | G | 68 | I | 117 | Q | 166 | K | 190 |
| T | 20 | T | 69 | F | 118 | D | 167 | V | 191 |
| I | 21 | D | 70 | P | 119 | S | 168 | Y | 192 |
| T | 22 | F | 71 | P | 120 | K | 169 | A | 193 |
| C | 23 | T | 72 | S | 121 | D | 170 | C | 194 |
| R | 24 | L | 73 | D | 122 | S | 171 | E | 195 |
| A | 25 | T | 74 | E | 123 | T | 172 | V | 196 |
| S | 26 | I | 75 | Q | 124 | Y | 173 | T | 197 |
| Q | 27 | S | 76 | L | 125 | S | 174 | H | 198 |
| D | 28 | S | 77 | K | 126 | L | 175 | Q | 199 |
| V | 29 | L | 78 | S | 127 | S | 176 | G | 200 |
| N | 30 | Q | 79 | G | 128 | S | 177 | L | 201 |
| T | 31 | P | 80 | T | 129 | T | 178 | S | 202 |
| A | 32 | E | 81 | A | 130 | L | 179 | S | 203 |
| V | 33 | D | 82 | S | 131 | T | 180 | P | 204 |
| A | 34 | F | 83 | V | 132 | L | 181 | V | 205 |
| W | 35 | A | 84 | V | 133 | S | 182 | T | 206 |
| Y | 36 | T | 85 | C | 134 | K | 183 | K | 207 |
| Q | 37 | Y | 86 | L | 135 | A | 184 | S | 208 |
| Q | 38 | Y | 87 | L | 136 | D | 185 | F | 209 |
| K | 39 | C | 88 | N | 137 | Y | 186 | N | 210 |
| P | 40 | Q | 89 | N | 138 | E | 187 | R | 211 |
| G | 41 | Q | 90 | F | 139 | K | 188 | G | 212 |
| K | 42 | H | 91 | Y | 140 | H | 189 | E | 213 |
| A | 43 | Y | 92 | P | 141 | K | 190 | C | 214 |
| P | 44 | T | 93 | R | 142 | V | 191 | | |
| K | 45 | T | 94 | E | 143 | Y | 192 | | |
| L | 46 | P | 95 | A | 144 | A | 193 | | |
| L | 47 | P | 96 | K | 145 | C | 194 | | |
| I | 48 | T | 97 | V | 146 | E | 195 | | |
| Y | 49 | F | 98 | Q | 147 | V | 196 | | |

FIG. 13B

| HC amino acid | GNE Seq # | Kabat Seq # | EU Seq # | HC amino acid | GNE Seq # | Kabat Seq # | EU Seq # | HC amino acid | GNE Seq # | Kabat Seq # | EU Seq # |
|---|---|---|---|---|---|---|---|---|---|---|---|
| E | 1 | 1 |  | T | 54 | 53 | 51 | M | 107 | 100C | 104 |
| V | 2 | 2 |  | N | 55 | 54 | 52 | D | 108 | 101 | 105 |
| Q | 3 | 3 |  | G | 56 | 55 | 53 | Y | 109 | 102 | 106 |
| L | 4 | 4 |  | Y | 57 | 56 | 54 | W | 110 | 103 | 107 |
| V | 5 | 5 | 2 | T | 58 | 57 | 55 | G | 111 | 104 | 108 |
| E | 6 | 6 | 3 | R | 59 | 58 | 56 | Q | 112 | 105 | 109 |
| S | 7 | 7 | 4 | Y | 60 | 59 | 57 | G | 113 | 106 | 110 |
| G | 8 | 8 | 5 | A | 61 | 60 | 58 | T | 114 | 107 | 111 |
| G | 9 | 9 | 6 | D | 62 | 61 | 59 | L | 115 | 108 | 112 |
| G | 10 | 10 | 7 | S | 63 | 62 | 60 | V | 116 | 109 | 113 |
| L | 11 | 11 | 8 | V | 64 | 63 | 61 | T | 117 | 110 | 114 |
| V | 12 | 12 | 9 | K | 65 | 64 | 62 | V | 118 | 111 | 115 |
| Q | 13 | 13 | 10 | G | 66 | 65 | 63 | S | 119 | 112 | 116 |
| P | 14 | 14 | 11 | R | 67 | 66 | 64 | S | 120 | 113 | 117 |
| G | 15 | 15 | 12 | F | 68 | 67 | 65 | A | 121 | 114 | 118 |
| G | 16 | 16 | 13 | T | 69 | 68 | 66 | S | 122 | 115 | 119 |
| S | 17 | 17 | 14 | I | 70 | 69 | 67 | T | 123 | 116 | 120 |
| L | 18 | 18 | 15 | S | 71 | 70 | 68 | K | 124 | 117 | 121 |
| R | 19 | 19 | 16 | A | 72 | 71 | 69 | G | 125 | 118 | 122 |
| L | 20 | 20 | 17 | D | 73 | 72 | 70 | P | 126 | 119 | 123 |
| S | 21 | 21 | 18 | T | 74 | 73 | 71 | S | 127 | 120 | 124 |
| C | 22 | 22 | 19 | S | 75 | 74 | 72 | V | 128 | 121 | 125 |
| A | 23 | 23 | 20 | K | 76 | 75 | 73 | F | 129 | 122 | 126 |
| A | 24 | 24 | 21 | N | 77 | 76 | 74 | P | 130 | 123 | 127 |
| S | 25 | 25 | 22 | T | 78 | 77 | 75 | L | 131 | 124 | 128 |
| G | 26 | 26 | 23 | A | 79 | 78 | 76 | A | 132 | 125 | 129 |
| F | 27 | 27 | 24 | Y | 80 | 79 | 77 | P | 133 | 126 | 130 |
| N | 28 | 28 | 25 | L | 81 | 80 | 78 | S | 134 | 127 | 131 |
| I | 29 | 29 | 26 | Q | 82 | 81 | 79 | S | 135 | 128 | 132 |
| K | 30 | 30 | 27 | M | 83 | 82 | 80 | K | 136 | 129 | 133 |
| D | 31 | 31 | 28 | N | 84 | 82A | 81 | S | 137 | 130 | 134 |
| T | 32 | 32 | 29 | S | 85 | 82B | 82 | T | 138 | 131 | 135 |
| Y | 33 | 33 | 30 | L | 86 | 82C | 83 | S | 139 | 132 | 136 |
| I | 34 | 34 | 31 | R | 87 | 83 | 84 | G | 140 | 133 | 137 |
| H | 35 | 35 | 32 | A | 88 | 84 | 85 | G | 141 | 134 | 138 |
| W | 36 | 36 | 33 | E | 89 | 85 | 86 | T | 142 | 135 | 139 |
| V | 37 | 37 | 34 | D | 90 | 86 | 87 | A | 143 | 136 | 140 |
| R | 38 | 38 | 35 | T | 91 | 87 | 88 | A | 144 | 137 | 141 |
| Q | 39 | 39 | 36 | A | 92 | 88 | 89 | L | 145 | 138 | 142 |
| A | 40 | 40 | 37 | V | 93 | 89 | 90 | G | 146 | 139 | 143 |
| P | 41 | 41 | 38 | Y | 94 | 90 | 91 | C | 147 | 140 | 144 |
| G | 42 | 42 | 39 | Y | 95 | 91 | 92 | L | 148 | 141 | 145 |
| K | 43 | 43 | 40 | C | 96 | 92 | 93 | V | 149 | 142 | 146 |
| G | 44 | 44 | 41 | S | 97 | 93 | 94 | K | 150 | 143 | 147 |
| L | 45 | 45 | 42 | R | 98 | 94 | 95 | D | 151 | 144 | 148 |
| E | 46 | 46 | 43 | W | 99 | 95 | 96 | Y | 152 | 145 | 149 |
| W | 47 | 47 | 44 | G | 100 | 96 | 97 | F | 153 | 146 | 150 |
| V | 48 | 48 | 45 | G | 101 | 97 | 98 | P | 154 | 147 | 151 |
| A | 49 | 49 | 46 | D | 102 | 98 | 99 | E | 155 | 148 | 152 |
| R | 50 | 50 | 47 | G | 103 | 99 | 100 | P | 156 | 149 | 153 |
| I | 51 | 51 | 48 | F | 104 | 100 | 101 | V | 157 | 150 | 154 |
| Y | 52 | 52 | 49 | Y | 105 | 100A | 102 | T | 158 | 151 | 155 |
| P | 53 | 52A | 50 | A | 106 | 100B | 103 | V | 159 | 152 | 156 |

FIG. 13B (continued)

| HC amino acid | GNE Seq.# | Kabat Seq.# | EU Seq. # |
|---|---|---|---|
| S | 160 | 153 | 157 |
| W | 161 | 154 | 158 |
| N | 162 | 155 | 159 |
| S | 163 | 156 | 160 |
| G | 164 | 157 | 161 |
| A | 165 | 158 | 162 |
| L | 166 | 159 | 163 |
| T | 167 | 160 | 164 |
| S | 168 | 161 | 165 |
| G | 169 | 162 | 166 |
| V | 170 | 163 | 167 |
| H | 171 | 164 | 168 |
| T | 172 | 165 | 169 |
| F | 173 | 166 | 170 |
| P | 174 | 167 | 171 |
| A | 175 | 168 | 172 |
| V | 176 | 169 | 173 |
| L | 177 | 170 | 174 |
| Q | 178 | 171 | 175 |
| S | 179 | 172 | 176 |
| S | 180 | 173 | 177 |
| G | 181 | 174 | 178 |
| L | 182 | 175 | 179 |
| Y | 183 | 176 | 180 |
| S | 184 | 177 | 181 |
| L | 185 | 178 | 182 |
| S | 186 | 179 | 183 |
| S | 187 | 180 | 184 |
| V | 188 | 181 | 185 |
| V | 189 | 182 | 186 |
| T | 190 | 183 | 187 |
| V | 191 | 184 | 188 |
| P | 192 | 185 | 189 |
| S | 193 | 186 | 190 |
| S | 194 | 187 | 191 |
| S | 195 | 188 | 192 |
| L | 196 | 189 | 193 |
| G | 197 | 190 | 194 |
| T | 198 | 191 | 195 |
| Q | 199 | 192 | 196 |
| T | 200 | 193 | 197 |
| Y | 201 | 194 | 198 |
| I | 202 | 195 | 199 |
| C | 203 | 196 | 200 |
| N | 204 | 197 | 201 |
| V | 205 | 198 | 202 |
| N | 206 | 199 | 203 |
| H | 207 | 200 | 204 |
| K | 208 | 201 | 205 |
| P | 209 | 202 | 206 |
| S | 210 | 203 | 207 |
| N | 211 | 204 | 208 |
| T | 212 | 205 | 209 |

| HC amino acid | GNE Seq.# | Kabat Seq.# | EU Seq. # |
|---|---|---|---|
| K | 213 | 206 | 210 |
| V | 214 | 207 | 211 |
| D | 215 | 208 | 212 |
| K | 216 | 209 | 213 |
| K | 217 | 210 | 214 |
| V | 218 | 211 | 215 |
| E | 219 | 212 | 216 |
| P | 220 | 213 | 217 |
| K | 221 | 214 | 218 |
| S | 222 | 215 | 219 |
| C | 223 | 216 | 220 |
| D | 224 | 217 | 221 |
| K | 225 | 218 | 222 |
| T | 226 | 219 | 223 |
| H | 227 | 220 | 224 |
| T | 228 | 221 | 225 |
| C | 229 | 222 | 226 |
| P | 230 | 223 | 227 |
| P | 231 | 224 | 228 |
| C | 232 | 225 | 229 |
| P | 233 | 226 | 230 |
| A | 234 | 227 | 231 |
| P | 235 | 228 | 232 |
| E | 236 | 229 | 233 |
| L | 237 | 230 | 234 |
| L | 238 | 231 | 235 |
| G | 239 | 232 | 236 |
| G | 240 | 233 | 237 |
| P | 241 | 234 | 238 |
| S | 242 | 235 | 239 |
| V | 243 | 236 | 240 |
| F | 244 | 237 | 241 |
| L | 245 | 238 | 242 |
| F | 246 | 239 | 243 |
| P | 247 | 240 | 244 |
| P | 248 | 241 | 245 |
| K | 249 | 242 | 246 |
| P | 250 | 243 | 247 |
| K | 251 | 244 | 248 |
| D | 252 | 245 | 249 |
| T | 253 | 246 | 250 |
| L | 254 | 247 | 251 |
| M | 255 | 248 | 252 |
| I | 256 | 249 | 253 |
| S | 257 | 250 | 254 |
| R | 258 | 251 | 255 |
| T | 259 | 252 | 256 |
| P | 260 | 253 | 257 |
| E | 261 | 254 | 258 |
| V | 262 | 255 | 259 |
| T | 263 | 256 | 260 |
| C | 264 | 257 | 261 |
| V | 265 | 258 | 262 |

| HC amino acid | GNE Seq.# | Kabat Seq.# | EU Seq. # |
|---|---|---|---|
| V | 266 | 259 | 263 |
| V | 267 | 260 | 264 |
| D | 268 | 261 | 265 |
| V | 269 | 262 | 266 |
| S | 270 | 263 | 267 |
| H | 271 | 264 | 268 |
| E | 272 | 265 | 269 |
| D | 273 | 266 | 270 |
| P | 274 | 267 | 271 |
| E | 275 | 268 | 272 |
| V | 276 | 269 | 273 |
| K | 277 | 270 | 274 |
| F | 278 | 271 | 275 |
| N | 279 | 272 | 276 |
| W | 280 | 273 | 277 |
| Y | 281 | 274 | 278 |
| V | 282 | 275 | 279 |
| D | 283 | 276 | 280 |
| G | 284 | 277 | 281 |
| V | 285 | 278 | 282 |
| E | 286 | 279 | 283 |
| V | 287 | 280 | 284 |
| H | 288 | 281 | 285 |
| N | 289 | 282 | 286 |
| A | 290 | 283 | 287 |
| K | 291 | 284 | 288 |
| T | 292 | 285 | 289 |
| K | 293 | 286 | 290 |
| P | 294 | 287 | 291 |
| R | 295 | 288 | 292 |
| E | 296 | 289 | 293 |
| E | 297 | 290 | 294 |
| Q | 298 | 291 | 295 |
| Y | 299 | 292 | 296 |
| N | 300 | 293 | 297 |
| S | 301 | 294 | 298 |
| T | 302 | 295 | 299 |
| Y | 303 | 296 | 300 |
| R | 304 | 297 | 301 |
| V | 305 | 298 | 302 |
| V | 306 | 299 | 303 |
| S | 307 | 300 | 304 |
| V | 308 | 301 | 305 |
| L | 309 | 302 | 306 |
| T | 310 | 303 | 307 |
| V | 311 | 304 | 308 |
| L | 312 | 305 | 309 |
| H | 313 | 306 | 310 |
| Q | 314 | 307 | 311 |
| D | 315 | 308 | 312 |
| W | 316 | 309 | 313 |
| L | 317 | 310 | 314 |
| N | 318 | 311 | 315 |

FIG. 13B (continued)

| HC amino acid | GNE Seq. # | Kabat Seq. # | EU Seq. # |
|---|---|---|---|
| G | 319 | 312 | 316 |
| K | 320 | 313 | 317 |
| E | 321 | 314 | 318 |
| Y | 322 | 315 | 319 |
| K | 323 | 316 | 320 |
| C | 324 | 317 | 321 |
| K | 325 | 318 | 322 |
| V | 326 | 319 | 323 |
| S | 327 | 320 | 324 |
| N | 328 | 321 | 325 |
| K | 329 | 322 | 326 |
| A | 330 | 323 | 327 |
| L | 331 | 324 | 328 |
| P | 332 | 325 | 329 |
| A | 333 | 326 | 330 |
| P | 334 | 327 | 331 |
| I | 335 | 328 | 332 |
| E | 336 | 329 | 333 |
| K | 337 | 330 | 334 |
| T | 338 | 331 | 335 |
| I | 339 | 332 | 336 |
| S | 340 | 333 | 337 |
| K | 341 | 334 | 338 |
| A | 342 | 335 | 339 |
| K | 343 | 336 | 340 |
| G | 344 | 337 | 341 |
| Q | 345 | 338 | 342 |
| P | 346 | 339 | 343 |
| R | 347 | 340 | 344 |
| E | 348 | 341 | 345 |
| P | 349 | 342 | 346 |
| Q | 350 | 343 | 347 |
| V | 351 | 344 | 348 |
| Y | 352 | 345 | 349 |
| T | 353 | 346 | 350 |
| L | 354 | 347 | 351 |
| P | 355 | 348 | 352 |
| P | 356 | 349 | 353 |
| S | 357 | 350 | 354 |
| R | 358 | 351 | 355 |
| D | 359 | 352 | 356 |
| E | 360 | 353 | 357 |
| L | 361 | 354 | 358 |
| T | 362 | 355 | 359 |
| K | 363 | 356 | 360 |
| N | 364 | 357 | 361 |
| Q | 365 | 358 | 362 |
| V | 366 | 359 | 363 |
| S | 367 | 360 | 364 |
| L | 368 | 361 | 365 |
| T | 369 | 362 | 366 |
| C | 370 | 363 | 367 |
| L | 371 | 364 | 368 |

| HC amino acid | GNE Seq. # | Kabat Seq. # | EU Seq. # |
|---|---|---|---|
| V | 372 | 365 | 369 |
| K | 373 | 366 | 370 |
| G | 374 | 367 | 371 |
| F | 375 | 368 | 372 |
| Y | 376 | 369 | 373 |
| P | 377 | 370 | 374 |
| S | 378 | 371 | 375 |
| D | 379 | 372 | 376 |
| I | 380 | 373 | 377 |
| A | 381 | 374 | 378 |
| V | 382 | 375 | 379 |
| E | 383 | 376 | 380 |
| W | 384 | 377 | 381 |
| E | 385 | 378 | 382 |
| S | 386 | 379 | 383 |
| N | 387 | 380 | 384 |
| G | 388 | 381 | 385 |
| Q | 389 | 382 | 386 |
| P | 390 | 383 | 387 |
| E | 391 | 384 | 388 |
| N | 392 | 385 | 389 |
| N | 393 | 386 | 390 |
| Y | 394 | 387 | 391 |
| K | 395 | 388 | 392 |
| T | 396 | 389 | 393 |
| T | 397 | 390 | 394 |
| P | 398 | 391 | 395 |
| P | 399 | 392 | 396 |
| V | 400 | 393 | 397 |
| L | 401 | 394 | 398 |
| D | 402 | 395 | 399 |
| S | 403 | 396 | 400 |
| D | 404 | 397 | 401 |
| G | 405 | 398 | 402 |
| S | 406 | 399 | 403 |
| F | 407 | 400 | 404 |
| F | 408 | 401 | 405 |
| L | 409 | 402 | 406 |
| Y | 410 | 403 | 407 |
| S | 411 | 404 | 408 |
| K | 412 | 405 | 409 |
| L | 413 | 406 | 410 |
| T | 414 | 407 | 411 |
| V | 415 | 408 | 412 |
| D | 416 | 409 | 413 |
| K | 417 | 410 | 414 |
| S | 418 | 411 | 415 |
| R | 419 | 412 | 416 |
| W | 420 | 413 | 417 |
| Q | 421 | 414 | 418 |
| Q | 422 | 415 | 419 |
| G | 423 | 416 | 420 |
| N | 424 | 417 | 421 |

| HC amino acid | GNE Seq. # | Kabat Seq. # | EU Seq. # |
|---|---|---|---|
| V | 425 | 418 | 422 |
| F | 426 | 419 | 423 |
| S | 427 | 420 | 424 |
| C | 428 | 421 | 425 |
| S | 429 | 422 | 426 |
| V | 430 | 423 | 427 |
| M | 431 | 424 | 428 |
| H | 432 | 425 | 429 |
| E | 433 | 426 | 430 |
| A | 434 | 427 | 431 |
| L | 435 | 428 | 432 |
| H | 436 | 429 | 433 |
| N | 437 | 430 | 434 |
| H | 438 | 431 | 435 |
| Y | 439 | 432 | 436 |
| T | 440 | 433 | 437 |
| Q | 441 | 434 | 438 |
| K | 442 | 435 | 439 |
| S | 443 | 436 | 440 |
| L | 444 | 437 | 441 |
| S | 445 | 438 | 442 |
| L | 446 | 439 | 443 |
| S | 447 | 440 | 444 |
| P | 448 | 441 | 445 |
| G | 449 | 442 | 446 |
| K | 450 | 443 | 447 |

SEQUENCE LISTING

```
<160> NUMBER OF SEQ ID NOS: 94

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Asp Tyr Trp Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Ile or His
<220> FEATURE:
<221> NAME/KEY: MISC_FEATURE
<222> LOCATION: (5)..(5)
<223> OTHER INFORMATION: Xaa is Ala or Arg
<220> FEATURE:
<221> NAME/KEY: MISC_FEATURE
<222> LOCATION: (8)..(8)
<223> OTHER INFORMATION: Xaa is Tyr or Lys
<220> FEATURE:
<221> NAME/KEY: MISC_FEATURE
```

```
<222> LOCATION: (9)..(9)
<223> OTHER INFORMATION: Xaa is Thr or Glu
<220> FEATURE:
<221> NAME/KEY: MISC_FEATURE
<222> LOCATION: (10)..(10)
<223> OTHER INFORMATION: Xaa is Arg, Tyr, Gln, or Glu
<220> FEATURE:
<221> NAME/KEY: MISC_FEATURE
<222> LOCATION: (12)..(12)
<223> OTHER INFORMATION: Xaa is Ala or Glu
<220> FEATURE:
<221> NAME/KEY: MISC_FEATURE
<222> LOCATION: (16)..(16)
<223> OTHER INFORMATION: Xaa is Lys or Glu
<220> FEATURE:
<221> NAME/KEY: MISC_FEATURE
<222> LOCATION: (17)..(17)
<223> OTHER INFORMATION: Xaa is Gly or Glu

<400> SEQUENCE: 2

Gly Xaa Thr Pro Xaa Gly Gly Xaa Xaa Xaa Tyr Xaa Asp Ser Val Xaa
1               5                   10                  15

Xaa

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct

<400> SEQUENCE: 3

Phe Val Phe Phe Leu Pro Tyr Ala Met Asp Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Asp or Arg

<400> SEQUENCE: 4

Arg Ala Ser Gln Xaa Val Ser Thr Ala Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Ser or Met

<400> SEQUENCE: 5

Xaa Ala Ser Phe Leu Tyr Ser
1               5

<210> SEQ ID NO 6
<211> LENGTH: 9
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Gln, Asn, or Thr
<220> FEATURE:
<221> NAME/KEY: MISC_FEATURE
<222> LOCATION: (6)..(6)
<223> OTHER INFORMATION: Xaa is Ala, Asn, Gln, or Arg

<400> SEQUENCE: 6

Xaa Gln Gly Tyr Gly Xaa Pro Phe Thr
1               5

<210> SEQ ID NO 7
<211> LENGTH: 17
<212> TYPE: PRT
<213> ORGANISM: Artificial Sequence
<220> FEATURE:
<223> OTHER INFORMATION: Synthetic Construct

<400> SEQUENCE: 7

Gly Ile Thr Pro Ala Gly Gly Tyr Thr Arg Tyr Ala Asp Ser Val Lys
1               5                   10                  15

Gly

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Arg Ala Ser Gln Asp Val Ser Thr Ala Val Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Ser Ala Ser Phe Leu Tyr Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Gln Gln Gly Tyr Gly Ala Pro Phe Thr
1               5

<210> SEQ ID NO 11
<211> LENGTH: 120
<212> TYPE: PRT
<213> ORGANISM: Artificial Sequence
<220> FEATURE:
<223> OTHER INFORMATION: Synthetic Construct

<400> SEQUENCE: 11
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
            35                  40                  45

Ala Gly Ile Thr Pro Ala Gly Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Arg Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser
        115                 120

<210> SEQ ID NO 12
<211> LENGTH: 107
<212> TYPE: PRT
<213> ORGANISM: Artificial Sequence
<220> FEATURE:
<223> OTHER INFORMATION: Synthetic Construct

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Gln Tyr Gly Ala Pro Phe
                85                  90                  95

Thr Phe Gly Gln Gly Thr Lys Val Glu Ile Lys
            100                 105

<210> SEQ ID NO 13
<211> LENGTH: 30
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser
            20                  25                  30

<210> SEQ ID NO 14
<211> LENGTH: 14
<212> TYPE: PRT
<213> ORGANISM: Artificial Sequence
<220> FEATURE:
<223> OTHER INFORMATION: Synthetic Construct
```

```
<400> SEQUENCE: 14

Trp Val Arg Gln Ala Pro Gly Lys Gly Leu Glu Trp Val Ala
1               5                   10

<210> SEQ ID NO 15
<211> LENGTH: 32
<212> TYPE: PRT
<213> ORGANISM: Artificial Sequence
<220> FEATURE:
<223> OTHER INFORMATION: Synthetic Construct

<400> SEQUENCE: 15

Arg Phe Thr Ile Ser Ala Asp Thr Ser Lys Asn Thr Ala Tyr Leu Gln
1               5                   10                  15

Met Arg Ser Leu Arg Ala Glu Asp Thr Ala Val Tyr Tyr Cys Ala Arg
            20                  25                  30

<210> SEQ ID NO 16
<211> LENGTH: 11
<212> TYPE: PRT
<213> ORGANISM: Artificial Sequence
<220> FEATURE:
<223> OTHER INFORMATION: Synthetic Construct

<400> SEQUENCE: 16

Trp Gly Gln Gly Thr Leu Val Thr Val Ser Ser
1               5                   10

<210> SEQ ID NO 17
<211> LENGTH: 23
<212> TYPE: PRT
<213> ORGANISM: Artificial Sequence
<220> FEATURE:
<223> OTHER INFORMATION: Synthetic Construct

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 18
<211> LENGTH: 15
<212> TYPE: PRT
<213> ORGANISM: Artificial Sequence
<220> FEATURE:
<223> OTHER INFORMATION: Synthetic Construct

<400> SEQUENCE: 18

Trp Tyr Gln Gln Lys Pro Gly Lys Ala Pro Lys Leu Leu Ile Tyr
1               5                   10                  15

<210> SEQ ID NO 19
<211> LENGTH: 32
<212> TYPE: PRT
<213> ORGANISM: Artificial Sequence
<220> FEATURE:
<223> OTHER INFORMATION: Synthetic Construct

<400> SEQUENCE: 19

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Ala Ala Thr Tyr Tyr Cys
            20                  25                  30
```

```
<210> SEQ ID NO 20
<211> LENGTH: 10
<212> TYPE: PRT
<213> ORGANISM: Artificial Sequence
<220> FEATURE:
<223> OTHER INFORMATION: Synthetic Construct

<400> SEQUENCE: 20

Phe Gly Gln Gly Thr Lys Val Glu Ile Lys
1               5                   10

<210> SEQ ID NO 21
<211> LENGTH: 17
<212> TYPE: PRT
<213> ORGANISM: Artificial Sequence
<220> FEATURE:
<223> OTHER INFORMATION: Synthetic Construct

<400> SEQUENCE: 21

Gly Ile Thr Pro Ala Gly Gly Tyr Glu Tyr Tyr Ala Asp Ser Val Lys
1               5                   10                  15

Gly

<210> SEQ ID NO 22
<211> LENGTH: 17
<212> TYPE: PRT
<213> ORGANISM: Artificial Sequence
<220> FEATURE:
<223> OTHER INFORMATION: Synthetic Construct

<400> SEQUENCE: 22

Gly Ile Thr Pro Ala Gly Gly Tyr Glu Tyr Tyr Ala Asp Ser Val Glu
1               5                   10                  15

Gly

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct

<400> SEQUENCE: 23

Gln Gln Gly Tyr Gly Asn Pro Phe Thr
1               5

<210> SEQ ID NO 24
<211> LENGTH: 32
<212> TYPE: PRT
<213> ORGANISM: Artificial Sequence
<220> FEATURE:
<223> OTHER INFORMATION: Synthetic Construct

<400> SEQUENCE: 24

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
                20                  25                  30

<210> SEQ ID NO 25
<211> LENGTH: 23
<212> TYPE: PRT
<213> ORGANISM: Artificial Sequence
<220> FEATURE:
<223> OTHER INFORMATION: Synthetic Construct
```

```
<400> SEQUENCE: 25

Asp Ile Gln Met Thr Gln Ser Pro Glu Ser Leu Ser Ala Ser Val Gly
1               5                   10                  15

Asp Glu Val Thr Ile Thr Cys
            20

<210> SEQ ID NO 26
<211> LENGTH: 23
<212> TYPE: PRT
<213> ORGANISM: Artificial Sequence
<220> FEATURE:
<223> OTHER INFORMATION: Synthetic Construct

<400> SEQUENCE: 26

Asp Ile Gln Met Thr Gln Ser Pro Ser Ser Leu Ser Ala Ser Val Gly
1               5                   10                  15

Asp Glu Val Thr Ile Thr Cys
            20

<210> SEQ ID NO 27
<211> LENGTH: 15
<212> TYPE: PRT
<213> ORGANISM: Artificial Sequence
<220> FEATURE:
<223> OTHER INFORMATION: Synthetic Construct

<400> SEQUENCE: 27

Trp Tyr Gln Gln Lys Pro Gly Glu Ala Pro Lys Leu Leu Ile Tyr
1               5                   10                  15

<210> SEQ ID NO 28
<211> LENGTH: 32
<212> TYPE: PRT
<213> ORGANISM: Artificial Sequence
<220> FEATURE:
<223> OTHER INFORMATION: Synthetic Construct

<400> SEQUENCE: 28

Gly Val Pro Ser Arg Phe Ser Gly Ser Gly Ser Gly Thr Asp Phe Thr
1               5                   10                  15

Leu Thr Ile Glu Ser Leu Gln Pro Glu Asp Ala Ala Thr Tyr Tyr Cys
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Synthetic Construct

<400> SEQUENCE: 29

Glu Glu Gln Leu Val Glu Gly Gly Gly Leu Val Gln Pro Gly Glu
1               5                   10                  15

Ser Leu Glu Leu Ser Cys Ala Ala Ser Gly Phe Glu Ile Ser
            20                  25                  30

<210> SEQ ID NO 30
<211> LENGTH: 14
<212> TYPE: PRT
<213> ORGANISM: Artificial Sequence
<220> FEATURE:
<223> OTHER INFORMATION: Synthetic Construct

<400> SEQUENCE: 30
```

```
Trp Val Arg Gln Glu Pro Gly Glu Gly Leu Glu Trp Val Ala
1               5                   10
```

```
<210> SEQ ID NO 31
<211> LENGTH: 32
<212> TYPE: PRT
<213> ORGANISM: Artificial Sequence
<220> FEATURE:
<223> OTHER INFORMATION: Synthetic Construct

<400> SEQUENCE: 31

Arg Phe Thr Ile Ser Ala Asp Thr Ser Glu Asn Thr Ala Tyr Leu Gln
1               5                   10                  15

Met Asn Glu Leu Arg Ala Glu Asp Thr Ala Val Tyr Tyr Cys Ala Arg
                20                  25                  30
```

```
<210> SEQ ID NO 32
<211> LENGTH: 11
<212> TYPE: PRT
<213> ORGANISM: Artificial Sequence
<220> FEATURE:
<223> OTHER INFORMATION: Synthetic Construct

<400> SEQUENCE: 32

Trp Gly Gln Gly Glu Leu Val Thr Val Ser Ser
1               5                   10
```

```
<210> SEQ ID NO 33
<211> LENGTH: 120
<212> TYPE: PRT
<213> ORGANISM: Artificial Sequence
<220> FEATURE:
<223> OTHER INFORMATION: Synthetic Construct

<400> SEQUENCE: 33

Glu Glu Gln Leu Val Glu Gly Gly Gly Leu Val Gln Pro Gly Glu
1               5                   10                  15

Ser Leu Glu Leu Ser Cys Ala Ala Ser Gly Phe Glu Ile Ser Asp Tyr
                20                  25                  30

Trp Ile His Trp Val Arg Gln Glu Pro Gly Glu Gly Leu Glu Trp Val
            35                  40                  45

Ala Gly Ile Thr Pro Ala Gly Gly Tyr Glu Tyr Tyr Ala Asp Ser Val
        50                  55                  60

Glu Gly Arg Phe Thr Ile Ser Ala Asp Thr Ser Glu Asn Thr Ala Tyr
65                  70                  75                  80

Leu Gln Met Asn Glu Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
                100                 105                 110

Gly Glu Leu Val Thr Val Ser Ser
        115                 120
```

```
<210> SEQ ID NO 34
<211> LENGTH: 107
<212> TYPE: PRT
<213> ORGANISM: Artificial Sequence
<220> FEATURE:
<223> OTHER INFORMATION: Synthetic Construct

<400> SEQUENCE: 34

Asp Ile Gln Met Thr Gln Ser Pro Glu Ser Leu Ser Ala Ser Val Gly
1               5                   10                  15
```

```
Asp Glu Val Thr Ile Thr Cys Arg Ala Ser Gln Asp Val Ser Thr Ala
             20                  25                  30

Val Ala Trp Tyr Gln Gln Lys Pro Gly Lys Ala Pro Lys Leu Leu Ile
         35                  40                  45

Tyr Ser Ala Ser Phe Leu Tyr Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Ala Ala Thr Tyr Tyr Cys Gln Gln Gly Tyr Gly Ala Pro Phe
                 85                  90                  95

Thr Phe Gly Gln Gly Thr Lys Val Glu Ile Lys
            100                 105

<210> SEQ ID NO 35
<211> LENGTH: 107
<212> TYPE: PRT
<213> ORGANISM: Artificial Sequence
<220> FEATURE:
<223> OTHER INFORMATION: Synthetic Construct

<400> SEQUENCE: 35

Asp Ile Gln Met Thr Gln Ser Pro Ser Ser Leu Ser Ala Ser Val Gly
 1               5                  10                  15

Asp Glu Val Thr Ile Thr Cys Arg Ala Ser Gln Asp Val Ser Thr Ala
             20                  25                  30

Val Ala Trp Tyr Gln Gln Lys Pro Gly Glu Ala Pro Lys Leu Leu Ile
         35                  40                  45

Tyr Ser Ala Ser Phe Leu Tyr Ser Gly Val Pro Ser Arg Phe Ser Gly
     50                  55                  60

Ser Gly Ser Gly Thr Asp Phe Thr Leu Thr Ile Glu Ser Leu Gln Pro
 65                  70                  75                  80

Glu Asp Ala Ala Thr Tyr Tyr Cys Gln Gln Gly Tyr Gly Ala Pro Phe
                 85                  90                  95

Thr Phe Gly Gln Gly Thr Lys Val Glu Ile Lys
            100                 105

<210> SEQ ID NO 36
<211> LENGTH: 107
<212> TYPE: PRT
<213> ORGANISM: Artificial Sequence
<220> FEATURE:
<223> OTHER INFORMATION: Synthetic Construct

<400> SEQUENCE: 36

Asp Ile Gln Met Thr Gln Ser Pro Glu Ser Leu Ser Ala Ser Val Gly
 1               5                  10                  15

Asp Glu Val Thr Ile Thr Cys Arg Ala Ser Gln Asp Val Ser Thr Ala
             20                  25                  30

Val Ala Trp Tyr Gln Gln Lys Pro Gly Glu Ala Pro Lys Leu Leu Ile
         35                  40                  45

Tyr Ser Ala Ser Phe Leu Tyr Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Ala Ala Thr Tyr Tyr Cys Gln Gln Gly Tyr Gly Ala Pro Phe
                 85                  90                  95

Thr Phe Gly Gln Gly Thr Lys Val Glu Ile Lys
```

<210> SEQ ID NO 37
<211> LENGTH: 107
<212> TYPE: PRT
<213> ORGANISM: Artificial Sequence
<220> FEATURE:
<223> OTHER INFORMATION: Synthetic Construct

<400> SEQUENCE: 37

Asp Ile Gln Met Thr Gln Ser Pro Ser Ser Leu Ser Ala Ser Val Gly
1               5                   10                  15

Asp Glu Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Gln Gly Tyr Gly Ala Pro Phe
                85                  90                  95

Thr Phe Gly Gln Gly Thr Lys Val Glu Ile Lys
            100                 105

<210> SEQ ID NO 38
<211> LENGTH: 107
<212> TYPE: PRT
<213> ORGANISM: Artificial Sequence
<220> FEATURE:
<223> OTHER INFORMATION: Synthetic Construct

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Gly Asn Pro Phe
                85                  90                  95

Thr Phe Gly Gln Gly Thr Lys Val Glu Ile Lys
            100                 105

<210> SEQ ID NO 39
<211> LENGTH: 14
<212> TYPE: PRT
<213> ORGANISM: Artificial Sequence
<220> FEATURE:
<223> OTHER INFORMATION: Synthetic Construct

<400> SEQUENCE: 39

Trp Val Arg Gln Glu Pro Gly Lys Gly Leu Glu Trp Val Ala
1               5                   10

<210> SEQ ID NO 40

```
<211> LENGTH: 120
<212> TYPE: PRT
<213> ORGANISM: Artificial Sequence
<220> FEATURE:
<223> OTHER INFORMATION: Synthetic Construct

<400> SEQUENCE: 40

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Glu Pro Gly Lys Gly Leu Glu Trp Val
        35                  40                  45

Ala Gly Ile Thr Pro Ala Gly Gly Tyr Glu Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser
        115                 120

<210> SEQ ID NO 41
<211> LENGTH: 107
<212> TYPE: PRT
<213> ORGANISM: Artificial Sequence
<220> FEATURE:
<223> OTHER INFORMATION: Synthetic Construct

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Gly Ala Pro Phe
                85                  90                  95

Thr Phe Gly Gln Gly Thr Lys Val Glu Ile Lys
            100                 105

<210> SEQ ID NO 42
<211> LENGTH: 120
<212> TYPE: PRT
<213> ORGANISM: Artificial Sequence
<220> FEATURE:
<223> OTHER INFORMATION: Synthetic Construct

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30
```

Trp Ile His Trp Val Arg Gln Ala Pro Gly Lys Gly Leu Glu Trp Val
            35                  40                  45

Ala Gly Ile Thr Pro Ala Gly Gly Tyr Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser
            115                 120

<210> SEQ ID NO 43
<211> LENGTH: 227
<212> TYPE: PRT
<213> ORGANISM: Artificial Sequence
<220> FEATURE:
<223> OTHER INFORMATION: Synthetic Construct

<400> SEQUENCE: 43

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
            35                  40                  45

Ala Gly Ile Thr Pro Ala Gly Gly Tyr Thr Tyr Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
            210                 215                 220

Lys Thr His
225

<210> SEQ ID NO 44
<211> LENGTH: 32
<212> TYPE: PRT
<213> ORGANISM: Artificial Sequence
<220> FEATURE:

```
<223> OTHER INFORMATION: Synthetic Construct

<400> SEQUENCE: 44

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Ser Ala Thr Tyr Tyr Cys
            20                  25                  30

<210> SEQ ID NO 45
<211> LENGTH: 23
<212> TYPE: PRT
<213> ORGANISM: Artificial Sequence
<220> FEATURE:
<223> OTHER INFORMATION: Synthetic Construct

<400> SEQUENCE: 45

Asp Ile Gln Met Thr Gln Ser Pro Ser Ser Leu Ser Ala Ser Val Gly
1               5                   10                  15

Asp Arg Val Thr Ile Asp Cys
            20

<210> SEQ ID NO 46
<211> LENGTH: 107
<212> TYPE: PRT
<213> ORGANISM: Artificial Sequence
<220> FEATURE:
<223> OTHER INFORMATION: Synthetic Construct

<400> SEQUENCE: 46

Asp Ile Gln Met Thr Gln Ser Pro Ser Ser Leu Ser Ala Ser Val Gly
1               5                   10                  15

Asp Arg Val Thr Ile Asp Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Gln Gly Tyr Gly Ala Pro Phe
                85                  90                  95

Thr Phe Gly Gln Gly Thr Lys Val Glu Ile Lys
            100                 105

<210> SEQ ID NO 47
<211> LENGTH: 232
<212> TYPE: PRT
<213> ORGANISM: Homo sapiens

<400> SEQUENCE: 47

Met Asn Phe Leu Leu Ser Trp Val His Trp Ser Leu Ala Leu Leu Leu
1               5                   10                  15

Tyr Leu His His Ala Lys Trp Ser Gln Ala Ala Pro Met Ala Glu Gly
            20                  25                  30

Gly Gly Gln Asn His His Glu Val Val Lys Phe Met Asp Val Tyr Gln
        35                  40                  45

Arg Ser Tyr Cys His Pro Ile Glu Thr Leu Val Asp Ile Phe Gln Glu
    50                  55                  60

Tyr Pro Asp Glu Ile Glu Tyr Ile Phe Lys Pro Ser Cys Val Pro Leu
65                  70                  75                  80
```

```
Met Arg Cys Gly Gly Cys Cys Asn Asp Glu Gly Leu Glu Cys Val Pro
                85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
                180                 185                 190

His Leu Phe Val Gln Asp Pro Gln Thr Cys Lys Cys Ser Cys Lys Asn
            195                 200                 205

Thr Asp Ser Arg Cys Lys Ala Arg Gln Leu Glu Leu Asn Glu Arg Thr
                210                 215                 220

Cys Arg Cys Asp Lys Pro Arg Arg
225                 230

<210> SEQ ID NO 48
<211> LENGTH: 228
<212> TYPE: PRT
<213> ORGANISM: Artificial Sequence
<220> FEATURE:
<223> OTHER INFORMATION: Synthetic Construct

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
                20                  25                  30

Trp Ile His Trp Val Arg Gln Ala Pro Gly Lys Gly Leu Glu Trp Val
            35                  40                  45

Ala Gly Ile Thr Pro Ala Gly Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Arg Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
                195                 200                 205
```

```
Pro Ser Asn Thr Lys Val Asp Lys Lys Val Glu Pro Lys Ser Cys Asp
    210                 215                 220

Lys Thr His Thr
225

<210> SEQ ID NO 49
<211> LENGTH: 228
<212> TYPE: PRT
<213> ORGANISM: Artificial Sequence
<220> FEATURE:
<223> OTHER INFORMATION: Synthetic Construct

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45

Ala Gly Ile Thr Pro Ala Gly Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Arg Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Leu
225

<210> SEQ ID NO 50
<211> LENGTH: 214
<212> TYPE: PRT
<213> ORGANISM: Artificial Sequence
<220> FEATURE:
<223> OTHER INFORMATION: Synthetic Construct

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
```

Tyr Ser Ala Ser Phe Leu Tyr Ser Gly Val Pro Ser Arg Phe Ser Gly
                50                  55                  60

Ser Gly Ser Gly Thr Asp Phe Thr Leu Thr Ile Ser Ser Leu Gln Pro
 65                  70                  75                  80

Glu Asp Ala Ala Thr Tyr Tyr Cys Gln Gln Gly Tyr Gly Ala Pro Phe
                 85                  90                  95

Thr Phe Gly Gln Gly Thr Lys Val Glu Ile Lys Arg Thr Val Ala Ala
               100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 51
<211> LENGTH: 120
<212> TYPE: PRT
<213> ORGANISM: Artificial Sequence
<220> FEATURE:
<223> OTHER INFORMATION: Synthetic Construct

<400> SEQUENCE: 51

Glu Glu Gln Leu Val Glu Gly Gly Gly Leu Val Gln Pro Gly Glu
1               5                   10                  15

Ser Leu Arg Leu Ser Cys Ala Ala Ser Gly Phe Glu Ile Ser Asp Tyr
            20                  25                  30

Trp Ile His Trp Val Arg Gln Glu Pro Gly Glu Gly Leu Glu Trp Val
        35                  40                  45

Ala Gly Ile Thr Pro Ala Gly Gly Tyr Glu Tyr Tyr Ala Asp Ser Val
    50                  55                  60

Glu Gly Arg Phe Thr Ile Ser Ala Asp Thr Ser Glu Asn Thr Ala Tyr
65                  70                  75                  80

Leu Gln Met Asn Glu Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Glu Leu Val Thr Val Ser Ser
        115                 120

<210> SEQ ID NO 52
<211> LENGTH: 30
<212> TYPE: PRT
<213> ORGANISM: Artificial Sequence
<220> FEATURE:
<223> OTHER INFORMATION: Synthetic Construct

<400> SEQUENCE: 52

Glu Glu Gln Leu Val Glu Glu Gly Gly Gly Leu Val Gln Pro Gly Glu
1               5                   10                  15

Ser Leu Arg Leu Ser Cys Ala Ala Ser Gly Phe Glu Ile Ser
            20                  25                  30

<210> SEQ ID NO 53
<211> LENGTH: 17
<212> TYPE: PRT
<213> ORGANISM: Artificial Sequence
<220> FEATURE:
<223> OTHER INFORMATION: Synthetic Construct

<400> SEQUENCE: 53

Gly Ile Thr Pro Ala Gly Gly Tyr Thr Tyr Tyr Ala Asp Ser Val Lys
1               5                   10                  15

Gly

<210> SEQ ID NO 54
<211> LENGTH: 32
<212> TYPE: PRT
<213> ORGANISM: Artificial Sequence
<220> FEATURE:
<223> OTHER INFORMATION: Synthetic Construct

<400> SEQUENCE: 54

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 55
<211> LENGTH: 10
<212> TYPE: PRT
<213> ORGANISM: Artificial Sequence
<220> FEATURE:
<223> OTHER INFORMATION: Synthetic Construct

<400> SEQUENCE: 55

Phe Gly Gln Gly Thr Lys Val Glu Val Lys
1               5                   10

<210> SEQ ID NO 56
<211> LENGTH: 34
<212> TYPE: DNA
<213> ORGANISM: Artificial Sequence
<220> FEATURE:
<223> OTHER INFORMATION: Synthetic Construct

<400> SEQUENCE: 56
catcagatgg cgggaagatg aagacagatg gtgc                              34

<210> SEQ ID NO 57
<211> LENGTH: 23
<212> TYPE: DNA
<213> ORGANISM: Artificial Sequence
<220> FEATURE:
<223> OTHER INFORMATION: Synthetic Construct

<400> SEQUENCE: 57
gccatccaga tgacccagtc tcc                                          23

<210> SEQ ID NO 58
<211> LENGTH: 19
<212> TYPE: DNA
<213> ORGANISM: Artificial Sequence

```
<220> FEATURE:
<223> OTHER INFORMATION: Synthetic Construct

<400> SEQUENCE: 58
ggctgcacca tctgtcttc                                                    19

<210> SEQ ID NO 59
<211> LENGTH: 107
<212> TYPE: PRT
<213> ORGANISM: Artificial Sequence
<220> FEATURE:
<223> OTHER INFORMATION: Synthetic Construct

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Tyr Gly Asn Pro Phe
                85                  90                  95

Thr Phe Gly Gln Gly Thr Lys Val Glu Ile Lys
            100                 105

<210> SEQ ID NO 60
<211> LENGTH: 107
<212> TYPE: PRT
<213> ORGANISM: Artificial Sequence
<220> FEATURE:
<223> OTHER INFORMATION: Synthetic Construct

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Tyr Gly Ala Pro Phe
                85                  90                  95

Thr Phe Gly Gln Gly Thr Lys Val Glu Ile Lys
            100                 105

<210> SEQ ID NO 61
<211> LENGTH: 5
<212> TYPE: PRT
<213> ORGANISM: Artificial Sequence
<220> FEATURE:
<223> OTHER INFORMATION: Synthetic Construct

<400> SEQUENCE: 61
```

Lys Thr His Thr Cys
1               5

<210> SEQ ID NO 62
<211> LENGTH: 5
<212> TYPE: PRT
<213> ORGANISM: Artificial Sequence
<220> FEATURE:
<223> OTHER INFORMATION: Synthetic Construct

<400> SEQUENCE: 62

Gly Tyr Tyr Met His
1               5

<210> SEQ ID NO 63
<211> LENGTH: 17
<212> TYPE: PRT
<213> ORGANISM: Artificial Sequence
<220> FEATURE:
<223> OTHER INFORMATION: Synthetic Construct

<400> SEQUENCE: 63

Trp Ile Asn Pro Asn Ser Gly Gly Thr Asn Tyr Ala Gln Lys Phe Gln
1               5                   10                  15

Gly

<210> SEQ ID NO 64
<211> LENGTH: 20
<212> TYPE: PRT
<213> ORGANISM: Artificial Sequence
<220> FEATURE:
<223> OTHER INFORMATION: Synthetic Construct

<400> SEQUENCE: 64

Ser Pro Asn Pro Tyr Tyr Tyr Asp Ser Ser Gly Tyr Tyr Tyr Pro Gly
1               5                   10                  15

Ala Phe Asp Ile
            20

<210> SEQ ID NO 65
<211> LENGTH: 11
<212> TYPE: PRT
<213> ORGANISM: Artificial Sequence
<220> FEATURE:
<223> OTHER INFORMATION: Synthetic Construct

<400> SEQUENCE: 65

Gly Gly Asn Asn Ile Gly Ser Lys Ser Val His
1               5                   10

<210> SEQ ID NO 66
<211> LENGTH: 7
<212> TYPE: PRT
<213> ORGANISM: Artificial Sequence
<220> FEATURE:
<223> OTHER INFORMATION: Synthetic Construct

<400> SEQUENCE: 66

Asp Asp Ser Asp Arg Pro Ser
1               5

<210> SEQ ID NO 67
<211> LENGTH: 11
<212> TYPE: PRT
<213> ORGANISM: Artificial Sequence
<220> FEATURE:

<223> OTHER INFORMATION: Synthetic Construct

<400> SEQUENCE: 67

Gln Val Trp Asp Ser Ser Asp His Trp Val
1               5                   10

<210> SEQ ID NO 68
<211> LENGTH: 129
<212> TYPE: PRT
<213> ORGANISM: Artificial Sequence
<220> FEATURE:
<223> OTHER INFORMATION: Synthetic Construct

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Pro Asn Pro Tyr Tyr Asp Ser Ser Gly Tyr Tyr Tyr
                100                 105                 110

Pro Gly Ala Phe Asp Ile Trp Gly Gln Gly Thr Met Val Thr Val Ser
            115                 120                 125

Ser

<210> SEQ ID NO 69
<211> LENGTH: 110
<212> TYPE: PRT
<213> ORGANISM: Artificial Sequence
<220> FEATURE:
<223> OTHER INFORMATION: Synthetic Construct

<400> SEQUENCE: 69

Ser Tyr Val Leu Thr Gln Pro Pro Ser Val Ser Val Ala Pro Gly Gln
1               5                   10                  15

Thr Ala Arg Ile Thr Cys Gly Gly Asn Asn Ile Gly Ser Lys Ser Val
                20                  25                  30

His Trp Tyr Gln Gln Lys Pro Gly Gln Ala Pro Val Leu Val Val Tyr
            35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Asp His
                85                  90                  95

Trp Val Phe Gly Gly Gly Thr Lys Leu Thr Val Leu Gly Gln
            100                 105                 110

<210> SEQ ID NO 70
<211> LENGTH: 11
<212> TYPE: PRT
<213> ORGANISM: Artificial Sequence

```
<220> FEATURE:
<223> OTHER INFORMATION: Synthetic Construct

<400> SEQUENCE: 70

Gly Thr Lys Val Glu Cys Lys Arg Thr Val Ala
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Synthetic Construct

<400> SEQUENCE: 71

Lys Val Glu Ile Lys Cys Thr Val Ala Ala Pro
1               5                   10

<210> SEQ ID NO 72
<211> LENGTH: 11
<212> TYPE: PRT
<213> ORGANISM: Artificial Sequence
<220> FEATURE:
<223> OTHER INFORMATION: Synthetic Construct

<400> SEQUENCE: 72

Asn Asn Phe Tyr Pro Cys Glu Ala Lys Val Gln
1               5                   10

<210> SEQ ID NO 73
<211> LENGTH: 11
<212> TYPE: PRT
<213> ORGANISM: Artificial Sequence
<220> FEATURE:
<223> OTHER INFORMATION: Synthetic Construct

<400> SEQUENCE: 73

Ala Lys Val Gln Trp Cys Val Asp Asn Ala Leu
1               5                   10

<210> SEQ ID NO 74
<211> LENGTH: 11
<212> TYPE: PRT
<213> ORGANISM: Artificial Sequence
<220> FEATURE:
<223> OTHER INFORMATION: Synthetic Construct

<400> SEQUENCE: 74

Gln Gly Thr Leu Val Cys Val Ser Ser Ala Ser
1               5                   10

<210> SEQ ID NO 75
<211> LENGTH: 11
<212> TYPE: PRT
<213> ORGANISM: Artificial Sequence
<220> FEATURE:
<223> OTHER INFORMATION: Synthetic Construct

<400> SEQUENCE: 75

Thr Ser Gly Gly Thr Cys Ala Leu Gly Cys Leu
1               5                   10

<210> SEQ ID NO 76
<211> LENGTH: 11
<212> TYPE: PRT
<213> ORGANISM: Artificial Sequence
<220> FEATURE:
```

<223> OTHER INFORMATION: Synthetic Construct

<400> SEQUENCE: 76

Thr Phe Pro Ala Val Cys Gln Ser Ser Gly Leu
1               5                   10

<210> SEQ ID NO 77
<211> LENGTH: 11
<212> TYPE: PRT
<213> ORGANISM: Artificial Sequence
<220> FEATURE:
<223> OTHER INFORMATION: Synthetic Construct

<400> SEQUENCE: 77

Leu Gln Ser Ser Gly Cys Tyr Ser Leu Ser Ser
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Synthetic Construct

<400> SEQUENCE: 78

Leu Ser Ser Val Val Cys Val Pro Ser Ser Ser
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Synthetic Construct

<400> SEQUENCE: 79

His Lys Pro Ser Asn Cys Lys Val Asp Lys Lys
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Synthetic Construct

<400> SEQUENCE: 80

Pro Glu Val Thr Cys Cys Val Val Asp Val Ser
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Synthetic Construct

<400> SEQUENCE: 81

Thr Cys Leu Val Lys Cys Phe Tyr Pro Ser Asp
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Synthetic Construct

```
<400> SEQUENCE: 82

Leu Val Lys Gly Phe Cys Pro Ser Asp Ile Ala
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Synthetic Construct

<400> SEQUENCE: 83

Ile Ala Val Glu Trp Cys Ser Asn Gly Gln Pro
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Synthetic Construct

<400> SEQUENCE: 84

Gln Gly Asn Val Phe Cys Cys Ser Val Met His
1               5                   10

<210> SEQ ID NO 85
<211> LENGTH: 11
<212> TYPE: PRT
<213> ORGANISM: Artificial Sequence
<220> FEATURE:
<223> OTHER INFORMATION: Synthetic Construct

<400> SEQUENCE: 85

His Glu Ala Leu His Cys His Tyr Thr Gln Lys
1               5                   10

<210> SEQ ID NO 86
<211> LENGTH: 11
<212> TYPE: PRT
<213> ORGANISM: Artificial Sequence
<220> FEATURE:
<223> OTHER INFORMATION: Synthetic Construct

<400> SEQUENCE: 86

His Asn His Tyr Thr Cys Lys Ser Leu Ser Leu
1               5                   10

<210> SEQ ID NO 87
<211> LENGTH: 4
<212> TYPE: PRT
<213> ORGANISM: Artificial Sequence
<220> FEATURE:
<223> OTHER INFORMATION: Synthetic Construct

<400> SEQUENCE: 87

Lys Thr His Thr
1

<210> SEQ ID NO 88
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 88

Lys Thr His Thr Ser Pro Pro Cys
1               5

<210> SEQ ID NO 89
<211> LENGTH: 214
<212> TYPE: PRT
<213> ORGANISM: Artificial Sequence
<220> FEATURE:
<223> OTHER INFORMATION: Synthetic Construct

<400> SEQUENCE: 89

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ala Ala Thr Tyr Tyr Cys Gln Gln Gly Tyr Gly Ala Pro Phe
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Cys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 90
<211> LENGTH: 228
<212> TYPE: PRT
<213> ORGANISM: Artificial Sequence
<220> FEATURE:
<223> OTHER INFORMATION: Synthetic Construct

<400> SEQUENCE: 90

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45

Ala Gly Ile Thr Pro Ala Gly Gly Tyr Thr Arg Tyr Ala Asp Ser Val
    50                  55                  60
```

```
Lys Gly Arg Phe Thr Ile Ser Ala Asp Thr Ser Lys Asn Thr Ala Tyr
 65                  70                  75                  80

Leu Gln Met Arg Ser Leu Arg Ala Glu Asp Thr Ala Val Tyr Tyr Cys
             85                  90                  95

Ala Arg Phe Val Phe Leu Pro Tyr Ala Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr
225

<210> SEQ ID NO 91
<211> LENGTH: 214
<212> TYPE: PRT
<213> ORGANISM: Artificial Sequence
<220> FEATURE:
<223> OTHER INFORMATION: Synthetic Construct

<400> SEQUENCE: 91

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
             20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Ala Ala Thr Tyr Tyr Cys Gln Gln Gly Tyr Gly Ala Pro Phe
             85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

```
Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 92
<211> LENGTH: 228
<212> TYPE: PRT
<213> ORGANISM: Artificial Sequence
<220> FEATURE:
<223> OTHER INFORMATION: Synthetic Construct

<400> SEQUENCE: 92

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Asp Tyr
            20                  25                  30

Trp Ile His Trp Val Arg Gln Ala Pro Gly Lys Gly Leu Glu Trp Val
        35                  40                  45

Ala Gly Ile Thr Pro Ala Gly Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Arg Ser Leu Arg Ala Glu Asp Thr Ala Val Tyr Tyr Cys
                85                  90                  95

Ala Arg Phe Val Phe Phe Leu Pro Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Cys Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr
225
```

<210> SEQ ID NO 93
<211> LENGTH: 214
<212> TYPE: PRT
<213> ORGANISM: Artificial Sequence
<220> FEATURE:
<223> OTHER INFORMATION: Synthetic Construct

<400> SEQUENCE: 93

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Ala Ala Thr Tyr Tyr Cys Gln Gln Gly Tyr Gly Ala Pro Phe
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 94
<211> LENGTH: 228
<212> TYPE: PRT
<213> ORGANISM: Artificial Sequence
<220> FEATURE:
<223> OTHER INFORMATION: Synthetic Construct

<400> SEQUENCE: 94

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Ile Ser Asp Tyr
             20                  25                  30

Trp Ile His Trp Val Arg Gln Ala Pro Gly Lys Gly Leu Glu Trp Val
         35                  40                  45

Ala Gly Ile Thr Pro Ala Gly Gly Tyr Thr Arg Tyr Ala Asp Ser Val
     50                  55                  60

Lys Gly Arg Phe Thr Ile Ser Ala Asp Thr Ser Lys Asn Thr Ala Tyr
 65                  70                  75                  80

Leu Gln Met Arg Ser Leu Arg Ala Glu Asp Thr Ala Val Tyr Tyr Cys
                 85                  90                  95

Ala Arg Phe Val Phe Phe Leu Pro Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Cys Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205
Pro Ser Asn Thr Lys Val Asp Lys Lys Val Glu Pro Lys Ser Cys Asp
    210                 215                 220
Lys Thr His Thr
225
```

METHODS OF TREATING OCULAR DISORDERS BY ADMINISTERING A VEGF-BINDING ANTIBODY COVALENTLY LINKED TO A HYALURONIC ACID POLYMER

SEQUENCE LISTING

The instant application contains a Sequence Listing which has been submitted electronically in ASCII format and is hereby incorporated by reference in its entirety. Said ASCII copy, created on Aug. 2, 2021, is named 50474-160004_Sequence_Listing_8_2_21_ST25 and is 57,729 bytes in size.

FIELD OF THE INVENTION

The invention relates generally to antibody conjugates, cysteine engineered antibodies, compositions (e.g., pharmaceutical compositions) thereof, and methods of use thereof.

BACKGROUND OF THE INVENTION

Angiogenesis is a tightly-regulated process through which new blood vessels form from pre-existing blood vessels. Although angiogenesis is important during development to ensure adequate blood circulation, many disorders are associated with pathological angiogenesis, such as ocular disorders (e.g., age-related macular degeneration, AMD) and cell proliferative disorders (e.g., cancer). Vascular endothelial growth factor (VEGF) is a clinically-validated driver of angiogenesis, and neutralization of VEGF (e.g., using an anti-VEGF blocking antibody), can be used to treat disorders associated with pathological angiogenesis.

Current approaches for treatment of ocular disorders associated with pathological angiogenesis (e.g., AMD (e.g., wet AMD), diabetic macular edema (DME), diabetic retinopathy (DR), and retinal vein occlusion (RVO)) typically involve intravitreal injection of VEGF antagonists (e.g., the anti-VEGF Fab ranibizumab). Because the site of action of anti-VEGF Fabs is in the back of the eye at the retina, and also because Fabs can have relatively short residence time in the eye, maximum patient benefit from anti-VEGF Fabs is typically obtained by relatively frequent dosings (e.g., every four weeks, Q4W) by intravitreal injection. Long-acting delivery of anti-VEGF antibodies or antibody fragments (e.g., Fabs) for ocular disorders may be desired, at least in part, to decrease dosing frequency, which can improve patient convenience and compliance.

There remains a need for antibody compositions for long-acting delivery for treatment of ocular disorders (e.g., AMD (e.g., wet AMD), diabetic macular edema (DME), diabetic retinopathy (DR), and retinal vein occlusion (RVO)).

SUMMARY OF THE INVENTION

The invention provides antibody conjugates that include monodisperse polymers (e.g., monodisperse hyaluronic acid (HA) polymers) covalently linked to antibodies (e.g., anti-VEGF antibodies), cysteine engineered antibodies that can be used, e.g., in preparing antibody conjugates, compositions that include antibody conjugates (e.g., pharmaceutical compositions), as well as methods of making and using the same, for example, for therapeutic uses.

In one aspect, the invention features an antibody conjugate comprising (i) an antibody and (ii) a hyaluronic acid (HA) polymer covalently attached to the antibody, wherein the HA polymer has a polydispersity index (PDI) of 1.1 or lower. In some embodiments, the HA polymer has a PDI between 1.0 to 1.1. In some embodiments, the HA polymer has a PDI between 1.0 to about 1.05. In some embodiments, the HA polymer has a PDI between about 1.0001 to about 1.05. In some embodiments, the HA polymer has a PDI of about 1.001. In some embodiments, the HA polymer has a molecular weight of about 1 megadalton (MDa) or lower. In some embodiments, the HA polymer has a molecular weight between about 25 kDa and about 500 kDa. In some embodiments, the HA polymer has a molecular weight between about 100 kDa and about 250 kDa. In some embodiments, the HA polymer has a molecular weight between about 150 kDa and about 200 kDa. In some embodiments, the HA polymer is a linear HA polymer. In some embodiments, the antibody conjugate has a hydrodynamic radius between about 10 nm and about 60 nm. In some embodiments, the antibody conjugate has a hydrodynamic radius between about 25 nm and about 35 nm. In some embodiments, the hydrodynamic radius is about 20 nm to about 30 nm.

In some embodiments of the preceding aspect, the antibody conjugate has an ocular half-life that is increased relative to a reference antibody that is not covalently attached to the HA polymer. In some embodiments, the ocular half-life is increased at least about 2-fold relative to the reference antibody. In some embodiments, the ocular half-life is increased at least about 4-fold relative to the reference antibody. In some embodiments, the ocular half-life is a vitreal half-life. In some embodiments, the reference antibody is identical to the antibody of the antibody conjugate.

In some embodiments of the preceding aspect, the antibody specifically binds to a biological molecule selected from the group consisting of vascular endothelial growth factor (VEGF); IL-1β; IL-6; IL-6R; IL-13; IL-13R; PDGF; angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor; ST-2 receptor; and a protein genetically linked to AMD risk. In some embodiments, the VEGF receptor is VEGFR1, VEGFR2, VEGFR3, mbVEGFR, or sVEGFR. In some embodiments, the protein genetically linked to AMD risk is selected from the group consisting of complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC, COL10A1; and TNFRSF10A.

In some embodiments of the preceding aspect, the antibody specifically binds to VEGF. In some embodiments, the antibody comprises the following six hypervariable regions (HVRs): (a) an HVR-H1 comprising the amino acid sequence of DYWIH (SEQ ID NO: 1); (b) an HVR-H2 comprising the amino acid sequence of $GX_1TPX_2$ $GGX_3X_4X_5YX_6DSVX_7X_8$ (SEQ ID NO: 2), wherein $X_1$ is Ile or His, $X_2$ is Ala or Arg, $X_3$ is Tyr or Lys, $X_4$ is Thr or Glu, $X_5$ is Arg, Tyr, Gln, or Glu, $X_6$ is Ala or Glu, $X_7$ is Lys or Glu, and $X_8$ is Gly or Glu; (c) an HVR-H3 comprising the amino acid sequence of FVFFLPYAMDY (SEQ ID NO: 3); (d) an HVR-L1 comprising the amino acid sequence of $RASQX_1VSTAVA$ (SEQ ID NO: 4), wherein $X_1$ is Asp or Arg; (e) an HVR-L2 comprising the amino acid sequence of $X_1ASFLYS$ (SEQ ID NO: 5), wherein $X_1$ is Ser or Met; and (f) an HVR-L3 comprising the amino acid sequence of $X_1QGYGX_2PFT$ (SEQ ID NO: 6), wherein $X_1$ is Gln, Asn, or Thr and $X_2$ is Ala, Asn, Gln, or Arg. In some embodiments, the antibody comprises the following six HVRs: (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7), GITPAGGYEYYADSVKG (SEQ ID NO: 21), or GITPAGGYEYYADSVEG (SEQ ID NO: 22); (c) an HVR-H3 comprising the amino acid sequence of FVF-FLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10) or QQGYGNPFT (SEQ ID NO: 23).

In some embodiments of the above aspect, the antibody comprises the following six HVRs: (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7); (c) an HVR-H3 comprising the amino acid sequence of FVF-FLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some embodiments, the antibody further comprises the following heavy chain variable (VH) domain framework regions (FRs): (a) an FR-H1 comprising the amino acid sequence of EVQLVESGGGLVQPGGSLRLSCAASGFTIS (SEQ ID NO: 13); (b) an FR-H2 comprising the amino acid sequence of WVRQAPGKGLEWVA (SEQ ID NO: 14); (c) an FR-H3 comprising the amino acid sequence of RFTI-SADTSKNTAYLQMRSLRAEDTAVYYCAR (SEQ ID NO: 15); and (d) an FR-H4 comprising the amino acid sequence of WGQGTLVTVSS (SEQ ID NO: 16). In some embodiments, the antibody further comprises the following light chain variable (VL) domain FRs: (a) an FR-L1 comprising the amino acid sequence of DIQMTQSPSSL-SASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPED-AATYYC (SEQ ID NO: 19); and (d) an FR-L4 comprising the amino acid sequence of FGQGTKVEIK (SEQ ID NO: 20).

In some embodiments of the above aspect, the antibody comprises the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVF-FLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGNPFT (SEQ ID NO: 23). In some embodiments, the antibody further comprises the following VL domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDFATYYC (SEQ ID NO: 24); and (d) an FR-L4 comprising the amino acid sequence of FGQGTKVEIK (SEQ ID NO: 20).

In some embodiments of the above aspect, the antibody comprises the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVF-FLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some embodiments, the antibody further comprises the following VL domain FRs: (a) an FR-L1 comprising the amino acid sequence of DIQMTQSPSSLSASVGDRVTITC (SEQ ID NO: 17), DIQMTQSPESLSASVGDEVTITC (SEQ ID NO: 25), or DIQMTQSPSSLSASVGDEVTITC (SEQ ID NO: 26); (b) an FR-L2 comprising the amino acid sequence of WYQQKPGKAPKLLIY (SEQ ID NO: 18) or WYQQKPGEAPKLLIY (SEQ ID NO: 27); (c) an FR-L3 comprising the amino acid sequence of GVPSRFS-GSGSGTDFTLTISSLQPEDAATYYC (SEQ ID NO: 19) or GVPSRFSGSGSGTDFTLTIESLQPEDAATYYC (SEQ ID NO: 28); and (d) an FR-L4 comprising the amino acid sequence of FGQGTKVEIK (SEQ ID NO: 20). In some embodiments, the antibody further comprises the following VH domain FRs: (a) an FR-H1 comprising the amino acid sequence of EEQLVEEGGGLVQPGESLELSCAASGFEIS (SEQ ID NO: 29) or EEQLVEEGGGLVQPGESLRLS-CAASGFEIS (SEQ ID NO: 52); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYY-CAR (SEQ ID NO: 31); and (d) an FR-H4 comprising the amino acid sequence of WGQGELVTVSS (SEQ ID NO: 32).

In some embodiments of the above aspect, the antibody comprises (a) a VH domain comprising an amino acid sequence having at least 95% sequence identity to the amino acid sequence of SEQ ID NO: 11, 40, or 42; (b) a VL domain comprising an amino acid sequence having at least 95% sequence identity to the amino acid sequence of SEQ ID NO: 12, 41, or 46; or (c) a VH domain as in (a) and a VL domain as in (b). In some embodiments, the VH domain further comprises the following FRs: (a) an FR-H1 comprising the amino acid sequence of EVQLVESGG-GLVQPGGSLRLSCAASGFTIS (SEQ ID NO: 13); (b) an FR-H2 comprising the amino acid sequence of WVRQAPGKGLEWVA (SEQ ID NO: 14) or WVRQEPGKGLEWVA (SEQ ID NO: 39); (c) an FR-H3 comprising the amino acid sequence of RFTISADTSKN-TAYLQMRSLRAEDTAVYYCAR (SEQ ID NO: 15); and (d) an FR-H4 comprising the amino acid sequence of WGQGTLVTVSS (SEQ ID NO: 16). In some embodiments, the VH domain comprises the amino acid sequence of SEQ ID NO: 11. In some embodiments, the VL domain further comprises the following FRs: (a) an FR-L1 comprising the amino acid sequence of DIQMTQSPSSLSASVGDRVTITC (SEQ ID NO: 17) or DIQMTQSPSSLSASVGDRVTIDC (SEQ ID NO: 45); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19), GVPSRFSGSGSGTDFTLTISSLQPEDSATYYC (SEQ ID NO: 44), or GVPSRFSGSGSGTDF-TLTISSLQPEDVATYYC (SEQ ID NO: 54); and (d) an FR-L4 comprising the amino acid sequence of FGQGTKVEIK (SEQ ID NO: 20) or FGQGTKVEVK (SEQ ID NO: 55). In some embodiments, the VL domain comprises the amino acid sequence of SEQ ID NO: 12.

In some embodiments of the above aspect, the antibody comprises (a) a VH domain comprising the amino acid sequence of SEQ ID NO: 11 and (b) a VL domain comprising the amino acid sequence of SEQ ID NO: 12.

In some embodiments of the above aspect, the antibody comprises (a) a VH domain comprising the amino acid sequence of SEQ ID NO: 40 and (b) a VL domain comprising the amino acid sequence of SEQ ID NO: 12.

In some embodiments of the above aspect, the antibody comprises (a) a VH domain comprising the amino acid sequence of SEQ ID NO: 42 and (b) a VL domain comprising the amino acid sequence of SEQ ID NO: 12.

In some embodiments of the above aspect, the antibody comprises (a) a VH domain comprising the amino acid sequence of SEQ ID NO: 42 and (b) a VL domain comprising the amino acid sequence of SEQ ID NO: 41.

In some embodiments of the above aspect, the antibody comprises (a) a VH domain comprising an amino acid sequence having at least 95% sequence identity to the amino acid sequence of SEQ ID NO: 33 or 51; (b) a VL domain comprising an amino acid sequence having at least 95% sequence identity to the amino acid sequence of SEQ ID NO: 12, 34, 35, 36, 37, or 38; or (c) a VH domain as in (a) and a VL domain as in (b). In some embodiments, the antibody further comprises the following FRs: (a) an FR-H1 comprising the amino acid sequence of EEQLVEEGG-GLVQPGESLELSCAASGFEIS (SEQ ID NO: 29) or EEQLVEEGGGLVQPGESLRLSCAASGFEIS (SEQ ID NO: 52); (b) an FR-H2 comprising the amino acid sequence of WVRQEPGEGLEWVA (SEQ ID NO: 30); (c) an FR-H3 comprising the amino acid sequence of RFTISADTSEN-TAYLQMNELRAEDTAVYYCAR (SEQ ID NO: 31); and (d) an FR-H4 comprising the amino acid sequence of WGQGELVTVSS (SEQ ID NO: 32). In some embodiments, the VH domain comprises the amino acid sequence of SEQ ID NO: 33. In some embodiments, the VH domain comprises the amino acid sequence of SEQ ID NO: 51. In some embodiments, the antibody further comprises the following FRs: (a) an FR-L1 comprising the amino acid sequence of DIQMTQSPSSLSASVGDRVTITC (SEQ ID NO: 17), DIQMTQSPESLSASVGDEVTITC (SEQ ID NO: 25), or DIQMTQSPSSLSASVGDEVTITC (SEQ ID NO: 26); (b) an FR-L2 comprising the amino acid sequence of WYQQKPGKAPKLLIY (SEQ ID NO: 18) or WYQQKPGEAPKLLIY (SEQ ID NO: 27); (c) an FR-L3 comprising the amino acid sequence of GVPSRFSGSGSGTDFTLTISSLQPEDAATYYC (SEQ ID NO: 19), GVPSRFSGSGSGTDFTLTISSLQPEDFATYYC (SEQ ID NO: 24), or GVPSRFSGSGSGTDFTLTIES-LQPEDAATYYC (SEQ ID NO: 28); and (d) an FR-L4 comprising the amino acid sequence of FGQGTKVEIK (SEQ ID NO: 20). In some embodiments, the VL domain comprises the amino acid sequence of SEQ ID NO: 34. In some embodiments, the VL domain comprises the amino acid sequence of SEQ ID NO: 35. In some embodiments, the VL domain comprises the amino acid sequence of SEQ ID NO: 36. In some embodiments, the VL domain comprises the amino acid sequence of SEQ ID NO: 37. In some embodiments, the VL domain comprises the amino acid sequence of SEQ ID NO: 12. In some embodiments, the VL domain comprises the amino acid sequence of SEQ ID NO: 38.

In some embodiments of the above aspect, the antibody comprises (a) a VH domain comprising the amino acid sequence of SEQ ID NO: 33 and (b) a VL domain comprising the amino acid sequence of SEQ ID NO: 38.

In some embodiments of the above aspect, the antibody comprises (a) a VH domain comprising the amino acid sequence of SEQ ID NO: 33 and (b) a VL domain comprising the amino acid sequence of SEQ ID NO: 34.

In some embodiments of the above aspect, the antibody comprises (a) a VH domain comprising the amino acid sequence of SEQ ID NO: 33 and (b) a VL domain comprising the amino acid sequence of SEQ ID NO: 35.

In some embodiments of the above aspect, the antibody comprises (a) a VH domain comprising the amino acid sequence of SEQ ID NO: 33 and (b) a VL domain comprising the amino acid sequence of SEQ ID NO: 36.

In some embodiments of the above aspect, the antibody comprises (a) a VH domain comprising the amino acid sequence of SEQ ID NO: 33 and (b) a VL domain comprising the amino acid sequence of SEQ ID NO: 37.

In some embodiments of the above aspect, the antibody comprises (a) a VH domain comprising the amino acid sequence of SEQ ID NO: 33 and (b) a VL domain comprising the amino acid sequence of SEQ ID NO: 12.

In some embodiments of the above aspect, the antibody comprises (a) a VH domain comprising the amino acid sequence of SEQ ID NO: 51 and (b) a VL domain comprising the amino acid sequence of SEQ ID NO: 38.

In some embodiments of the above aspect, the antibody comprises (a) a VH domain comprising the amino acid sequence of SEQ ID NO: 51 and (b) a VL domain comprising the amino acid sequence of SEQ ID NO: 35.

In some embodiments of the above aspect, the antibody comprises (a) a VH domain comprising the amino acid sequence of SEQ ID NO: 51 and (b) a VL domain comprising the amino acid sequence of SEQ ID NO: 37.

In some embodiments of the above aspect, the antibody comprises (a) a VH domain comprising the amino acid sequence of SEQ ID NO: 51 and (b) a VL domain comprising the amino acid sequence of SEQ ID NO: 12.

In some embodiments of the above aspect, the antibody comprises (a) a heavy chain comprising the amino acid sequence of SEQ ID NO: 48 and (b) a light chain comprising the amino acid sequence of SEQ ID NO: 50.

In some embodiments of the above aspect, the antibody comprises (a) a heavy chain comprising the amino acid sequence of SEQ ID NO: 49 and (b) a light chain comprising the amino acid sequence of SEQ ID NO: 50.

In some embodiments of any of the preceding aspects, the antibody is capable of inhibiting the binding of VEGF to a VEGF receptor. In some embodiments, the VEGF receptor is VEGF receptor 1 (Flt-1). In some embodiments, the VEGF receptor is VEGF receptor 2 (KDR).

In some embodiments of any of the preceding aspects, the antibody binds human VEGF (hVEGF) with a Kd of about 2 nM or lower. In some embodiments, the antibody binds hVEGF with a Kd between about 75 pM and about 2 nM. In some embodiments, the antibody binds hVEGF with a Kd between about 75 pM and about 600 pM. In some embodiments, the antibody binds hVEGF with a Kd between about 75 pM and about 500 pM. In some embodiments, the antibody binds hVEGF with a Kd of about 80 pM. In some embodiments, the antibody binds hVEGF with a Kd of about 60 pM.

In some embodiments of any of the preceding aspects, the antibody has a melting temperature (Tm) of greater than about 83.5° C. In some embodiments, the antibody has a Tm of about 85° C. to about 91° C. In some embodiments, the antibody has a Tm of about 89° C.

In some embodiments of any of the preceding aspects, the antibody has an isoelectric point (pI) of lower than 8. In some embodiments, the antibody has a pI from about 5 to about 7. In some embodiments, the antibody has a pI of from about 5 to about 6.

In some embodiments of any of the preceding aspects, the antibody is monoclonal, human, humanized, or chimeric.

In some embodiments of any of the preceding aspects, the antibody is an antibody fragment that binds VEGF. In some embodiments, the antibody fragment is selected from the group consisting of Fab, Fab-C, Fab'-SH, Fv, scFv, and (Fab')$_2$ fragments. In some embodiments, the antibody fragment is an Fab.

In some embodiments of any of the preceding aspects, the antibody is a monospecific antibody. In other embodiments of any of the preceding aspects, the antibody is a multispecific antibody. In some embodiments, the multispecific antibody is a bispecific antibody. In some embodiments, the bispecific antibody binds VEGF and a second biological molecule selected from the group consisting of interleukin 1β (IL-1β); interleukin-6 (IL-6); interleukin-6 receptor (IL-6R); interleukin-13 (IL-13); IL-13 receptor (IL-13R); PDGF; angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor; ST-2 receptor; and a protein genetically linked to age-related macular degeneration (AMD) risk. In some embodiments, the VEGF receptor is VEGFR1, VEGFR2, VEGFR3, membrane-bound VEGF-receptor (mbVEGFR), or soluble VEGF receptor (sVEGFR). In some embodiments, the protein genetically linked to AMD risk is selected from the group consisting of complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC, COL10A1; and TNFRSF10A.

In some embodiments of any of the preceding aspects, the antibody is a cysteine engineered antibody. In some embodiments, the cysteine engineered antibody comprises a cysteine mutation in the heavy chain selected from the group consisting of HC-A118C, HC-A140C, and HC-L174C (EU numbering), or a cysteine mutation in the light chain selected from the group consisting of LC-K149C and LC-V205C (Kabat numbering). In some embodiments, the cysteine mutation in the heavy chain is HC-A1180 (EU numbering). In some embodiments, the cysteine mutation in the heavy chain is HC-A140C (EU numbering). In some embodiments, the cysteine mutation in the heavy chain is HC-L174C (EU numbering). In some embodiments, the cysteine mutation in the light chain is LC-K1490 (Kabat numbering). In some embodiments, the cysteine mutation in the light chain is LC-V205C (Kabat numbering). In some embodiments, the HA polymer is covalently attached to the antibody at the cysteine mutation.

In another aspect, any of the preceding antibody conjugates can be used as a medicament.

In another aspect, any of the preceding antibody conjugates can be used in the manufacture of a medicament for treating an ocular disorder in a subject.

In another aspect, any of the preceding antibody conjugates can be used in reducing or inhibiting angiogenesis in a subject having an ocular disorder.

In another aspect, any of the preceding antibody conjugates can be used in treating an ocular disorder in a subject.

In some embodiments of any of the preceding aspects, the ocular disorder is selected from the group consisting of age-related macular degeneration (AMD), macular degeneration, macular edema, diabetic macular edema (DME) (including focal, non-center DME and diffuse, center-involved DME), retinopathy, diabetic retinopathy (DR) (including proliferative DR (PDR), non-proliferative DR (NPDR), and high-altitude DR), other ischemia-related retinopathies, retinopathy of prematurity (ROP), retinal vein occlusion (RVO) (including central (CRVO) and branched (BRVO) forms), CNV (including myopic CNV), corneal neovascularization, a disease associated with corneal neovascularization, retinal neovascularization, a disease associated with retinal/choroidal neovascularization, pathologic myopia, von Hippel-Lindau disease, histoplasmosis of the eye, familial exudative vitreoretinopathy (FEVR), Coats' disease, Norrie Disease, Osteoporosis-Pseudoglioma Syndrome (OPPG), subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (including infectious conjunctivitis and non-infectious (e.g., allergic) conjunctivitis), Leber congenital amaurosis, uveitis (including infectious and non-infectious uveitis), choroiditis, ocular histoplasmosis, blepharitis, dry eye, traumatic eye injury, and Sjögren's disease. In some embodiments, the ocular disorder is AMD, DME, DR, or RVO. In some embodiments, the ocular disorder is AMD. In some embodiments, the AMD is wet AMD. In some embodiments, the ocular disorder is DME.

In another aspect, the invention features a pharmaceutical composition comprising any of the antibody conjugates described herein a pharmaceutically acceptable carrier, excipient, or diluent. In some embodiments, the pharmaceutical composition further comprises a second agent, wherein the second agent is selected from the group consisting of an antibody, an anti-angiogenic agent, a cytokine, a cytokine antagonist, a corticosteroid, an analgesic, and a compound that binds to a second biological molecule. In some embodiments, the anti-angiogenic agent is a VEGF antagonist. In some embodiments, the VEGF antagonist is an anti-VEGF antibody, an anti-VEGF receptor antibody, a soluble VEGF receptor fusion protein, an aptamer, an anti-VEGF DARPin®, or a VEGFR tyrosine kinase inhibitor. In some embodiments, the anti-VEGF antibody is ranibizumab (LUCENTIS®), RTH-258, or a bispecific anti-VEGF antibody. In some embodiments, the bispecific anti-VEGF antibody is an anti-VEGF/anti-Ang2 antibody. In some embodiments, the anti-VEGF/anti-Ang2 antibody is RG-7716. In some embodiments, the soluble VEGF receptor fusion protein is aflibercept (EYLEA®). In some embodiments, the aptamer is pegaptanib (MACUGEN®). In some embodiments, the anti-VEGF DARPin® is abicipar pegol. In some embodiments, the VEGFR tyrosine kinase inhibitor is selected from the group consisting of 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787), semaxaminib (SU5416), and SUTENT® (sunitinib). In some embodiments, the second biological molecule is selected from the group consisting of IL-1β; IL-6; IL-6R; IL-13; IL-13R; PDGF; angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor; ST-2 receptor; and a protein genetically linked to AMD risk. In some embodiments, the VEGF receptor is VEGFR1, VEGFR2, VEGFR3, mbVEGFR, or sVEGFR. In some embodiments, the protein genetically linked to AMD risk is selected from the group consisting of complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC, COL10A1; and TNFRSF10A. In some embodiments, the compound that binds a second biological molecule is an antibody or antigen-binding fragment thereof. In some embodiments, the antigen-binding antibody fragment is selected from the group consisting of Fab, Fab-C, Fab'-SH, Fv, scFv, and (Fab')$_2$ fragments. In some embodiments, the antigen-binding antibody fragment is an Fab.

In another aspect, any of the preceding pharmaceutical compositions can be used as a medicament.

In another aspect, any of the preceding pharmaceutical compositions can be used in the manufacture of a medicament for treating an ocular disorder in a subject.

In another aspect, any of the preceding pharmaceutical compositions can be used in reducing or inhibiting angiogenesis in a subject having an ocular disorder.

In another aspect, any of the preceding pharmaceutical compositions can be used in treating an ocular disorder in a subject.

In some embodiments of any of the preceding aspects, the ocular disorder is selected from the group consisting of age-related macular degeneration (AMD), macular degeneration, macular edema, diabetic macular edema (DME) (including focal, non-center DME and diffuse, center-involved DME), retinopathy, diabetic retinopathy (DR) (including proliferative DR (PDR), non-proliferative DR (NPDR), and high-altitude DR), other ischemia-related retinopathies, retinopathy of prematurity (ROP), retinal vein occlusion (RVO) (including central (CRVO) and branched (BRVO) forms), CNV (including myopic CNV), corneal neovascularization, a disease associated with corneal neovascularization, retinal neovascularization, a disease associated with retinal/choroidal neovascularization, pathologic myopia, von Hippel-Lindau disease, histoplasmosis of the eye, familial exudative vitreoretinopathy (FEVR), Coats' disease, Norrie Disease, Osteoporosis-Pseudoglioma Syndrome (OPPG), subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (including infectious conjunctivitis and non-infectious (e.g., allergic) conjunctivitis), Leber congenital amaurosis, uveitis (including infectious and non-infectious uveitis), choroiditis, ocular histoplasmosis, blepharitis, dry eye, traumatic eye injury, and Sjögren's disease. In some embodiments, the ocular disorder is AMD, DME, DR, or RVO. In some embodiments, the ocular disorder is AMD. In some embodiments, the AMD is wet AMD. In some embodiments, the ocular disorder is DME.

In another aspect, the invention features a method of reducing or inhibiting angiogenesis in a subject having an ocular disorder, comprising administering to the subject an effective amount of any of the antibody conjugates described herein or any of the pharmaceutical compositions described herein, thereby reducing or inhibiting angiogenesis in the subject.

In another aspect, the invention features a method of treating an ocular disorder, the method comprising administering an effective amount of any of the antibody conjugates described herein or any of the pharmaceutical compositions described herein to a subject in need of such treatment.

In some embodiments of any of the preceding aspects, the ocular disorder is selected from the group consisting of age-related macular degeneration (AMD), macular degeneration, macular edema, diabetic macular edema (DME) (including focal, non-center DME and diffuse, center-involved DME), retinopathy, diabetic retinopathy (DR) (including proliferative DR (PDR), non-proliferative DR (NPDR), and high-altitude DR), other ischemia-related retinopathies, retinopathy of prematurity (ROP), retinal vein occlusion (RVO) (including central (CRVO) and branched (BRVO) forms), CNV (including myopic CNV), corneal neovascularization, a disease associated with corneal neovascularization, retinal neovascularization, a disease associated with retinal/choroidal neovascularization, pathologic myopia, von Hippel-Lindau disease, histoplasmosis of the eye, familial exudative vitreoretinopathy (FEVR), Coats' disease, Norrie Disease, Osteoporosis-Pseudoglioma Syndrome (OPPG), subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (including infectious conjunctivitis and non-infectious (e.g., allergic) conjunctivitis), Leber congenital amaurosis, uveitis (including infectious and non-infectious uveitis), choroiditis, ocular histoplasmosis, blepharitis, dry eye, traumatic eye injury, and Sjögren's disease. In some embodiments, the ocular disorder is AMD, DME, DR, or RVO. In some embodiments, the ocular disorder is AMD. In some embodiments, the AMD is wet AMD. In some embodiments, the ocular disorder is DME.

In some embodiments of any of the preceding aspects, the method further comprises administering to the subject an effective amount of a second agent, wherein the second agent is selected from the group consisting of an antibody, an anti-angiogenic agent, a cytokine, a cytokine antagonist, a corticosteroid, an analgesic, and a compound that binds to a second biological molecule. In some embodiments, the anti-angiogenic agent is a VEGF antagonist. In some embodiments, the VEGF antagonist is an anti-VEGF antibody, an anti-VEGF receptor antibody, a soluble VEGF receptor fusion protein, an aptamer, an anti-VEGF DARPin®, or a VEGFR tyrosine kinase inhibitor. In some embodiments, the anti-VEGF antibody is ranibizumab (LUCENTIS®), RTH-258, or a bispecific anti-VEGF antibody. In some embodiments, the bispecific anti-VEGF antibody is an anti-VEGF/anti-Ang2 antibody. In some embodiments, the anti-VEGF/anti-Ang2 antibody is RG-7716. In some embodiments, the soluble VEGF receptor fusion protein is aflibercept (EYLEA®). In some embodiments, the aptamer is pegaptanib (MACUGEN®). In some embodiments, the anti-VEGF DARPin® is abicipar pegol. In some embodiments, the VEGFR tyrosine kinase inhibitor is selected from the group consisting of 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787), semaxaminib (SU5416), and SUTENT® (sunitinib). In some embodiments, the second biological molecule is selected from the group consisting of IL-1β; IL-6; IL-6R; IL-13; IL-13R; PDGF; angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor; ST-2 receptor; and a protein genetically linked to AMD risk. In some embodiments, the VEGF receptor is VEGFR1, VEGFR2, VEGFR3, mbVEGFR, or sVEGFR. In some embodiments, the protein genetically linked to AMD risk is selected from the group consisting of complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC, COL10A1; and TNFRSF10A. In some embodiments, the compound that binds a second biological molecule is an antibody or antigen-binding fragment thereof. In some embodiments, the antigen-binding antibody fragment is selected from the group consisting of Fab, Fab-C, Fab'-SH, Fv, scFv, and (Fab')$_2$ fragments.

In some embodiments of any of the preceding aspects, the antibody conjugate or the pharmaceutical composition is administered intravitreally, ocularly, intraocularly, juxtasclerally, subtenonly, superchoroidally, topically, intravenously, intramuscularly, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, intraperitoneally, peritoneally, intraventricularly, subcutaneously, subconjunctivally, intravesicularly, mucosally, intrapericardially, intraumbilically, intraorbitally, orally, transdermally, by inhalation, by injection, by eye drop, by implantation, by infusion, by continuous infusion, by localized perfusion bathing target cells directly, by catheter, by lavage, in cremes, or in lipid compositions. In some embodiments, the antibody conjugate or the pharmaceutical composition is administered intravitreally, ocularly, intraocularly, juxtasclerally, subtenonly, superchoroidally, or topically. In some embodiments, the antibody conjugate or the pharmaceutical composition is administered intravitreally by injection. In some embodiments, the antibody conjugate or the pharmaceutical composition is administered topically by eye drop or ointment. In some embodiments, the antibody conjugate or the pharmaceutical composition is administered by a port delivery device.

In some embodiments of any of the preceding aspects, the subject is a human.

BRIEF DESCRIPTION OF THE DRAWINGS

FIG. 7 is a schematic diagram showing that standard Fab-C format molecules are designed to contain a free cysteine residue useful for conjugation by extending the standard Fab hinge peptide sequence to the first or second hinge disulfide cysteine. To minimize or prevent scrambling between the interchain disulfide and this free cysteine residue, the cysteine can instead be mutated onto the surface of the Fab at a location spatially further separated from the interchain disulfide (referred to herein as "ThioFabs").

FIG. 8A shows the intended configuration in which the hinge sequence cysteine is reduced and available for conjugation. FIG. 8B shows a cyclized heavy chain (HC) variant in which the hinge cysteine forms a disulfide bond with the HC cysteine residue that normally is part of the interchain disulfide bond, leaving the light chain (LC) interchain disulfide cysteine available for conjugation. FIG. 8C shows a LC variant in which the hinge cysteine forms a disulfide bond with the LC cysteine that normally forms part of the interchain disulfide bond, leaving the HC interchain disulfide cysteine available for conjugation.

FIGS. 10A and 10B are a series of graphs showing the results of limited Lys-C (FIG. 10A) and hyaluronidase (HAase) (FIG. 10B) enzymatic digests of HA-G6.31.AARR conjugates, confirming the presence of conjugation variants associated with conjugation through both cysteines normally occupied by the interchain disulfide.

FIG. 13A shows the Kabat numbering scheme for the 4D5 light chain.

FIG. 13B shows a sequential numbering scheme (left column) starting at the N-terminus in comparison with the Kabat numbering scheme (middle column) and EU numbering scheme (right column) for the 4D5 antibody.

DETAILED DESCRIPTION OF THE INVENTION

I. Definitions

Figure 1A:
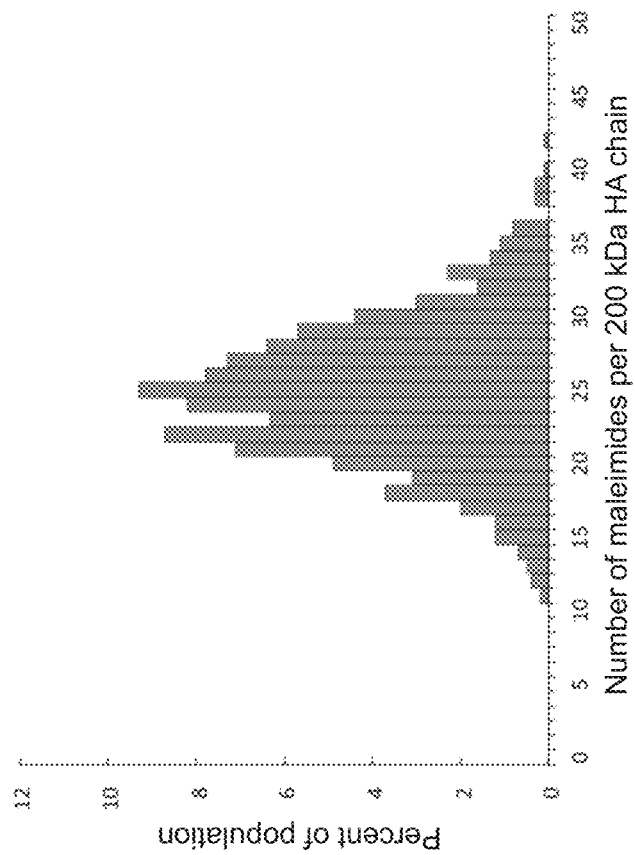
FIG. 1A is a graph showing a population distribution of molecular weights (in terms of molar mass) in a representative sample of 200 kDa HA.

The term "about" as used herein refers to the usual error range for the respective value readily known to the skilled person in this technical field. Reference to "about" a value or parameter herein includes (and describes) embodiments that are directed to that value or parameter per se.

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs) and/or framework regions (FRs), compared to a parent antibody which does not possess such alterations, such alterations resulting in an improvement in the affinity of the antibody for antigen.

The term "vascular endothelial growth factor" or "VEGF" refers to vascular endothelial growth factor protein A, as exemplified by SEQ ID NO: 47 (see also Swiss Prot Accession Number P15692, Gene ID (NCBI): 7422). The term "VEGF" encompasses the protein having the amino acid sequence of SEQ ID NO: 47 as well as homologues and isoforms thereof. The term "VEGF" also encompasses the known isoforms, e.g., splice isoforms, of VEGF, e.g., $VEGF_{111}$, $VEGF_{121}$, $VEGF_{145}$, $VEGF_{165}$, $VEGF_{189}$, and $VEGF_{206}$, together with the naturally-occurring allelic and processed forms thereof, including the 110-amino acid human vascular endothelial cell growth factor generated by plasmin cleavage of $VEGF_{165}$ as described in Ferrara Mol. Biol. Cell. 21:687 (2010), Leung et al., Science, 246:1306 (1989), and Houck et al., Mol. Endocrin., 5:1806 (1991). The term "VEGF" also refers to VEGFs from non-human species such as mouse, rat or primate. Sometimes the VEGF from a specific species are indicated by terms such as hVEGF for human VEGF, mVEGF for murine VEGF, and the like. The term "VEGF" is also used to refer to truncated forms of the polypeptide comprising amino acids 8 to 109 or 1 to 109 of the 165-amino acid human vascular endothelial cell growth factor. Reference to any such forms of VEGF may be identified in the present application, e.g., by "$VEGF_{109}$," "VEGF (8-109)," "VEGF (1-109)" or "$VEGF_{165}$." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF. The term "VEGF variant" as used herein refers to a VEGF polypeptide which includes one or more amino acid mutations in the native VEGF sequence. Optionally, the one or more amino acid mutations include amino acid substitution(s). For purposes of shorthand designation of VEGF variants described herein, it is noted that numbers refer to the amino acid residue position along the amino acid sequence of the putative native VEGF (provided in Leung et al., supra and Houck et al., supra). Unless specified otherwise, the term "VEGF" as used herein indicates VEGF-A.

The terms "anti-VEGF antibody," an "antibody that binds to VEGF," and "antibody that specifically binds VEGF" refer to an antibody that is capable of binding VEGF with sufficient affinity such that the antibody is useful as a diagnostic and/or therapeutic agent in targeting VEGF. In one embodiment, the extent of binding of an anti-VEGF antibody to an unrelated, non-VEGF protein is less than about 10% of the binding of the antibody to VEGF as measured, for example, by a radioimmunoassay (RIA). In certain embodiments, an antibody that binds to VEGF has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g., from $10^{-8}$ M to $10^{-13}$ M, e.g., from $10^{-9}$M to $10^{-13}$ M). In certain embodiments, an anti-VEGF antibody binds to an epitope of VEGF that is conserved among VEGF from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab-C, Fab'-SH, F(ab')2; diabodies; linear antibodies; single-chain antibody molecules (e.g., scFv); and multispecific antibodies formed from antibody fragments. In some instances, examples of antibody fragments include but are not limited to Fv, Fab, Fab', Fab'-SH, F(ab')2; diabodies;

linear antibodies; single-chain antibody molecules (e.g., scFv); and multispecific antibodies formed from antibody fragments.

Papain digestion of antibodies produces two identical antigen-binding fragments, called "Fab" fragments, and a residual "Fc" fragment, a designation reflecting the ability to crystallize readily. The Fab fragment consists of an entire light (L) chain along with the variable region domain of the heavy (H) chain (VH), and the first constant domain of one heavy chain (CH1). Pepsin treatment of an antibody yields a single large F(ab')$_2$ fragment which roughly corresponds to two disulfide linked Fab fragments having divalent antigen-binding activity and is still capable of cross-linking antigen. Fab' fragments differ from Fab fragments by having additional few residues at the carboxy terminus of the CH1 domain including one or more cysteines from the antibody hinge region. Fab-C molecules are Fab molecules that are expressed such that the sequence is truncated at the first hinge cysteine, resulting in a Fab with a free cysteine directly upon expression (see, e.g., Shatz et al. *Mol. Pharmaceutics* 2016; PubMed identifier (PMID) 27244474). For example, a Fab-C molecule may have a free cysteine at position Cys227 of the heavy chain. In other instances, a Fab-C molecule may have a free cysteine at position Cys229 of the heavy chain. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, MD (1991).

"Fv" consists of a dimer of one heavy- and one light-chain variable region domain in tight, noncovalent association. From the folding of these two domains emanate six hyper-variable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although often at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the VH and VL domains which enables the sFv to form the desired structure for antigen binding. For a review of sFv, see Pluckthun in *The Pharmacology of Monoclonal Antibodies, vol.* 113, Rosenburg and Moore eds., Springer-Verlag, New York, pp. 269-315 (1994).

The term "diabodies" refers to small antibody fragments prepared by constructing sFv fragments (see preceding paragraph) with short linkers (about 5-10 residues) between the VH and VL domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the VH and VL domains of the two antibodies are present on different polypeptide chains. Diabodies are described more fully in, for example, EP 404,097; WO 93/11161; and Hollinger et al., *Proc. Natl. Acad. Sci. USA,* 90:6444-6448 (1993).

A "blocking" antibody or an "antagonist" antibody is one which inhibits or reduces biological activity of the antigen it binds. Certain blocking antibodies or antagonist antibodies substantially or completely inhibit the biological activity of the antigen.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

A "cysteine engineered antibody" or "cysteine engineered antibody variant" is an antibody in which one or more residues of an antibody are substituted with cysteine residues. In certain instances, cysteine engineered antibodies may be referred to as THIOMAB™ antibodies or ThioFab antibodies. The thiol group(s) of the cysteine engineered antibodies can be conjugated to other moieties, e.g., polymers (e.g., HA polymers, including monodisperse HA polymers). In particular embodiments, the substituted residues occur at accessible sites of the antibody. By substituting those residues with cysteine, reactive thiol groups are thereby positioned at accessible sites of the antibody and may be used to conjugate the antibody to other moieties, such as polymers (e.g., HA polymers). For example, a cysteine engineered antibody may be an antibody with a single mutation of a non-cysteine native residue to a cysteine in the light chain (e.g., LC-G64C, LC-I106C, LC-R108C, LC-R142C, or LC-K149C according to Kabat numbering) or in the heavy chain (e.g., HC-D101C, HC-V184C, or HC-T205C according to Kabat numbering, or HC-T114C, HC-A140C, HC-L174C, HC-L179C, HC-T187C, HC-T209C, HC-V262C, HC-G371C, HC-Y373C, HC-E382C, HC-S424C, HC-N434C, and HC-Q438C according to EU numbering (i.e., HC-A136C according to Kabat numbering is HC-A140C according to EU numbering)) (see FIGS. 13A and 13B). In particular instances, a cysteine engineered antibody may include a cysteine mutation in the heavy chain selected from the group consisting of HC-A118C, HC-A140C, and HC-L174C (EU numbering), or a cysteine mutation in the light chain selected from the group consisting of LC-V205C and LC-K149C (Kabat numbering). In some instances, a cysteine engineered antibody has a single cysteine mutation in either the heavy or light chain such that each full-length antibody (i.e., an antibody with two heavy chains and two light chains) has two engineered cysteine residues, and each Fab fragment has one engineered cysteine residue. In other instances, a cysteine engineered antibody has more than one cysteine mutations (e.g., 2, 3, 4, or 5 cysteine mutations).

A "free cysteine amino acid" refers to a cysteine amino acid residue which has been engineered into a parent antibody, has a thiol functional group (—SH), and is not paired as an intramolecular or intermolecular disulfide bridge.

The term "thiol reactivity value" is a quantitative characterization of the reactivity of free cysteine amino acids. The thiol reactivity value is the percentage of a free cysteine amino acid in a cysteine engineered antibody which reacts with a thiol-reactive reagent, and converted to a maximum value of 1. For example, a free cysteine amino acid on a cysteine engineered antibody which reacts in 100% yield with a thiol-reactive reagent, such as a biotin-maleimide reagent, to form a biotin-labelled antibody has a thiol reactivity value of 1.0. Another cysteine amino acid engineered into the same or different parent antibody which reacts in 90% yield with a thiol-reactive reagent has a thiol reactivity value of about 0.9. Another cysteine amino acid engineered into the same or different parent antibody which reacts in 80% yield with a thiol-reactive reagent has a thiol reactivity value of about 0.8. Another cysteine amino acid engineered into the same or different parent antibody which reacts in 70% yield with a thiol-reactive reagent has a thiol reactivity value of about 0.7. Another cysteine amino acid engineered into the same or different parent antibody which reacts in 60% yield with a thiol-reactive reagent has a thiol reactivity value of about 0.6. Another cysteine amino acid engineered into the same or different parent antibody which reacts in 50% yield with a thiol-reactive reagent has a thiol reactivity value of about 0.5. Another cysteine amino acid engineered into the same or different parent antibody which reacts in 40% yield with a thiol-reactive reagent has a thiol reactivity value of about 0.4. Another cysteine amino acid engineered into the same or different parent antibody which reacts in 30% yield with a thiol-reactive reagent has a thiol reactivity value of about 0.3. Another cysteine amino acid engineered into the same or different parent antibody which reacts in 20% yield with a thiol-reactive reagent has a thiol reactivity value of about 0.2. Another cysteine amino acid engineered into the same or different parent antibody which reacts in 10% yield with a thiol-reactive reagent has a thiol reactivity value of about 0.1. Another cysteine amino acid engineered into the same or different parent antibody which fails totally to react with a thiol-reactive reagent has a thiol reactivity value of 0. Determination of the thiol reactivity value of a particular cysteine may be conducted by ELISA assay (e.g., a PHESELECTOR assay as described herein), mass spectroscopy, liquid chromatography, autoradiography, or other quantitative analytical tests.

A "parent antibody" is an antibody comprising an amino acid sequence from which one or more amino acid residues are replaced by one or more cysteine residues. The parent antibody may comprise a native or wild type sequence. The parent antibody may have pre-existing amino acid sequence modifications (such as additions, deletions and/or substitutions) relative to other native, wild type, or modified forms of an antibody. A parent antibody may be directed against a target antigen of interest, e.g., a biologically important polypeptide, such as VEGF. Any of the antibodies described herein (e.g., anti-VEGF antibodies) may be a parent antibody.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down-regulation of cell surface receptors (e.g. B cell receptor); and B cell activation.

"Framework" or "framework region" or "FR" refers to variable domain residues other than hypervariable region (HVR) residues. The FR of a variable domain generally consists of four FR domains: FR1, FR2, FR3, and FR4.

The terms "full-length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, FR residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

The term "variable" refers to the fact that certain segments of the variable domains differ extensively in sequence among antibodies. The variable or "V" domain mediates antigen binding and defines specificity of a particular antibody for its particular antigen. However, the variability is not evenly distributed across the span of the variable domains. Instead, the V regions consist of relatively invariant stretches called framework regions (FRs) of 15-30 amino acids separated by shorter regions of extreme variability called "hypervariable regions" that are each 9-12 amino acids long. The term "hypervariable region" or "HVR" when used herein refers to the amino acid residues of an antibody which are responsible for antigen-binding. The hypervariable region generally comprises amino acid residues from, for example, around about residues 24-34 (L1), 50-56 (L2) and 89-97 (L3) in the VL, and around about residues 26-35 (H1), 49-65 (H2) and 95-102 (H3) in the VH (in one embodiment, H1 is around about residues 31-35); Kabat et al., Sequences of Proteins of Immunological Interest, 5th Ed. Public Health Service, National Institutes of Health, Bethesda, MD (1991)) and/or those residues from a "hypervariable loop" (e.g., residues 26-32 (L1), 50-52 (L2), and 91-96 (L3) in the VL, and 26-32 (H1), 53-55 (H2), and 96-101 (H3) in the VH; Chothia and Lesk, J. Mol. Biol. 196:901-917 (1987). The variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, MD (1991)). Accordingly, the HVR and FR sequences generally appear in the following sequence in VH (or VL): FR1-H1(L1)-FR2-H2(L2)-FR3-H3(L3)-FR4. The constant domains are not involved directly in binding an antibody to an antigen, but exhibit various effector functions, such as participation of the antibody in antibody dependent cellular cytotoxicity (ADCC).

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (see, e.g., Kabat et al., Sequences of Immunological Interest. 5th Ed. Public Health Service, National Institutes of Health, Bethesda, Md. (1991), which is herein incorporated by reference in its entirety). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU numbering system, also called the EU index, as described in Kabat et al., Sequences of Proteins of Immunological Interest, 5th Ed. Public Health Service, National Institutes of Health, Bethesda, MD, 1991.

Unless otherwise indicated, HVR residues and other residues in the variable domain (e.g., FR residues) are numbered herein according to Kabat et al., supra.

The term an "isolated antibody" when used to describe the various antibodies disclosed herein, means an antibody that has been identified and separated and/or recovered from a cell or cell culture from which it was expressed. Contaminant components of its natural environment are materials that would typically interfere with diagnostic or therapeutic uses for the polypeptide, and can include enzymes, hormones, and other proteinaceous or non-proteinaceous solutes. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For a review of methods for assessment of antibody purity, see, for example, Flatman et al., J. Chromatogr. B 848:79-87 (2007). In preferred embodiments, the antibody will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Isolated antibody includes antibodies in situ within recombinant cells, because at least one component of the polypeptide natural environment will not be present. Ordinarily, however, isolated polypeptide will be prepared by at least one purification step.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "multispecific antibody" is used in the broadest sense and specifically covers an antibody comprising a heavy chain variable domain (VH) and a light chain variable domain (VL), where the VH-VL unit has polyepitopic specificity (i.e., is capable of binding to two different epitopes on one biological molecule or each epitope on a different biological molecule). Such multispecific antibodies include, but are not limited to, full-length antibodies, antibodies having two or more VL and VH domains, antibody fragments such as Fab, Fab', Fab-C. Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Dual specificity" or "bispecificity" refers to the ability to specifically bind to two different epitopes on the same or different target(s). However, in contrast to bispecific antibodies, dual-specific antibodies have two antigen-binding arms that are identical in amino acid sequence and each Fab arm is capable of recognizing two antigens. Dual-specificity allows the antibodies to interact with high affinity with two different antigens as a single Fab or IgG molecule. According to one embodiment, the multispecific antibody in an IgG1 form binds to each epitope with an affinity of 5 µM to 0.001 pM, 3 µM to 0.001 pM, 1 µM to 0.001 pM, 0.5 µM to 0.001 pM or 0.1 µM to 0.001 pM. "Monospecific" refers to the ability to bind only one epitope.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

With regard to the binding of a antibody to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of $10^{-4}$ M or lower, alternatively $10^{-5}$ M or lower, alternatively $10^{-6}$ M or lower, alternatively $10^{-7}$ M or lower, alternatively $10^{-8}$ M or lower, alternatively $10^{-9}$ M or lower, alternatively $10^{-10}$ M or lower, alternatively $10^{-11}$ M or lower, alternatively $10^{-12}$ M or lower or a Kd in the range of $10^{-4}$ M to $10^{-6}$ M or $10^{-6}$ M to $10^{-10}$ M or $10^{-7}$ M to $10^{-9}$ M. As will be appreciated by the skilled artisan, affinity and Kd values are inversely related. A high affinity for an antigen is measured by a low Kd value. In one embodiment, the term "specific binding" refers to binding where a molecule binds to a particular polypeptide or epitope on a particular polypeptide without substantially binding to any other polypeptide or polypeptide epitope.

A "nucleic acid encoding an anti-VEGF antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

As used herein, "administering" is meant a method of giving a dosage of a compound (e.g., an antibody (e.g., a cysteine engineered anti-VEGF antibody) or an antibody conjugate (e.g., a monodisperse HA conjugate) of the invention) or a composition (e.g., a pharmaceutical composition, e.g., a pharmaceutical composition including an antibody or an antibody conjugate of the invention) to a subject. The compositions utilized in the methods described herein can be administered, for example, intravitreally (e.g., by intravitreal injection), by eye drop, intramuscularly, intravenously, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, peritoneally, subcutaneously, subconjunctivally, intravesicularly, mucosally, intrapericardially, intraumbilically, intraocularly, intraorbitally, orally, topically, transdermally, by inhalation, by injection, by implantation, by infusion, by continuous infusion, by localized perfusion bathing target cells directly, by catheter, by lavage, in cremes, or in lipid compositions. The compositions utilized in the methods described herein can also be administered systemically or locally. The method of administration can vary depending on various factors (e.g., the compound or composition being administered and the severity of the condition, disease, or disorder being treated).

"Angiogenesis" refers to the process through which new blood vessels form from pre-existing blood vessels. Angiogenesis is distinct from vasculogenesis, which is the de novo formation of endothelial cells from mesoderm cell precursors. Disorders associated with pathological angiogenesis can be treated by compositions and methods of the invention. Exemplary disorders associated with pathological angiogenesis include but are not limited to ocular conditions (non-limiting ocular conditions include, for example, retinopathy including proliferative diabetic retinopathy, choroidal neovascularization (CNV), age-related macular degeneration (AMD), diabetic and other ischemia-related retinopathies, diabetic macular edema (DME), pathologic myopia, von Hippel-Lindau disease, histoplasmosis of the eye, retinal vein occlusion (including central (CRVO) and branched (BRVO) forms), corneal neovascularization, retinal neovascularization, retinopathy of prematurity (ROP), familial exudative vitreoretinopathy (FEVR), Coats' disease, Norrie Disease, Osteoporosis-Pseudoglioma Syndrome (OPPG), subconjunctival hemorrhage, rubeosis, ocular neovascular disease, neovascular glaucoma, and hypertensive retinopathy). Additional ocular disorders are described below.

The term "ocular disorder," as used herein, includes any ocular disorder (also referred to interchangeably herein as "ocular condition") associated with pathological angiogenesis. An ocular disorder may be characterized by altered or unregulated proliferation and/or invasion of new blood vessels into the structures of ocular tissues such as the retina or cornea. Non-limiting ocular disorders include, for example, AMD (e.g., wet AMD, dry AMD, intermediate AMD, advanced AMD, and geographic atrophy (GA)), macular degeneration, macular edema, DME (e.g., focal, non-center DME and diffuse, center-involved DME), retinopathy, diabetic retinopathy (DR) (e.g., proliferative DR (PDR), non-proliferative DR (NPDR), and high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g., allergic) conjunctivitis), Leber congenital amaurosis (also known as Leber's congenital amaurosis or LCA), uveitis (including infectious and non-infectious uveitis), choroiditis (e.g., multifocal choroiditis), ocular histoplasmosis, blepharitis, dry eye, traumatic eye injury, Sjögren's disease, and other ophthalmic diseases wherein the disease or disorder is associated with ocular neovascularization, vascular leakage, and/or retinal edema. Additional exemplary ocular disorders include diseases associated with rubeosis (neovascularization of the angle) and diseases caused by the abnormal proliferation of fibrovascular or fibrous tissue, including all forms of proliferative vitreoretinopathy.

Exemplary diseases associated with corneal neovascularization include, but are not limited to, epidemic keratoconjunctivitis, vitamin A deficiency, contact lens overwear, atopic keratitis, superior limbic keratitis, terygium keratitis sicca, Sjögren's syndrome, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, marginal keratolysis, rheumatoid arthritis, systemic lupus, polyarteritis, trauma, Wegener's sarcoidosis, scleritis, Stevens-Johnson syndrome, periphigoid radial keratotomy, and corneal graph rejection.

Exemplary diseases associated with retinal/choroidal neovascularization include, but are not limited to, diabetic retinopathy, macular degeneration, sickle cell anemia, sarcoid, syphilis, pseudoxanthoma elasticum, Paget's disease, vein occlusion, artery occlusion, carotid obstructive disease, chronic uveitis/vitritis, mycobacterial infections, Lyme's disease, systemic lupus erythematosis, retinopathy of prematurity, retinitis pigmentosa, retina edema (including macular edema), Eales disease, Behcet's disease, infections causing retinitis or choroiditis (e.g., multifocal choroidits), presumed ocular histoplasmosis, Best's disease (vitelliform macular degeneration), myopia, optic pits, Stargart's disease, pars planitis, retinal detachment (e.g., chronic retinal detachment), hyperviscosity syndromes, toxoplasmosis, trauma, and post-laser complications.

An "angiogenic factor or agent" is a growth factor which stimulates the development of blood vessels, e.g., promote angiogenesis, endothelial cell growth, stability of blood vessels, and/or vasculogenesis, etc. For example, angiogenic factors, include, but are not limited to, e.g., VEGF and members of the VEGF family, PIGF, PDGF family, fibroblast growth factor family (FGFs), TIE ligands (Angiopoietins), ephrins, Del-1, fibroblast growth factors: acidic (aFGF) and basic (bFGF), Follistatin, Granulocyte colony-stimulating factor (G-CSF), Hepatocyte growth factor (HGF)/scatter factor (SF), Interleukin-8 (IL-8), Leptin, Midkine, Placental growth factor, Platelet-derived endothelial cell growth factor (PD-ECGF), Platelet-derived growth factor, especially PDGF-BB or PDGFR-beta, Pleiotrophin (PTN), Progranulin, Proliferin, Transforming growth factor-alpha (TGF-alpha), Transforming growth factor-beta (TGF-beta), Tumor necrosis factor-alpha (TNF-alpha), Vascular endothelial growth factor (VEGF)/vascular permeability factor (VPF), etc. It would also include factors that accelerate wound healing, such as growth hormone, insulin-like growth factor-I (IGF-I), VIGF, epidermal growth factor (EGF), CTGF and members of its family, and TGF-alpha and TGF-beta. See, for example, Klagsbrun and D'Amore, *Annu. Rev. Physiol,* 53:217-39 (1991); Streit and Detmar, *Oncogene,* 22:3172-3179 (2003); Ferrara & Alitalo, *Nature Medicine* 5(12):1359-1364 (1999); Tonini et al., *Oncogene,* 22:6549-6556 (2003) (e.g., Table 1 listing known angiogenic factors); and Sato, *Int. J. Clin. Oncol,* 8:200-206 (2003).

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined above, e.g., VEGF antagonists (e.g., antibodies to VEGF-A or to the VEGF-A receptor (e.g., KDR receptor or Flt-1 receptor)), PDGF antagonists (e.g., anti-PDGFR inhibitors such as GLEEVEC™ (Imatinib Mesylate)). Anti-angiogenesis agents also include native angiogenesis inhibitors, e.g., angiostatin, endostatin, etc. See, for example, Klagsbrun and D'Amore, *Annu. Rev. Physiol,* 53:217-39 (1991); Streit and Detmar, *Oncogene,* 22:3172-3179 (2003) (e.g., Table 3 listing anti-angiogenic therapy in malignant melanoma); Ferrara & Alitalo, *Nature Medicine* 5(12):1359-1364 (1999); Tonini et al., *Oncogene,* 22:6549-6556 (2003) (e.g., Table 2 listing known antiangiogenic factors); and, Sato Int. *J. Clin. Oncol,* 8:200-206 (2003) (e.g., Table 1 lists anti-angiogenic agents used in clinical trials).

The term "VEGF antagonist," as used herein, refers to a molecule capable of binding to VEGF, reducing VEGF expression levels, or neutralizing, blocking, inhibiting, abrogating, reducing, or interfering with VEGF biological activities, including, but not limited to, VEGF binding to one or more VEGF receptors, VEGF signaling, and VEGF-mediated angiogenesis and endothelial cell survival or proliferation. For example, a molecule capable of neutralizing, blocking, inhibiting, abrogating, reducing, or interfering with VEGF biological activities can exert its effects by binding to one or more VEGF receptor (VEGFR) (e.g., VEGFR1, VEGFR2, VEGFR3, membrane-bound VEGF receptor (mbVEGFR), or soluble VEGF receptor (sVEGFR)). Included as VEGF antagonists useful in the methods of the invention are polypeptides that specifically bind to VEGF, anti-VEGF antibodies and antigen-binding fragments thereof, receptor molecules and derivatives which bind specifically to VEGF thereby sequestering its binding to one or more receptors, fusions proteins (e.g., VEGF-Trap (Regeneron)), and VEGF$_{121}$-gelonin (Peregrine). VEGF antagonists also include antagonist variants of VEGF polypeptides, antisense nucleobase oligomers complementary to at least a fragment of a nucleic acid molecule encoding a VEGF polypeptide; small RNAs complementary to at least a fragment of a nucleic acid molecule encoding a VEGF polypeptide; ribozymes that target VEGF; peptibodies to VEGF; and VEGF aptamers. VEGF antagonists also include polypeptides that bind to VEGFR, anti-VEGFR antibodies, and antigen-binding fragments thereof, and derivatives which bind to VEGFR thereby blocking, inhibiting, abrogating, reducing, or interfering with VEGF biological activities (e.g., VEGF signaling), or fusions proteins. VEGF antagonists also include nonpeptide small molecules that bind to VEGF or VEGFR and are capable of blocking, inhibiting, abrogating, reducing, or interfering with VEGF biological activities. Thus, the term "VEGF activities" specifically includes VEGF-mediated biological activities of VEGF. In certain embodiments, the VEGF antagonist reduces or inhibits, by at least 10%, 20%, 30%, 40%, 50%, 60%, 70%, 80%, 90% or more, the expression level or biological activity of VEGF. In some embodiments, the VEGF inhibited by the VEGF-specific antagonist is VEGF (8-109), VEGF (1-109), or VEGF$_{165}$.

As used herein VEGF antagonists can include, but are not limited to, anti-VEGFR2 antibodies and related molecules (e.g., ramucirumab, tanibirumab, aflibercept), anti-VEGFR1 antibodies and related molecules (e.g., icrucumab, aflibercept (VEGF Trap-Eye; EYLEA®), and ziv-aflibercept (VEGF Trap; ZALTRAP®)), bispecific VEGF antibodies (e.g., MP-0250, vanucizumab (VEGF-ANG2), and bispecific antibodies disclosed in US 2001/0236388), bispecific antibodies including combinations of two of anti-VEGF, anti-VEGFR1, and anti-VEGFR2 arms, anti-VEGF antibodies (e.g., bevacizumab, sevacizumab, and ranibizumab), and nonpeptide small molecule VEGF antagonists (e.g., pazopanib, axitinib, vandetanib, stivarga, cabozantinib, lenvatinib, nintedanib, orantinib, telatinib, dovitinig, cediranib, motesanib, sulfatinib, apatinib, foretinib, famitinib, and tivozanib). Additional VEGF antagonists are described below.

An "effective amount" of an agent, e.g., a pharmaceutical formulation, refers to an amount effective, at dosages and for periods of time necessary, to achieve the desired therapeutic or prophylactic result.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human. A "subject" may be a "patient."

A "disorder" is any condition that would benefit from treatment with the antibody. For example, mammals who suffer from or need prophylaxis against abnormal angiogenesis (excessive, inappropriate or uncontrolled angiogenesis). This includes chronic and acute disorders or diseases including those pathological conditions which predispose the mammal to the disorder in question. Non-limiting examples of disorders to be treated herein include disorders associated with pathological angiogenesis (e.g., ocular disorders).

The term "package insert" is used to refer to instructions customarily included in commercial packages of therapeutic products, that contain information about the indications, usage, dosage, administration, combination therapy, contraindications and/or warnings concerning the use of such therapeutic products.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The term "pharmaceutical formulation" refers to a preparation which is in such form as to permit the biological activity of an active ingredient (e.g., an antibody conjugate) contained therein to be effective, and which contains no additional components which are unacceptably toxic to a subject to which the formulation would be administered.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, antibody conjugates of the invention or other compositions that include an antibody conjugate of the invention (e.g., a pharmaceutical formulation) are used to delay development of a disease or to slow the progression of a disease.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

A "variant" or "mutant" of a starting or reference polypeptide (e.g., a reference antibody or its variable domain(s)/HVR(s)), is a polypeptide that (1) has an amino acid sequence different from that of the starting or reference polypeptide and (2) was derived from the starting or reference polypeptide through either natural or artificial (manmade) mutagenesis. Such variants include, for example, deletions from, and/or insertions into and/or substitutions of, residues within the amino acid sequence of the polypeptide of interest, referred to herein as "amino acid residue alterations." Thus, a variant HVR refers to a HVR comprising a variant sequence with respect to a starting or reference polypeptide sequence (such as that of a source antibody or antigen binding fragment). An amino acid residue alteration, in this context, refers to an amino acid different from the amino acid at the corresponding position in a starting or reference polypeptide sequence (such as that of a reference antibody or fragment thereof). Any combination of deletion, insertion, and substitution may be made to arrive at the final variant or mutant construct, provided that the final construct possesses the desired functional characteristics. The amino acid changes also may alter post-translational processes of the polypeptide, such as changing the number or position of glycosylation sites.

A "wild-type (WT)" or "reference" sequence or the sequence of a "wild-type" or "reference" protein/polypeptide, such as an HVR or a variable domain of a reference antibody, may be the reference sequence from which variant polypeptides are derived through the introduction of mutations. In general, the "wild-type" sequence for a given protein is the sequence that is most common in nature. Similarly, a "wild-type" gene sequence is the sequence for that gene which is most commonly found in nature. Mutations may be introduced into a "wild-type" gene (and thus the protein it encodes) either through natural processes or through man-induced means. The products of such processes are "variant" or "mutant" forms of the original "wild-type" protein or gene.

By "isoelectric point (pI)" is meant the pH at which a molecule (e.g., a protein, such as an antibody) carries no net electrical charge, also referred to in the art as "pH(I)" or "IEP."

As used herein, an "antibody conjugate" is an antibody covalently attached to one or more polymers. Any suitable polymer may be conjugated to an antibody, for example, a hydrophilic polymer (e.g., hyaluronic acid (HA) or polyethylene glycol (PEG)) or a hydrophobic polymer (e.g., poly (lactic-co-glycolic acid) (PLGA)). In particular embodiments, the polymer is HA (also referred to herein as "HA conjugates").

As used herein, the term "polymer" means a molecule that includes repeating structural units (i.e., monomers) connected by chemical bonds in a linear, circular, branched, crosslinked, or dendrimeric manner, or a combination thereof. A polymer may be synthetic or naturally occurring, or a combination thereof. It is to be understood that the term "polymer" encompasses copolymers, which are polymers that include two or more different monomers. A polymer may also be a homopolymer, which is a polymer that includes only a single type of monomer.

The term "polydispersity index (PDI)" refers to a measure of the broadness of the molecular weight distribution of a polymer. PDI is also referred to in the art as "dispersity index," "heterogeneity index," or "dispersity (Đ)." The PDI of a polymer sample may be calculated using equation (I): $Đ_M = M_w/M_n$ where $M_w$ is the weight-average molar mass and $M_n$ is the number-average molar mass. Unless indicated otherwise, PDI is calculated according to equation (I).

A polymer sample may be considered "monodisperse" (also known in the art as uniform) or "polydisperse" (also known in the art as non-uniform). As used herein, the term "monodisperse" with respect to an HA polymer or HA conjugate sample means that the HA polymer or HA conjugate sample has a PDI of less than or equal to about 1.1, e.g., about 1.001, about 1.02, about 1.03, about 1.04, about 1.05, about 1.06, about 1.07, about 1.08, about 1.09, or about 1.1. For example, a monodisperse HA polymer or HA conjugate sample may have a PDI between 1.0 to about 1.1 (e.g., between 1 to about 1.1, between 1 to about 1.09, between 1 to about 1.08, between 1 to about 1.07, between 1 to about 1.06, between 1 to about 1.05, between 1 to about 1.04, between 1 to about 1.03, between 1 to about 1.02, between 1 to about 1.01, between 1 to about 1.005, between about 1.001 to about 1.1, between about 1.001 to about 1.1, between about 1.001 to about 1.09, between about 1.001 to about 1.08, between about 1.001 to about 1.07, between about 1.001 to about 1.06, between about 1.001 to about 1.05, between about 1.001 to about 1.04, between about 1.001 to about 1.03, between about 1.001 to about 1.02, between about 1.001 to about 1.01, between about 1.001 to about 1.005, between about 1.001 to about 1.004, between about 1.001 to about 1.003, between about 1.001 to about 1.002, between about 1.0001 to about 1.1, between about 1.0001 to about 1.09, between about 1.0001 to about 1.08, between about 1.0001 to about 1.07, between about 1.0001 to about 1.06, between about 1.0001 to about 1.05, between about 1.0001 to about 1.04, between about 1.0001 to about 1.03, between about 1.0001 to about 1.02, between about 1.0001 to about 1.01, between about 1.0001 to about 1.005, between about 1.0001 to about 1.004, between about 1.0001 to about 1.003, between about 1.0001 to about 1.002, or between about 1.0001 to about 1.005).

In contrast, the term "polydisperse" means that the HA polymer or HA conjugate sample has a PDI of greater than 1.1, e.g., about 1.3, about 1.4, about 1.5, about 1.6, about 1.7, about 1.8, or higher. For example, in some embodiments, a polydisperse HA polymer or HA conjugate sample has a PDI of between about 1.3 to about 2, about 1.4 to about 2, about 1.5 to about 2, about 1.6 to about 2, about 1.7 to about 2, about 1.8 to about 2, or about 1.9 to about 2.

The terms "hyaluronic acid," "hyaluranon," and "HA," which are used interchangeably herein, refer to a polymeric glycosaminoglycan (GAG), which contains repeating disaccharide units of N-acetyl glucosamine and glucuronic acid. HA is an anionic, nonsulfated GAG, which can be found, for example, in extracellular matrix (e.g., in the vitreous of the eye), connective tissue, epithelial, and neural tissue.

The term "polyethylene glycol" or "PEG" as used herein, refers to a polyether compound that is also known as polyethylene oxide (PEO) or polyoxyethylene (POE), depending on its molecular weight. PEG may have a structure of H—(O—$CH_2$—$CH_2$)$_n$—OH, wherein n is any suitable integer. The PEG may be a branched PEG, a star PEG, or a comb PEG. The PEG may be, for example, a PEG tetramer, a PEG hexamer, or a PEG octamer.

The term "clearance," as used herein, refers to the volume of a substance (e.g., an anti-VEGF antibody, an antibody conjugate, a fusion protein (e.g., a Fab fusion protein), or a polymeric formulation) cleared from a compartment (e.g., the eye (e.g., the vitreous)) per unit time.

The term "half-life" refers to the time required for the concentration of a substance (e.g., an anti-VEGF antibody, an antibody conjugate, a fusion protein (e.g., a Fab fusion protein), or a polymeric formulation) to decrease by one-half, in vivo (e.g., in the eye (e.g., the vitreous)) or in vitro.

II. Compositions and Methods

The invention provides antibody conjugates that include polymers (e.g., monodisperse polymers, including monodisperse HA polymers) linked to antibodies (e.g., anti-VEGF antibodies, including any anti-VEGF antibody described herein), cysteine engineered antibodies that can be used, for example, in preparing antibody conjugates, compositions that include antibody conjugates (e.g., pharmaceutical compositions), as well as methods of making and using the same, for example, for therapeutic uses (e.g., treatment of ocular disorders).

A. Exemplary Antibodies for Use in Conjugates of the Invention

The invention provides antibody conjugates that include antibodies (e.g., anti-VEGF antibodies) covalently linked to polymers (e.g., monodisperse polymers). Any suitable antibody (e.g., anti-VEGF antibody) may be used. For example, the antibody may specifically bind to an antigen selected from the group consisting of VEGF; interleukin-1 beta (IL-1β); interleukin-6 (IL-6); interleukin-6 receptor (IL-6R); interleukin-13 (IL-13); IL-13 receptor (IL-13R); PDGF (e.g., PDGF-BB); angiopoietin; angiopoietin 2 (Ang2); Tie2; S1P; integrins αvβ3, αvβ5, and α5β1; betacellulin; apelin/APJ; erythropoietin; complement factor D; TNFα; HtrA1; a VEGF receptor (e.g., VEGFR1, VEGFR2, VEGFR3, membrane-bound VEGF-receptor (mbVEGFR), or soluble VEGF receptor (sVEGFR)); ST-2 receptor; and a protein genetically linked to age-related macular degeneration (AMD) risk (e.g., complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC; COL10A1; and TNFRSF10A). Such antibodies can be useful, for example, for reducing angiogenesis and/or for treating or delaying the progression of a disorder associated with pathological angiogenesis (e.g., ocular disorders). Exemplary, non-limiting anti-VEGF antibodies that can be used in the antibody conjugates of the invention are described further below.

In some instances, the anti-VEGF antibody may include at least one, two, three, four, five, or six HVRs selected from: (a) an HVR-H1 comprising the amino acid sequence of DYWIH (SEQ ID NO: 1); (b) an HVR-H2 comprising the amino acid sequence of $GX_1TPX_2GGX_3X_4X_5YX_6DSVX_7X_8$ (SEQ ID NO: 2), wherein $X_1$ is Ile or His, $X_2$ is Ala or Arg, $X_3$ is Tyr or Lys, $X_4$ is Thr or Glu, $X_5$ is Arg, Tyr, Gln, or Glu, $X_6$ is Ala or Glu, $X_7$ is Lys or Glu, and $X_8$ is Gly or Glu; (c) an HVR-H3 comprising the amino acid sequence of FVFFLPYAMDY (SEQ ID NO: 3); (d) an HVR-L1 comprising the amino acid sequence of $RASQX_1VSTAVA$ (SEQ ID NO: 4), wherein $X_1$ is Asp or Arg; (e) an HVR-L2 comprising the amino acid sequence of $X_1ASFLYS$ (SEQ ID NO: 5), wherein $X_1$ is Ser or Met; and (f) an HVR-L3 comprising the amino acid sequence of $X_1QGYGX_2PFT$ (SEQ ID NO: 6), wherein $X_1$ is Gln, Asn, or Thr and $X_2$ is Ala, Asn, Gln, or Arg, or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1-6.

For instance, the anti-VEGF antibody may include at least one, two, three, four, five, or six HVRs selected from: (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7), GITPAGGYEYYADSVKG (SEQ ID NO: 21), or GITPAG-GYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10) or QQGYGNPFT (SEQ ID NO: 23), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1, 3, 7-10, or 21-23.

For example, in some instances, the anti-VEGF antibody may include at least one, two, three, four, five, or six HVRs selected from: (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1, 3, or 7-10. In a particular example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10).

In some instances, any of the preceding anti-VEGF antibodies may include one, two, three, or four of the following heavy chain variable domain framework regions (FRs): (a) an FR-H1 comprising the amino acid sequence of EVQLVESGGGLVQPGGSLRLSCAASGFTIS (SEQ ID NO: 13); (b) an FR-H2 comprising the amino acid sequence of WVRQAPGKGLEWVA (SEQ ID NO: 14); (c) an FR-H3 comprising the amino acid sequence of RFTISADTSKNTAYLQMRSLRAEDTAVYYCAR (SEQ ID NO: 15); and (d) an FR-H4 comprising the amino acid sequence of WGQGTLVTVSS (SEQ ID NO: 16).

In some instances, any of the preceding anti-VEGF antibodies may include one, two, three, or four of the following light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20).

For example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EVQLVESGGGLVQPGGSLRLSCAASGFTIS (SEQ ID NO: 13); (b) an FR-H2 comprising the amino acid sequence of WVRQAPGKGLEWVA (SEQ ID NO: 14); (c) an FR-H3 comprising the amino acid sequence of RFTISADTSKNTAYLQMRSLRAEDTAVYYCAR (SEQ ID NO: 15); and (d) an FR-H4 comprising the amino acid sequence of WGQGTLVTVSS (SEQ ID NO: 16). In further instances, the anti-VEGF antibody includes the following four light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 11 and (b) a VL domain comprising an amino acid sequence of SEQ ID NO: 12.

For example, in some instances, the anti-VEGF antibody may include at least one, two, three, four, five, or six HVRs selected from: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGNPFT (SEQ ID NO: 23), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1, 3, 8, 9, 22, or 23. In a particular example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGNPFT (SEQ ID NO: 23).

In some instances, any of the preceding anti-VEGF antibodies may include one, two, three, or four of the following heavy chain variable domain framework regions (FRs): (a) an FR-H1 comprising the amino acid sequence of EEQLVEEGGGLVQPGESLELSCAASGFEIS (SEQ ID NO: 29) or EEQLVEEGGGLVQPGESLRLSCAASGFEIS (SEQ ID NO: 52); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32).

In some instances, any of the preceding anti-VEGF antibodies may include one, two, three, or four of the following light chain variable domain FRs: (a) an FR-L1 comprising the amino acid sequence of DIQMTQSPSSL-SASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDFA-TYYC (SEQ ID NO: 24); and (d) an FR-L4 comprising the amino acid sequence of FGQGTKVEIK (SEQ ID NO: 20).

For example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVF-FLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGNPFT (SEQ ID NO: 23). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSEN-TAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDFATYYC (SEQ ID NO: 24); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 38.

In some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYY-ADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGNPFT (SEQ ID NO: 23). In some instances, the anti-VEGF antibody includes the following four heavy chain variable domain FRs: (a) an FR-H1 comprising the amino acid sequence of EEQLVEEGGGLVQPGESLRLSCAASG-FEIS (SEQ ID NO: 52); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSL-SASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDFA-TYYC (SEQ ID NO: 24); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 51 and (b) a VL domain comprising an amino acid sequence of SEQ ID NO: 38.

For example, in some instances, the anti-VEGF antibody may include at least one, two, three, four, five, or six HVRs selected from: (a) an HVR-H1 comprising the amino acid sequence of DYWIH (SEQ ID NO: 1); (b) an HVR-H2 comprising the amino acid sequence of GITPAGGYEYY-ADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 1, 3, 8-10, or 22. In a particular example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVF-FLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10).

In some instances, any of the preceding anti-VEGF antibodies may include one, two, three, or four of the following heavy chain variable domain framework regions (FRs): (a) an FR-H1 comprising the amino acid sequence of EEQLVEEGGGLVQPGESLELSCAASGFEIS (SEQ ID NO: 29) or EEQLVEEGGGLVQPGESLRLSCAASGFEIS (SEQ ID NO: 52); (b) an FR-H2 comprising the amino acid sequence of WVRQEPGEGLEWVA (SEQ ID NO: 30); (c) an FR-H3 comprising the amino acid sequence of RFTI-SADTSENTAYLQMNELRAEDTAVYYCAR (SEQ ID NO: 31); and (d) an FR-H4 comprising the amino acid sequence of WGQGELVTVSS (SEQ ID NO: 32).

In some instances, any of the preceding anti-VEGF antibodies may include one, two, three, or four of the following light chain variable domain FRs: (a) an FR-L1 comprising the amino acid sequence of DIQMTQSPSSL-SASVGDRVTITC (SEQ ID NO: 17), DIQMTQSPESL-SASVGDEVTITC (SEQ ID NO: 25), or DIQMTQSPSSL-SASVGDEVTITC (SEQ ID NO: 26); (b) an FR-L2 comprising the amino acid sequence of WYQQKPGKAPKLLIY (SEQ ID NO: 18) or WYQQKPGEAPKLLIY (SEQ ID NO: 27); (c) an FR-L3 comprising the amino acid sequence of GVPSRFSGSGSGTDFTLTISSLQPEDAATYYC (SEQ ID NO: 19) or GVPSRFSGSGSGTDFTLTIESLQPED- AATYYC (SEQ ID NO: 28); and (d) an FR-L4 comprising the amino acid sequence of FGQGTKVEIK (SEQ ID NO: 20).

For example, in some instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVF-FLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSEN-TAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPESLSASVGDEVTITC (SEQ ID NO: 25); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 34.

For example, in other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVF-FLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSEN-TAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDEVTITC (SEQ ID NO: 26); (b) an FR-L2 comprising the amino acid sequence of WYQQKPGEAPKLLIY (SEQ ID NO: 27); (c) an FR-L3 comprising the amino acid sequence of GVPSRFSGSGSGTDFTLTIESLQPEDAATYYC (SEQ ID NO: 28); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 35.

For example, in other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVF-FLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLRLSCAASGFEIS (SEQ ID NO: 52); (b) an FR-H2 comprising the amino acid sequence of WVRQEPGEGLEWVA (SEQ ID NO: 30); (c) an FR-H3 comprising the amino acid sequence of RFTISADTSEN-TAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDEVTITC (SEQ ID NO: 26); (b) an FR-L2 comprising the amino acid sequence of WYQQKPGEAPKLLIY (SEQ ID NO: 27); (c) an FR-L3 comprising the amino acid sequence of GVPSRFSGSGSGTDFTLTIESLQPEDAATYYC (SEQ ID NO: 28); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 51 and (b) a VL domain comprising an amino acid sequence of SEQ ID NO: 35.

For example, in yet other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVF-FLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSEN-TAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPESLSASVGDEVTITC (SEQ ID NO: 25); (b) an FR-L2 comprising the amino acid sequence of WYQQKPGEAPKLLIY (SEQ ID NO: 27); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 36.

For example, in still further instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDEVTITC (SEQ ID NO: 26); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 37.

In other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLRLSCAASGFEIS (SEQ ID NO: 52); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDEVTITC (SEQ ID NO: 26); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 51 and (b) a VL domain comprising an amino acid sequence of SEQ ID NO: 37.

For example, in other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLELSCAASGFEIS (SEQ ID NO: 29); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 33 and (b) a VL domain comprising an amino acid sequence of SEQ ID NO: 12.

In other instances, the anti-VEGF antibody includes the following six HVRs: (a) an HVR-H1 comprising the amino acid sequence of DYWIH (SEQ ID NO: 1); (b) an HVR-H2 comprising the amino acid sequence of GITPAGGYEYYADSVEG (SEQ ID NO: 22); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following four heavy chain variable domain FRs: (a) an FR-H1 comprising the amino acid sequence of EEQLVEEGGGLVQPGESLRLSCAASGFEIS (SEQ ID NO: 52); (b) an FR-H2 comprising the amino acid sequence of WVRQEPGEGLEWVA (SEQ ID NO: 30); (c) an FR-H3 comprising the amino acid sequence of RFTISADTSENTAYLQMNELRAEDTAVYYCAR (SEQ ID NO: 31); and (d) an FR-H4 comprising the amino acid sequence of WGQGELVTVSS (SEQ ID NO: 32). In further instances, the anti-VEGF antibody includes the following four light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes (a) a VH domain comprising an amino acid sequence of SEQ ID NO: 51 and (b) a VL domain comprising an amino acid sequence of SEQ ID NO: 12.

In some instances, the anti-VEGF antibody comprises (a) a heavy chain variable (VH) domain comprising an amino acid sequence having at least 90% sequence identity (e.g., at least 91%, 92%, 93%, 94%, 95%, 96%, 97%, 98%, or 99% sequence identity) to, or the sequence of, any one of SEQ ID NOs: 11, 40, or 42; (b) a light chain variable (VL) domain comprising an amino acid sequence having at least 90% sequence (e.g., at least 91%, 92%, 93%, 94%, 95%, 96%, 97%, 98%, or 99% sequence identity) to, or the sequence of, any one of SEQ ID NOs: 12, 41, or 46; or (c) a VH domain as in (a) and a VL domain as in (b). For example, in some instances, the antibody comprises a VH domain comprising the amino acid sequence of SEQ ID NO: 11 and a VL domain comprising the amino acid sequence of SEQ ID NO: 12. In some instances, the antibody comprises a VH domain comprising the amino acid sequence of SEQ ID NO: 40 and a VL domain comprising the amino acid sequence of SEQ ID NO: 12. In some instances, the antibody comprises a VH domain comprising the amino acid sequence of SEQ ID NO: 42 and a VL domain comprising the amino acid sequence of SEQ ID NO: 12. In some instances, the antibody comprises a VH domain comprising the amino acid sequence of SEQ ID NO: 42 and a VL domain comprising the amino acid sequence of SEQ ID NO: 41. In some instances, the antibody comprises a VH domain comprising the amino acid sequence of SEQ ID NO: 11 and a VL domain comprising the amino acid sequence of SEQ ID NO: 46.

In some instances, any of the preceding anti-VEGF antibodies may include one, two, three, or four of the following heavy chain variable domain framework regions (FRs): (a) an FR-H1 comprising the amino acid sequence of EVQLVESGGGLVQPGGSLRLSCAASGFTIS (SEQ ID NO: 13); (b) an FR-H2 comprising the amino acid sequence of WVRQAPGKGLEWVA (SEQ ID NO: 14) or WVRQEPGKGLEWVA (SEQ ID NO: 39); (c) an FR-H3 comprising the amino acid sequence of RFTISADTSKNTAYLQMRSLRAEDTAVYYCAR (SEQ ID NO: 15); and (d) an FR-H4 comprising the amino acid sequence of WGQGTLVTVSS (SEQ ID NO: 16).

In some instances, any of the preceding anti-VEGF antibodies may include one, two, three, or four of the following light chain variable domain FRs: (a) an FR-L1 comprising the amino acid sequence of DIQMTQSPSSLSASVGDRVTITC (SEQ ID NO: 17) or DIQMTQSPSSLSASVGDRVTIDC (SEQ ID NO: 45); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19), GVPSRFSGSGSGTDFTLTISSLQPEDSATYYC (SEQ ID NO: 44), or GVPSRFSGSGSGTDFTLTISSLQPEDVATYYC (SEQ ID NO: 54); and (d) an FR-L4 comprising the amino acid sequence of FGQGTKVEIK (SEQ ID NO: 20) or FGQGTKVEVK (SEQ ID NO: 55).

In some instances, the antibody comprises a VH domain comprising the amino acid sequence of SEQ ID NO: 11 and a VL domain comprising the amino acid sequence of

```
                                            (SEQ ID NO: 59)
DIQMTQSPSSLSASVGDRVTITCRASQDVSTAVAWYQQKPGKAPKLLIYS

ASFLYSGVPSRFSGSGSGTDFTLTISSLQPEDVATYYCQQGYGNPFTFGQ

GTKVEIK.
```

In some instances, the antibody comprises a VH domain comprising the amino acid sequence of SEQ ID NO: 33 and a VL domain comprising the amino acid sequence of

```
                                            (SEQ ID NO: 59)
DIQMTQSPSSLSASVGDRVTITCRASQDVSTAVAWYQQKPGKAPKLLIYS

ASFLYSGVPSRFSGSGSGTDFTLTISSLQPEDVATYYCQQGYGNPFTFGQ

GTKVEIK.
```

In some instances, the antibody comprises a VH domain comprising the amino acid sequence of SEQ ID NO: 40 and a VL domain comprising the amino acid sequence of

```
                                            (SEQ ID NO: 59)
DIQMTQSPSSLSASVGDRVTITCRASQDVSTAVAWYQQKPGKAPKLLIYS

ASFLYSGVPSRFSGSGSGTDFTLTISSLQPEDVATYYCQQGYGNPFTFGQ

GTKVEIK.
```

In some instances, the antibody comprises a VH domain comprising the amino acid sequence of SEQ ID NO: 42 and a VL domain comprising the amino acid sequence of

```
                                            (SEQ ID NO: 59)
DIQMTQSPSSLSASVGDRVTITCRASQDVSTAVAWYQQKPGKAPKLLIYS

ASFLYSGVPSRFSGSGSGTDFTLTISSLQPEDVATYYCQQGYGNPFTFGQ

GTKVEIK.
```

In some instances, the antibody comprises a VH domain comprising the amino acid sequence of SEQ ID NO: 51 and a VL domain comprising the amino acid sequence of

```
                                            (SEQ ID NO: 59)
DIQMTQSPSSLSASVGDRVTITCRASQDVSTAVAWYQQKPGKAPKLLIYS

ASFLYSGVPSRFSGSGSGTDFTLTISSLQPEDVATYYCQQGYGNPFTFGQ

GTKVEIK.
```

In some instances, the antibody comprises a VH domain comprising the amino acid sequence of SEQ ID NO: 11 and a VL domain comprising the amino acid sequence of

```
                                            (SEQ ID NO: 60)
DIQMTQSPSSLSASVGDRVTITCRASQDVSTAVAWYQQKPGKAPKLLIYS

ASFLYSGVPSRFSGSGSGTDFTLTISSLQPEDVATYYCQQGYGAPFTFGQ

GTKVEIK.
```

In some instances, the antibody comprises a VH domain comprising the amino acid sequence of SEQ ID NO: 33 and a VL domain comprising the amino acid sequence of

```
                                          (SEQ ID NO: 60)
DIQMTQSPSSLSASVGDRVTITCRASQDVSTAVAWYQQKPGKAPKLLIYS

ASFLYSGVPSRFSGSGSGTDFTLTISSLQPEDVATYYCQQGYGAPFTFGQ

GTKVEIK.
```

In some instances, the antibody comprises a VH domain comprising the amino acid sequence of SEQ ID NO: 40 and a VL domain comprising the amino acid sequence of

```
                                          (SEQ ID NO: 60)
DIQMTQSPSSLSASVGDRVTITCRASQDVSTAVAWYQQKPGKAPKLLIYS

ASFLYSGVPSRFSGSGSGTDFTLTISSLQPEDVATYYCQQGYGAPFTFGQ

GTKVEIK.
```

In some instances, the antibody comprises a VH domain comprising the amino acid sequence of SEQ ID NO: 42 and a VL domain comprising the amino acid sequence of

```
                                          (SEQ ID NO: 60)
DIQMTQSPSSLSASVGDRVTITCRASQDVSTAVAWYQQKPGKAPKLLIYS

ASFLYSGVPSRFSGSGSGTDFTLTISSLQPEDVATYYCQQGYGAPFTFGQ

GTKVEIK.
```

In some instances, the antibody comprises a VH domain comprising the amino acid sequence of SEQ ID NO: 51 and a VL domain comprising the amino acid sequence of

```
                                          (SEQ ID NO: 60)
DIQMTQSPSSLSASVGDRVTITCRASQDVSTAVAWYQQKPGKAPKLLIYS

ASFLYSGVPSRFSGSGSGTDFTLTISSLQPEDVATYYCQQGYGAPFTFGQ

GTKVEIK.
```

For example, in some instances, the anti-VEGF antibody comprises (a) a VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 11; (b) a VL domain comprising an amino acid sequence having at least 90% sequence (e.g., at least 91%, 92%, 93%, 94%, 95%, 96%, 97%, 98%, or 99% sequence identity) to, or the sequence of, SEQ ID NO: 11; or (c) a VH domain as in (a) and a VL domain as in (b). In some instances, the anti-VEGF antibody may include (a) an HVR-H1 comprising the amino acid sequence of DYWIH (SEQ ID NO: 1); (b) an HVR-H2 comprising the amino acid sequence of GITPAGGYTRYADSVKG (SEQ ID NO: 7); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the anti-VEGF antibody includes the following heavy chain framework regions: (a) an FR-H1 comprising the amino acid sequence of EVQLVESGGGLVQPGGSLRLSCAASGFTIS (SEQ ID NO: 13); (b) an FR-H2 comprising the amino acid sequence of WVRQAPGKGLEWVA (SEQ ID NO: 14); (c) an FR-H3 comprising the amino acid sequence of RFTISADTSKNTAYLQMRSLRAEDTAVYYCAR (SEQ ID NO: 15); and (d) an FR-H4 comprising the amino acid sequence of WGQGTLVTVSS (SEQ ID NO: 16). In some instances, the anti-VEGF antibody includes the following light chain framework regions: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the anti-VEGF antibody includes a binding domain comprising (a) a VH domain comprising an amino acid sequence of SEQ ID NO: 11 and (b) a VL domain comprising an amino acid sequence of SEQ ID NO: 12. In some instances, the exemplary anti-VEGF is N94A.F83A.N82aR.Y58R (also referred to as G6.31 AARR or G6.31.AARR).

In some instances, the anti-VEGF antibody comprises (a) VH domain comprising an amino acid sequence having at least 90% sequence identity (e.g., at least 91%, 92%, 93%, 94%, 95%, 96%, 97%, 98%, or 99% sequence identity) to, or the sequence of, SEQ ID NO: 33 or 51; (b) a VL domain comprising an amino acid sequence having at least 90% sequence (e.g., at least 91%, 92%, 93%, 94%, 95%, 96%, 97%, 98%, or 99% sequence identity) to, or the sequence of, any one of SEQ ID NOs: 12, 34, 35, 36, 37, or 38; or (c) a VH domain as in (a) and a VL domain as in (b). For example, in some instances, the antibody comprises a VH domain comprising the amino acid sequence of SEQ ID NO: 33 and a VL domain comprising the amino acid sequence of SEQ ID NO: 12. In some instances, the antibody comprises a VH domain comprising the amino acid sequence of SEQ ID NO: 33 and a VL domain comprising the amino acid sequence of SEQ ID NO: 34. In some instances, the antibody comprises a VH domain comprising the amino acid sequence of SEQ ID NO: 33 and a VL domain comprising the amino acid sequence of SEQ ID NO: 35. In some instances, the antibody comprises a VH domain comprising the amino acid sequence of SEQ ID NO: 33 and a VL domain comprising the amino acid sequence of SEQ ID NO: 36. In some instances, the antibody comprises a VH domain comprising the amino acid sequence of SEQ ID NO: 33 and a VL domain comprising the amino acid sequence of SEQ ID NO: 37. In some instances, the antibody comprises a VH domain comprising the amino acid sequence of SEQ ID NO: 33 and a VL domain comprising the amino acid sequence of SEQ ID NO: 38. In some instances, the antibody comprises a VH domain comprising the amino acid sequence of SEQ ID NO: 51 and a VL domain comprising the amino acid sequence of SEQ ID NO: 38. In some instances, the antibody comprises a VH domain comprising the amino acid sequence of SEQ ID NO: 51 and a VL domain comprising the amino acid sequence of SEQ ID NO: 35. In some instances, the antibody comprises a VH domain comprising the amino acid sequence of SEQ ID NO: 51 and a VL domain comprising the amino acid sequence of SEQ ID NO: 37. In some instances, the antibody comprises a VH domain comprising the amino acid sequence of SEQ ID NO: 51 and a VL domain comprising the amino acid sequence of SEQ ID NO: 12.

In some instances, any of the preceding anti-VEGF antibodies may include one, two, three, or four of the following heavy chain variable domain framework regions (FRs): an FR-H1 comprising the amino acid sequence of EEQLVEEGGGLVQPGESLELSCAASGFEIS (SEQ ID NO: 29) or EEQLVEEGGGLVQPGESLRLSCAASGFEIS (SEQ ID NO: 52); (b) an FR-H2 comprising the amino acid sequence of WVRQEPGEGLEWVA (SEQ ID NO: 30) or WVRQEPGKGLEWVA (SEQ ID NO: 39); (c) an FR-H3 comprising the amino acid sequence of RFTISADTSEN-TAYLQMNELRAEDTAVYYCAR (SEQ ID NO: 31); and (d) an FR-H4 comprising the amino acid sequence of WGQGELVTVSS (SEQ ID NO: 32).

In some instances, any of the preceding anti-VEGF antibodies may include one, two, three, or four of the following light chain variable domain FRs: (a) an FR-L1 comprising the amino acid sequence of DIQMTQSPSSL-SASVGDRVTITC (SEQ ID NO: 17), DIQMTQSPESL-SASVGDEVTITC (SEQ ID NO: 25), or DIQMTQSPSSL-SASVGDEVTITC (SEQ ID NO: 26); (b) an FR-L2 comprising the amino acid sequence of WYQQKPGKAPKLLIY (SEQ ID NO: 18) or WYQQKPGEAPKLLIY (SEQ ID NO: 27); (c) an FR-L3 comprising the amino acid sequence of GVPSRFSGSGSGTDFTLTISSLQPEDAATYYC (SEQ ID NO: 19), GVPSRFSGSGSGTDFTLTISSLQPEDFATYYC (SEQ ID NO: 24), or GVPSRFSGSGSGTDFTLTIES-LQPEDAATYYC (SEQ ID NO: 28); and (d) an FR-L4 comprising the amino acid sequence of FGQGTKVEIK (SEQ ID NO: 20).

In some instances, the invention provides an antibody comprising (a) a heavy chain comprising the amino acid sequence of SEQ ID NO: 48 and/or (b) a light chain comprising the amino acid sequence of SEQ ID NO: 50. In certain embodiments, the antibody is G6.31 AARR expressed in Fab format.

In some instances, the invention provides an antibody comprising (a) a heavy chain comprising the amino acid sequence of SEQ ID NO: 49 and/or (b) a light chain comprising the amino acid sequence of SEQ ID NO: 50. In certain embodiments, the antibody is a variant version of G6.31 AARR that lacks reactivity to anti-human IgG.

In a further aspect, an antibody (e.g., an anti-VEGF antibody) according to any of the above embodiments may incorporate any of the features, singly or in combination, as described in Sections 1-8 below:

1. Antibody Affinity

In certain embodiments, an antibody provided herein has a dissociation constant (Kd) of ≤1 μM, ≤100 nM, ≤10 nM, ≤1 nM, ≤0.1 nM, ≤0.01 nM, or ≤0.001 nM (e.g., $10^{-9}$ M or less, e.g., from $10^{-9}$ M to $10^{-13}$ M, e.g., from $10^{-9}$ M to $10^{-13}$ M). For example, in some instances, an antibody provided herein binds an antigen (e.g., human VEGF (hVEGF)) with a Kd of about 10 nM or lower. In some instances, an antibody provided herein binds an antigen (e.g., hVEGF) with a Kd of about 5 nM or lower. In some instances, an antibody provided herein binds hVEGF with a Kd of about 2 nM or lower. For example, in some instances, the antibody binds an antigen (e.g., hVEGF) with a Kd between about 25 pM and about 2 nM (e.g., about 25 pM, about 50 pM, about 75 pM, about 100 pM, about 125 pM, about 150 pM, about 175 pM, about 200 pM, about 225 pM, about 250 pM, about 275 pM, about 300 pM, about 325 pM, about 350 pM, about 375 pM, about 400 pM, about 425 pM, about 450 pM, about 475 pM, about 500 pM, about 525 pM, about 550 pM, about 575 pM, about 600 pM, about 625 pM, about 650 pM, about 675 pM, about 700 pM, about 725 pM, about 750 pM, about 775 pM, about 800 pM, about 825 pM, about 850 pM, about 875 pM, about 900 pM, about 925 pM, about 950 pM, about 975 pM, about 1 nM, about 1.1 nM, about 1.2 nM, about 1.3 nM, about 1.4 nM, about 1.5 nM, about 1.6 nM, about 1.7 nM, about 1.8 nM, about 1.9 nM, or about 2 nM). In some instances, the antibody binds an antigen (e.g., hVEGF) with a Kd between about 75 pM and about 600 pM (e.g., about 75 pM, about 100 pM, about 125 pM, about 150 pM, about 175 pM, about 200 pM, about 225 pM, about 250 pM, about 275 pM, about 300 pM, about 325 pM, about 350 pM, about 375 pM, about 400 pM, about 425 pM, about 450 pM, about 475 pM, about 500 pM, about 525 pM, about 550 pM, about 575 pM, about 600 pM). In some instances, the antibody binds an antigen (e.g., hVEGF) with a Kd between about 75 pM and about 500 pM. In some instances, the antibody binds an antigen (e.g., hVEGF) with a Kd between about 75 pM and about 400 pM. In some instances, the antibody binds an antigen (e.g., hVEGF) with a Kd between about 75 pM and about 300 pM. In some instances, the antibody binds an antigen (e.g., hVEGF) with a Kd between about 75 pM and about 200 pM. In some instances, the antibody binds an antigen (e.g., hVEGF) with a Kd between about 75 pM and about 150 pM. In some instances, the antibody binds an antigen (e.g., hVEGF) with a Kd between about 75 pM and about 125 pM. In some instances, the antibody binds an antigen (e.g., hVEGF) with a Kd between about 75 pM and about 100 pM. In some instances, the antibody binds an antigen (e.g., hVEGF) with a Kd of about 80 pM. In some instances, the antibody binds an antigen (e.g., hVEGF) with a Kd of about 60 pM. In some instances, the antibody binds an antigen (e.g., hVEGF) with a Kd of about 40 pM.

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 μg/ml of a capturing anti-Fab antibody (Cappel Labs) in 50 mM sodium carbonate (pH 9.6), and subsequently blocked with 2% (w/v) bovine serum albumin (BSA) in phosphate buffered saline (PBS) for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 μl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIA-CORE®-3000 (BIAcore, Inc., Piscataway, NJ) is performed at 25° C. with immobilized antigen CM5 chips at ~10 response units (RU). In one embodiment, carboxymethylated dextran biosensor chips (CM5, BIAcore, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, for example, Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Stability

In some instances, the antibody used in the antibody conjugates of the invention or compositions thereof have enhanced stability, for example, as compared to an anti-VEGF antibody, for instance, G6.31 (see, e.g., U.S. Pat. No. 7,758,859 and International Application Pub. No. WO 2005/012359, which are incorporated herein by reference in their entirety). The stability of an antibody may be determined using any method known in the art, for example, differential scanning fluorimetry (DSF), circular dichroism (CD), intrinsic protein fluorescence, differential scanning calorimetry, spectroscopy, light scattering (e.g., dynamic light scattering (DLS) and static light scattering (SLS), self-interaction chromatography (SIC). The anti-VEGF antibody may have, for example, an enhanced melting temperature ($T_m$), temperature of aggregation ($T_{agg}$), or other metrics of stability compared to an anti-VEGF antibody, for example, G6.31.

In certain embodiments, an antibody provided herein has a $T_m$ that is greater than or equal to about 80° C. (e.g., about 81° C., about 82° C., about 83° C., about 84° C., about 85° C., about 86° C., about 87° C., about 88° C., about 89° C., about 90° C., about 91° C., about 92° C., or about 93° C.). For example, in some instances, the anti-VEGF antibody has a $T_m$ that is greater than or equal to about 83.5° C. (e.g., about 83.5° C., about 84° C., about 85° C., about 86° C., about 87° C., about 88° C., about 89° C., about 90° C., about 91° C., about 92° C., or about 93° C.). In some instances, the anti-VEGF antibody has a $T_m$ of about 82° C. to about 92° C. (e.g., about 82° C., about 83° C., about 84° C., about 85° C., about 86° C., about 87° C., about 88° C., about 89° C., about 90° C., about 91° C., or about 92° C.). In some about instances, the anti-VEGF antibody has a $T_m$ of about 82° C. In some instances, any of the preceding $T_m$ values of an anti-VEGF antibody is determined using DSF. In some embodiments, the $T_m$ value of an anti-VEGF antibody is determined as described, for example, in Example 1 of International Patent Application No. PCT/US2016/053454, which is incorporated herein by reference in its entirety.

3. Antibody Fragments

In certain embodiments, an antibody provided herein is an antibody fragment. Antibody fragments include, but are not limited to, Fab, Fab', Fab-C, Fab'-SH, F(ab')$_2$, Fv, and scFv fragments, and other fragments described below. For a review of certain antibody fragments, see Hudson et al., *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, MA; see, e.g., U.S. Pat. No. 6,248,516 B1).

Antibody fragments can be made by various techniques, including but not limited to proteolytic digestion of an intact antibody as well as production by recombinant host cells (e.g., *E. coli* or phage), as described herein.

4. Chimeric and Humanized Antibodies

In certain embodiments, an antibody provided herein is a chimeric antibody. Certain chimeric antibodies are described, for example, in U.S. Pat. No. 4,816,567; and Morrison et al., *Proc. Natl. Acad. Sci. USA*, 81:6851-6855 (1984). In one example, a chimeric antibody comprises a non-human variable region (e.g., a variable domain derived from a mouse, rat, hamster, rabbit, or non-human primate, such as a monkey) and a human constant domain. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, for example, CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, for example, in Almagro and Fransson, *Front. Biosci.* 13:1619-1633 (2008), and are further described, for example, in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al., *J. Immunol.* 151:2296 (1993)); framework regions derived from the consensus sequence of human antibodies of a particular subgroup of light or heavy chain variable regions (see, e.g., Carter et al., *Proc. Natl. Acad. Sci. USA,* 89:4285 (1992); and Presta et al., *J. Immunol,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

5. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, for example, by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

6. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al., in *Methods in Molecular Biology* 178: 1-37 (O'Brien et al., ed., Human Press, Totowa, NJ, 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, NJ, 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments can be derived from phage libraries as described in International Patent Application No. PCT/US2016/053454.

Antibodies or antibody fragments isolated from human antibody libraries are considered human antibodies or human antibody fragments herein.

7. Multispecific Antibodies

In certain embodiments, an antibody provided herein is a multispecific antibody, for example, a bispecific antibody. Multispecific antibodies are monoclonal antibodies that have binding specificities for at least two different sites. In certain embodiments, one of the binding specificities is for VEGF and the other is for any other antigen (e.g., a second biological molecule, e.g., interleukin-1 beta (IL-1β); interleukin-6 (IL-6); interleukin-6 receptor (IL-6R); interleukin-13 (IL-13); IL-13 receptor (IL-13R); PDGF (e.g., PDGF-BB); angiopoietin; angiopoietin 2 (Ang2); Tie2; S1P; integrins αvβ3, αvβ5, and α5β1; betacellulin; apelin/APJ;

erythropoietin; complement factor D; TNFα; HtrA1; a VEGF receptor (e.g., VEGFR1, VEGFR2, VEGFR3, membrane-bound VEGF-receptor (mbVEGFR), or soluble VEGF receptor (sVEGFR)); ST-2 receptor; and proteins genetically linked to age-related macular degeneration (AMD) risk, such as complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC; COL10A1; and TNFRSF10A. Accordingly, the bispecific antibody may have binding specificity for VEGF and IL-1β; VEGF and IL-6; VEGF and IL-6R; VEGF and IL-13; VEGF and IL-13R; VEGF and PDGF (e.g., PDGF-BB); VEGF and angiopoietin; VEGF and Ang2; VEGF and Tie2; VEGF and S1P; VEGF and integrin αvβ3; VEGF and integrin αvβ5; VEGF and integrin α5β1; VEGF and betacellulin; VEGF and apelin/APJ; VEGF and erythropoietin; VEGF and complement factor D; VEGF and TNFα; VEGF and HtrA1; VEGF and a VEGF receptor (e.g., VEGFR1, VEGFR2, VEGFR3, mbVEGFR, or sVEGFR); VEGF and ST-2 receptor; VEGF and C2; VEGF and factor B; VEGF and factor H; VEGF and CFHR3; VEGF and C3b; VEGF and C5; VEGF and C5a; VEGF and C3a; VEGF and ARMS2; VEGF and TIMP3; VEGF and HLA; VEGF and IL-8; VEGF and CX3CR1; VEGF and TLR3; VEGF and TLR4; VEGF and CETP; VEGF and LIPC; VEGF and COL10A1; or VEGF and TNFRSF10A. In certain embodiments, bispecific antibodies may bind to two different epitopes of VEGF. Bispecific antibodies may also be used to localize cytotoxic agents to cells which express VEGF. Bispecific antibodies can be prepared as full length antibodies or antibody fragments (e.g., Fab, Fab', or Fab-C fragments).

In some instances, the bispecific antibody is a bispecific anti-VEGF/anti-angiopoeitin 2 (Ang2) antibody disclosed in U.S. Patent Application No. US 2014/0017244, which is incorporated herein by reference in its entirety. For example, the anti-VEGF/anti-Ang2 bispecific antibody may include a first binding domain that binds VEGF (such as any of the anti-VEGF antibodies described herein) and a second binding domain that binds Ang2 that includes (a) an HVR-H1 comprising the amino acid sequence of GYYMH (SEQ ID NO: 62); (b) an HVR-H2 comprising the amino acid sequence of WINPNSGGTNYAQKFQG (SEQ ID NO: 63); (c) an HVR-H3 comprising the amino acid sequence of SPNPYYYDSSGYYYPGAFDI (SEQ ID NO: 64); (d) an HVR-L1 comprising the amino acid sequence of GGNNIG-SKSVH (SEQ ID NO: 65); (e) an HVR-L2 comprising the amino acid sequence of DDSDRPS (SEQ ID NO: 66); and (f) an HVR-L3 comprising the amino acid sequence of QVWDSSSDHWV (SEQ ID NO: 67), or a combination of one or more of the above HVRs and one or more variants thereof having at least about 80% sequence identity (e.g., 81%, 82%, 83%, 84%, 85%, 86%, 87%, 88%, 89%, 90%, 91%, 92%, 93%, 94%, 95%, 96%, 97%, 98%, or 99% identity) to any one of SEQ ID NOs: 62-67.

In some instances, the anti-VEGF/anti-Ang2 bispecific antibody may include a first binding domain that binds VEGF (such as any of the anti-VEGF antibodies described herein) and a second binding domain that binds to Ang2 and includes (a) a VH domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 68; (b) a VL domain comprising an amino acid sequence having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, or 99% sequence identity) to, or the sequence of, SEQ ID NO: 69; or (c) a VH domain as in (a) and a VL domain as in (b). In some instances, the anti-VEGF/anti-Ang2 bispecific antibody may include a first binding domain that binds VEGF (such as any of the anti-VEGF antibodies described herein) and a second binding domain that specifically bind to Ang2, wherein the second binding domain is any antibody binding domain described in International Patent Application Publication No. WO 2010/069532, which is incorporated herein by reference in its entirety, or a variant thereof.

In other instances, the anti-VEGF/anti-Ang2 bispecific antibody is any anti-VEGF/anti-Ang2 bispecific antibody described in International Patent Application Publication No. WO 2016/073157.

In some instances, the bispecific antibody is a bispecific anti-VEGF/anti-IL-6 antibody. In some instances, an anti-VEGF/anti-IL-6 bispecific antibody may include a first binding domain that binds VEGF (such as any of the anti-VEGF antibodies described herein) and a second binding domain that binds IL-6. The second binding domain may be a binding domain of any anti-IL-6 antibody known in the art, for example, EBI-031 (Eleven Biotherapeutics; see, e.g., WO 2016/073890, which is incorporated herein by reference in its entirety), siltuximab (SYLVANT®), olokizumab, clazakizumab, sirukumab, elsilimomab, gerilimzumab, OPR-003, MEDI-5117, PF-04236921, or a variant thereof.

In some instances, the bispecific antibody is a bispecific anti-VEGF/anti-IL-6R antibody. In some instances, an anti-VEGF/anti-IL-6R bispecific antibody may include a first binding domain that binds VEGF (such as any of the anti-VEGF antibodies described herein) and a second binding domain that binds IL-6R. The second binding domain may be a binding domain any anti-IL-6R antibody known in the art, for example, tocilizumab (ACTEMRA®) (see, e.g., WO 1992/019579, which is incorporated herein by reference in its entirety), sarilumab, vobarilizumab (ALX-0061), SA-237, or a variant thereof.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (see, e.g., Gruber et al., *J. Immunol.*, 152:5368 (1994)); and preparing trispecific antibodies as described, for example, in Tutt et al., *J. Immunol.* 147:60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to VEGF as well as another, different antigen (see, e.g., US 2008/0069820).

8. Antibody Variants

In certain embodiments, amino acid sequence variants (e.g., antibody variants including one or more amino acid residue alterations) of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, for example, antigen binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, for example, retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues and/or FR residues of a parent antibody (e.g., a humanized or human antibody). Generally, the resulting variant(s) selected for further study will have modifications (e.g., improvements) in certain biological properties (e.g., increased affinity, increased stability, increased expression, altered pI, and/or reduced immunogenicity) relative to the parent antibody and/or will have substantially retained certain biological properties of the parent antibody. An exemplary substitutional variant is an affinity matured antibody, which may be conveniently generated, for example, using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, for example, to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, for example, in Hoogenboom et al., in *Methods in Molecular Biology* 178:1-37 (O'Brien et al., ed., Human Press, Totowa, NJ, (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

In certain embodiments, substitutions, insertions, or deletions may occur within one or more FRs so long as such alterations do not substantially reduce the ability of the antibody to bind antigen. Such alterations may, for example, improve antibody affinity and/or stability (e.g., as assessed by an increased melting temperature).

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, for example, US Patent Publication Nos. US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al., J. Mol. Biol. 336:1239-1249 (2004); Yamane-Ohnuki et al., Biotech. Bioeng. 87: 614 (2004). Examples of cell lines capable of producing defucosylated antibodies include Led 3 CHO cells deficient in protein fucosylation (Ripka et al., *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al., *Biotech. Bioeng.* 87: 614 (2004); Kanda et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546 (Umana et al.). Antibody variants with at least one galactose residue in the oligosaccharide attached to the Fc region are also provided. Such antibody variants may have improved CDC function. Such antibody variants are described, for example, in WO 1997/30087; WO 1998/58964; and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid residue alteration (e.g., a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991).

Non-limiting examples of in vitro assays to assess ADCC activity of a molecule of interest are described in U.S. Pat. No. 5,500,362 (see, e.g. Hellstrom et al., *Proc. Nat'l Acad. Sci. USA* 83:7059-7063 (1986) and Hellstrom, I et al., *Proc. Nat'l Acad. Sci. USA* 82:1499-1502 (1985); U.S. Pat. No. 5,821,337; and Bruggemann et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CYTOTOX 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, for example, in an animal model such as that disclosed in Clynes et al., *Proc. Nat'l Acad. Sci. USA* 95:652-656 (1998). C1q binding assays may also be carried out to confirm that the antibody is unable to bind C1q and hence lacks CDC activity. See, for example, C1q and C3c binding ELISA in WO 2006/029879 and WO 2005/100402. To assess complement activation, a CDC assay may be performed (see, e.g., Gazzano-Santoro et al., *J. Immunol. Methods* 202:163 (1996); Cragg et al., *Blood* 101:1045-1052 (2003); and Cragg et al., *Blood* 103:2738-2743 (2004)). FcRn binding and in vivo clearance/half life determinations can also be performed using methods known in the art (see, e.g., Petkova et al., *Int'l. Immunol.* 18(12): 1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001)). In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), for example, as described in U.S. Pat. No. 6,194,551, WO 99/51642, and Idusogie et al., *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. Nos. 5,648,260; 5,624,821; and WO 94/29351 concerning other examples of Fc region variants.

d) Cysteine Engineered Antibody Variants

The invention provides cysteine engineered antibodies where one or more amino acids of a wild-type or parent antibody (e.g., an anti-VEGF antibody, including any anti-VEGF antibody described herein) are replaced (i.e., "substituted" or "mutated") with a cysteine amino acid (i.e., an "engineered cysteine"). Any form of antibody may be so engineered, i.e. mutated. For example, a parent monoclonal antibody may be engineered to form a "THIOMAB™ antibody." One example of a THIOMAB™ antibody is an antibody fragment (i.e., a Fab) that has an engineered cysteine. This Fab THIOMAB™ antibody can be referred to as "ThioFab." It should be noted that a single site mutation yields a single engineered cysteine residue in a ThioFab, while a single site mutation yields two engineered cysteine residues in a THIOMAB™ antibody, due to the dimeric nature of the IgG antibody.

Mutants with engineered cysteine (Cys) residues can be evaluated for the reactivity of the newly introduced, engineered cysteine thiol groups. The thiol reactivity value is a relative, numerical term in the range of 0 to 1.0 and can be measured for any cysteine engineered antibody. Thiol reactivity values of cysteine engineered antibodies of the invention are in the range of 0.0 to 1.0. Specifically, the thiol reactivity values of cysteine engineered antibodies of the invention are in the range of 0.1 to 1.0. In certain embodiments, the thiol reactivity values of cysteine engineered antibodies of the invention are in the ranges of 0.0 to 0.1, 0.1 to 0.5, 0.1 to 0.6, 0.1 to 0.7, 0.1 to 0.8, 0.1 to 0.9, or 0.1 to 1.0. In certain embodiments, the thiol reactivity values of cysteine engineered antibodies of the invention are in the ranges of 0.2 to 1.0, 0.3 to 1.0, 0.4 to 1.0, 0.5 to 1.0, 0.6 to 1.0, 0.7 to 1.0, or 0.8 to 1.0. In certain embodiments, the thiol reactivity values of cysteine engineered antibodies of the invention are in the range of 0.6 to 1.0. In certain embodiments, the thiol reactivity values of cysteine engineered antibodies of the invention are in the ranges of 0.7 to 1.0. In certain embodiments, the thiol reactivity values of cysteine engineered antibodies of the invention are in the ranges of 0.8 to 10. In certain embodiments, the thiol reactivity values of cysteine engineered antibodies of the invention are in the ranges of 0.5 to 0.8. In certain embodiments, the thiol reactivity values of cysteine engineered antibodies of the invention are in the ranges of 0.5 to 0.9. In certain embodiments, the thiol reactivity values of cysteine engineered antibodies of the invention are in the ranges of 0.5 to 0.7. In certain embodiments, the thiol reactivity values of cysteine engineered antibodies of the invention are in the ranges of 0.5 to 1.0.

The invention provides design, selection, and preparation methods for producing cysteine engineered antibodies which are reactive with electrophilic functionality. These methods further enable antibody conjugate compounds such as, for example, antibody-polymer conjugates with polymer moieties conjugated at designated, designed, selective sites. Reactive cysteine residues on an antibody surface allow specifically conjugating a polymer through a thiol reactive group such as maleimide or haloacetyl. The nucleophilic reactivity of the thiol functionality of a Cys residue to a maleimide group is about 1000 times higher compared to any other amino acid functionality in a protein, such as amino group of lysine residues or the N-terminal amino group. Thiol specific functionality in iodoacetyl and maleimide reagents may react with amine groups, but higher pH (>9.0) and longer reaction times are required (Garman, 1997, Non-Radioactive Labelling: A Practical Approach, Academic Press, London).

Cysteine engineered antibodies of the invention preferably retain the antigen binding capability of their wild type, parent antibody counterparts. Thus, cysteine engineered antibodies are capable of binding, preferably specifically, to antigens. Exemplary, non-limiting antigens include VEGF; IL-1β; IL-6; IL-6R; IL-13; IL-13R; PDGF (e.g., PDGF-BB); angiopoietin; angiopoietin 2 (Ang2); Tie2; S1P; integrins αvβ3, αvβ5, and α5β1; betacellulin; apelin/APJ; erythropoietin; complement factor D; TNFα; HtrA1; a VEGF receptor (e.g., VEGFR1, VEGFR2, VEGFR3, mbVEGFR, or sVEGFR); ST-2 receptor; and a protein genetically linked to AMD risk (e.g., complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC; COL10A1; and TNFRSF10A).

Any of the antibodies described herein (e.g., any of the anti-VEGF antibodies described above) may be a parent antibody used to generate a cysteine engineered antibody. The exemplary methods described here may be applied generally to the identification and production of antibodies through application of the design and screening steps described herein.

Cysteine engineered antibodies of the invention may be site-specifically and efficiently coupled with a thiol-reactive reagent. The thiol-reactive reagent may be, for example, a clearance-modifying agent such as a polymer (e.g., an HA polymer or various isomers of polyethylene glycol), a peptide that binds to a third component, or another carbohydrate or lipophilic agent, a multifunctional linker reagent, a capture, i.e., affinity, label reagent (e.g., a biotin-linker reagent), a detection label (e.g., a fluorophore reagent), a solid phase immobilization reagent (e.g., SEPHAROSE™, polystyrene, or glass), or a drug-linker intermediate. One example of a thiol-reactive reagent is N-ethyl maleimide (NEM). In an exemplary embodiment, reaction of a THIOMAB™ antibody with a biotin-linker reagent provides a biotinylated THIOMAB™ antibody by which the presence and reactivity of the engineered cysteine residue may be detected and measured. Reaction of a THIOMAB™ antibody with a multifunctional linker reagent provides a THIOMAB™ antibody with a functionalized linker which may be further reacted with a polymer, a drug moiety reagent, or other label. Reaction of a THIOMAB™ antibody with a drug-linker intermediate provides a THIOMAB™ antibody drug conjugate. In certain embodiments, the THIOMAB™ antibody is a ThioFab.

Cysteine engineered antibodies can be conjugated to thiol-reactive agents in which the reactive group is, for example, a maleimide, an iodoacetamide, a pyridyl disulfide, or other thiol-reactive conjugation partner (see, e.g., Haugland, 2003, Molecular Probes Handbook of Fluorescent Probes and Research Chemicals, Molecular Probes, Inc.; Brinkley, 1992, Bioconjugate Chem. 3:2; Garman, 1997, Non-Radioactive Labelling: A Practical Approach, Academic Press, London; Means (1990) Bioconjugate Chem. 1:2; Hermanson, G. in Bioconjugate Techniques (1996) Academic Press, San Diego, pp. 40-55, 643-671). The partner may be a cytotoxic agent (e.g., a toxin such as doxorubicin or pertussis toxin), a fluorophore such as a fluorescent dye like fluorescein or rhodamine, a chelating agent for an imaging or radiotherapeutic metal, a peptidyl or non-peptidyl label or detection tag, or a clearance-modifying agent such as a polymer (e.g., an HA polymer or various isomers of polyethylene glycol), a peptide that binds to a third component, or another carbohydrate or lipophilic agent.

The PHESELECTOR (Phage ELISA for Selection of Reactive Thiols) assay allows for detection of reactive cysteine groups in antibodies in an ELISA phage format. See U.S. Pat. No. 7,521,541 and U.S. Pat. Pub. No. 20110301334, which are incorporated herein by reference in their entirety. Specifically, the PHESESLECTOR assay includes the process of coating the protein (e.g., antibody) of interest on well surfaces, followed incubation with phage particles and then horseradish peroxidase (HRP) labeled secondary antibody with absorbance detection. Mutant proteins displayed on phage may be screened in a rapid, robust, and high-throughput manner. Libraries of cysteine engineered antibodies can be produced and subjected to binding selection using the same approach to identify appropriately reactive sites of free Cys incorporation from random protein-phage libraries of antibodies or other proteins. This technique includes reacting cysteine mutant proteins displayed on phage with an affinity reagent or reporter group which is also thiol-reactive.

In certain embodiments, the PHESELECTOR assay includes the following steps: (1) bovine serum albumin (BSA), a portion or entirety of a target protein (e.g., VEGF), and streptavidin (100 µl of 2 µg/ml) are separately coated on MAXISORB® 96 well plates; (2) After blocking with 0.5% TWEEN®-20 (in PBS), biotinylated and non-biotinylated THIOMAB™ antibody-phage ($2\times10^{10}$ phage particles) are incubated for 1 hour at room temperature; (3) the incubation with the phage is followed by incubation with HRP labeled secondary antibody (anti-M13 phage coat protein, pVIII protein antibody); (4) standard HRP reactions are carried out and the absorbance is measured at 450 nm; (5) thiol reactivity is measured by calculating the ratio between $OD_{450}$ for streptavidin/$OD_{450}$ for the target protein (e.g., VEGF) such that a thiol reactivity value of 1 indicates complete biotinylation of the cysteine thiol.

DNA encoding the cysteine engineered antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as E. coli cells, simian COS cells, Chinese Hamster Ovary (CHO) cells, HEK293T cells, or other mammalian host cells, such as myeloma cells (U.S. Pat. No. 5,807,715; US 2005/0048572; US 2004/0229310) that do not otherwise produce the antibody protein, to obtain the synthesis of monoclonal antibodies in the recombinant host cells. In most cases, the yields of the cysteine engineered antibodies are similar to wild type antibodies.

After design and selection, cysteine engineered antibodies, e.g., THIOMAB™ antibodies, with highly reactive unpaired Cys residues, may be produced by: (i) expression in a bacterial, e.g., E. coli, system or a mammalian cell culture system (WO 01/00245), e.g., Chinese Hamster Ovary cells (CHO) or HEK293 cells (e.g., HEK293T cells); and (ii) purification using common protein purification techniques (e.g., Lowman et al (1991) J. Biol. Chem. 266(17): 10982-10988). In specific embodiments, the THIOMAB™ antibodies are expressed in a mammalian cell expression system. In specific embodiments, the mammalian cell expression system is HEK293T cells.

The structure positions of the engineered Cys residues of the heavy and light chains can be numbered according to a sequential numbering system. This sequential numbering system is correlated to the Kabat numbering system (Kabat et al., (1991) Sequences of Proteins of Immunological Interest, 5th Ed. Public Health Service, National Institutes of Health, Bethesda, Md.) for the 4D5 antibody in FIGS. 13A and 13B. Using the Kabat numbering system, the actual linear amino acid sequence of the may contain fewer or additional amino acids corresponding to a shortening of, or insertion into, a FR or CDR of the variable domain. Cysteine engineered heavy chain variant sites and light chain variant sites are identified by the sequential numbering and Kabat numbering in FIGS. 13A and 13B.

Thiol reactivity may also be generalized to certain domains of an antibody, such as the light chain constant domain (CL) and heavy chain constant domains, CH1, CH2 and CH3. Cysteine replacements resulting in thiol reactivity values of about 0.1, 0.2, 0.3, 0.4, 0.5, 0.6, 0.7, 0.8, 0.9, and 0.95 and higher may be made in the heavy chain constant domains α, δ, ε, γ, and µ of intact antibodies: IgA, IgD, IgE, IgG, and IgM, respectively, including the IgG subclasses: IgG1, IgG2, IgG3, IgG4, IgA, and IgA2.

Cysteine engineered antibodies may be generated as described, e.g., in U.S. Pat. No. 7,521,541 or International Patent Publication No. WO 2006/034488, which are incorporated by reference herein in their entirety. In some embodiments, the cysteine engineered antibody variant is a cysteine engineered antibody variant described in U.S. Pat. No. 7,521,541 or International Patent Publication No. WO 2006/034488. In some instances, the cysteine engineered antibody variant is a cysteine engineered antibody variant described in International Patent Application Publication No. WO 2011/156328 or U.S. Pat. No. 9,000,130, which are incorporated by reference herein in their entirety. In some embodiments, the cysteine engineered antibody variant is a cysteine engineered antibody variant described in International Patent Application Publication No. WO 2016/040856, which is incorporated herein by reference in its entirety, for example, in Tables 1-4 of WO 2016/040856.

For example, in certain embodiments, the cysteine mutation is selected from the group consisting of HC-I195C, HC-S420C, HC-Y432C, and LC-G64C (according to Kabat numbering). In certain embodiments, the cysteine mutation is selected from the group consisting of HC-Y432C and LC-G64C (according to Kabat numbering). In certain embodiments, the cysteine mutation is a heavy chain mutation and is selected from the group consisting of Y33C, G162C, V184C, I195C, S420C, Y432C, and Q434C (according to Kabat numbering). In certain embodiments, the cysteine mutation is a heavy chain mutation and is selected from the group consisting of R19C, E46C, T57C, Y59C, A60C, M100cC, W103C, G162C, I195C, V258C, S420C, H425C, and N430C (according to Kabat numbering). In certain embodiments, the cysteine mutation is a heavy chain mutation and is selected from the group consisting of Y33C, G162C, V184C, and I195C (according to Kabat numbering). In certain embodiments, the cysteine mutation is a heavy chain mutation and is selected from the group consisting of R19C, E46C, Y59C, A60C, M100cC, W103C, V258C, H425C, and N430C (according to Kabat numbering). In certain embodiments, the cysteine mutation is a light chain mutation and is selected from the group consisting of Y55C, G64C, T85C, T180C, and N430C (according to Kabat numbering). In certain embodiments, the cysteine mutation is a light chain mutation and is selected from the group consisting of T31C, S52C, G64C, R66C, A193C, and N430C (according to Kabat numbering). In certain embodiments, the cysteine mutation is a light chain mutation and is selected from the group consisting of G64C, T85C, T180C, and N430C (according to Kabat numbering). In certain embodiments, the cysteine mutation is a light chain mutation and is selected from the group consisting of S52C, G64C, R66C, A193C, and N430C (according to Kabat numbering). In specific embodiments, the cysteine mutation in the light chain is selected from the group of cysteine mutations comprising LC-I106C, LC-R108C, LC-R142C, and LC-K149C (according to Kabat numbering) (see FIG. 13A; Table 2). In a particular embodiment, the cysteine mutation in the light chain is LC-K149C (according to Kabat numbering) (see FIG. 13A). In a particular embodiment, the cysteine mutation in the in the light chain is LC-V205C (according to Kabat numbering).

TABLE 2

Exemplary Light Chain Cysteine Mutations

| Resiude | Sequence (+/- 5 Residues) | SEQ ID NO. | EU Numbering | Kabat Numbering |
|---|---|---|---|---|
| I | GTKVECKRTVA | 70 | 106 | 106 |
| R | KVEIKCTVAAP | 71 | 108 | 108 |
| R | NNFYPCEAKVQ | 72 | 142 | 142 |
| K | AKVQWCVDNAL | 73 | 149 | 149 |

In particular embodiments, the cysteine mutation in the heavy chain is selected from the group of cysteine mutations consisting of HC-T114C, HC-A140C, HC-L174C, HC-L179C, HC-T187C, HC-T209C, HC-V262C, HC-G371C, HC-Y373C, HC-E382C, HC-S424C, HC-N434C, and HC-Q438C (according to EU numbering) (see FIG. 13B; Table 3). In a particular embodiment, the cysteine mutation in the heavy chain is HC-A143C according to Kabat numbering (i.e., HC-A140C according to EU numbering) (see FIG. 13B; Table 3). In a particular embodiment, the cysteine mutation in the heavy chain is HC-A174C according to EU numbering (see FIG. 13B; Table 3). In a particular embodiment, the cysteine mutation in the heavy chain is HC-A118C according to EU numbering (i.e., HC-A114C according to Kabat numbering).

In a particular embodiment, any cysteine engineered antibody as described herein has one of the following cysteine mutations: LC-K149C according to Kabat numbering and HC-A140C according to EU numbering (see Tables 2 and 3 and FIGS. 13A and 13B).

TABLE 3

Exemplary Heavy Chain Cysteine Mutations

| Residue | Sequence (+/-5 Residues) | SEQ ID NO. | EU Numbering | Kabat Numbering |
|---|---|---|---|---|
| T | QGTLVCVSSAS | 74 | 114 | 110 |
| A | TSGGTCALGCL | 75 | 140 | 136 |
| L | TFPAVCQSSGL | 76 | 174 | 170 |
| L | LQSSGCYSLSS | 77 | 179 | 175 |
| T | LSSVVCVPSSS | 78 | 187 | 183 |
| T | HKPSNCKVDKK | 79 | 209 | 205 |
| V | PEVTCCVVDVS | 80 | 262 | 258 |
| G | TCLVKCFYPSD | 81 | 371 | 367 |
| Y | LVKGFCPSDIA | 82 | 373 | 369 |
| E | IAVEWCSNGQP | 83 | 382 | 378 |
| S | QGNVFCCSVMH | 84 | 424 | 420 |
| N | HEALHCHYTQK | 85 | 434 | 430 |
| Q | HNHYTCKSLSL | 86 | 438 | 434 |

In certain embodiments, any one or more of the following residues may be substituted with cysteine: V205 (Kabat numbering) of the light chain; A118 (EU numbering) of the heavy chain; and S400 (EU numbering) of the heavy chain Fc region.

In certain embodiments, the cysteine engineered antibody may include one or more heavy chain cysteine mutations selected from the group consisting of V2C, L4C, V5C, L110, R19C, F27C, I29C, T32C, Y33C, Q39C, A40C, K43C, L45C, E46C, T53C, G55C, T57C, R58C, Y59C, A60C, T68C, N76C, Y79C, Q81C, W95C, G96C, D101C, W103C, T116C, K117C, T135C, N155C, A158C, G162C, G174C, L175C, T183C, V184C, I195C, N199C, S203C, F239C, M248C, E254C, V258C, N272C, V278C, L305C, T331C, S333C, R340C, Q343C, K356C, E384C, S399C, K410C, Q414C, G416C, N417C, Y432C, T433C, K435C, S438C, L439C, M100cC, and N82aC (according to Kabat numbering). See also Table 3 of International Patent Application No. WO 2016/040856.

In certain embodiments, the cysteine engineered antibody may include one or more light chain cysteine mutations selected from the group consisting of S12C, S14C, G16C, R18C, T22C, R24C, Q27C, T31C, A32C, Q38C, K39C, G41C, K42C, P44C, Y49C, S50C, S52C, F53C, L54C, Y55C, S63C, G64C, R66C, D70C, T72C, T74C, S76C, Q79C, T85C, H91C, Y92C, P95C, T97C, F98C, K103C, E105C, K107C, P119C, K126C, T129C, S131C, Q147C, W148C, A153C, Q155C, S156C, S159C, Q160C, S162C, Q166C, T172C, T180C, V191C, A193C, E195C, V205C, T206C, and N210C (according to Kabat numbering). See also Table 4 of International Patent Application No. WO 2016/040856.

In certain embodiments, the cysteine engineered antibody may include one or more cysteine mutations selected from the group consisting of HC-I195C, HC-S420C, HC-Y432C, and LC-G640 (according to Kabat numbering). See also Table 5 of International Patent Application No. WO 2016/040856.

In certain embodiments, the cysteine engineered antibody includes a light chain cysteine mutation selected from the group of sites consisting of LC-T220, LC-K390, LC-Y490, LC-Y550, LC-T850, LC-T970, LC-I106C, LC-R108C, LC-R142C, LC-K149C, and LC-V205C (according to Kabat numbering).

The cysteine engineered antibody may include any suitable number of engineered cysteine residues, e.g., 1, 2, 3, 4, 5, 6, 7, 8, 9, 10, 11, 12, 13, 14, 15, or more engineered cysteine residues. In some embodiments, the cysteine engineered antibody may include from 1-3, 1-4, 1-5, 1-6, 1-7, 1-8, 1-9, or 1-10 engineered cysteine residues. In some embodiments, the cysteine engineered antibody may include 1 engineered cysteine residue. In some embodiments, the cysteine engineered antibody may include 2 engineered cysteine residues. In some embodiments, the cysteine engineered antibody may include 3 engineered cysteine residues.

In any of the preceding embodiments, the cysteine engineered antibody may include an engineered cysteine at the equivalent position as any of the cysteine mutations described above. For instance, if an antibody includes a native serine at position 118 (EU numbering), the serine can be mutated to a cysteine to form an S118C mutation.

For example, the invention provides a cysteine engineered anti-VEGF antibody comprising a cysteine mutation in the heavy chain selected from the group consisting of HC-A118C, HC-A140C, and HC-L174C (EU numbering), or a cysteine mutation in the light chain selected from the group consisting of LC-V205C and LC-K149C (Kabat numbering), wherein the anti-VEGF antibody is any anti-VEGF antibody described herein, for example, any anti-VEGF antibody described in Tables 8-10. In some embodiments, the anti-VEGF antibody is N94A.F83A.N82aR.Y58R (G6.31 AARR). In some embodiments, the anti-VEGF antibody is G6.31 WT. In some embodiments, the anti-VEGF antibody is LC-N94A. In some embodiments, the anti-VEGF antibody is LC-N94A.LC-F83A. In some embodiments, the anti-VEGF antibody is LC-N94A.LC-F83A. In some embodiments, the anti-VEGF antibody is HC-A40E.HC-T57E (G6.31 AAEE). In some embodiments, the anti-VEGF antibody is HCcombo. In some embodiments, the anti-VEGF antibody is HCLC2. In some embodiments, the anti-VEGF antibody is HCLC4. In some embodiments, the anti-VEGF antibody is HCLC5. In some embodiments, the anti-VEGF antibody is HCLC3. In some embodiments, the anti-VEGF antibody is HCLC1. In some embodiments, the anti-VEGF antibody is R19HCcombo. In some embodiments, the anti-VEGF antibody is R19HCLC2.

In some embodiments, the anti-VEGF antibody is R19HCLC4. In some embodiments, the anti-VEGF antibody is R19HCLC5.

In a particular example, the invention provides a cysteine engineered anti-VEGF antibody comprising an cysteine mutation in the heavy chain selected from the group consisting of HC-A1180, HC-A140C, and HC-L174C (EU numbering), or an cysteine mutation in the light chain selected from the group consisting of LC-V205C and LC-K149C (Kabat numbering), wherein the antibody comprises the following six HVRs: (a) an HVR-H1 comprising the amino acid sequence of DYWIH (SEQ ID NO: 1); (b) an HVR-H2 comprising the amino acid sequence of GITPAG-GYTRYADSVKG (SEQ ID NO: 7); (c) an HVR-H3 comprising the amino acid sequence of FVFFLPYAMDY (SEQ ID NO: 3); (d) an HVR-L1 comprising the amino acid sequence of RASQDVSTAVA (SEQ ID NO: 8); (e) an HVR-L2 comprising the amino acid sequence of SASFLYS (SEQ ID NO: 9); and (f) an HVR-L3 comprising the amino acid sequence of QQGYGAPFT (SEQ ID NO: 10). In some instances, the cysteine engineered anti-VEGF antibody includes the following four heavy chain variable domain FRs: (a) an FR-H1 comprising the amino acid sequence of EVQLVESGGGLVQPGGSLRLSCAASGFTIS (SEQ ID NO: 13); (b) an FR-H2 comprising the amino acid sequence of WVRQAPGKGLEWVA (SEQ ID NO: 14); (c) an FR-H3 comprising the amino acid sequence of RFTISADTSKN-TAYLQMRSLRAEDTAVYYCAR (SEQ ID NO: 15); and (d) an FR-H4 comprising the amino acid sequence of WGQGTLVTVSS (SEQ ID NO: 16). In further instances, the cysteine engineered anti-VEGF antibody includes the following four light chain variable domain FRs: (a) an FR-L1 comprising the amino acid sequence of DIQMTQSPSSLSASVGDRVTITC (SEQ ID NO: 17); (b) an FR-L2 comprising the amino acid sequence of WYQQKPGKAPKLLIY (SEQ ID NO: 18); (c) an FR-L3 comprising the amino acid sequence of GVPSRFSGSGSGTDFTLTISSLQPEDAATYYC (SEQ ID NO: 19); and (d) an FR-L4 comprising the amino acid sequence of FGQGTKVEIK (SEQ ID NO: 20). In some instances, the cysteine engineered anti-VEGF antibody includes (a) a VH domain comprising an amino acid sequence of SEQ ID NO: 11 and (b) a VL domain comprising an amino acid sequence of SEQ ID NO: 12. In some instances, the parent antibody is G6.31 AARR. In some embodiments, the cysteine mutation is HC-A1180. In other embodiments, the cysteine mutation is HC-A140C. In yet other embodiments, the cysteine mutation is HC-L174C (EU numbering). In other embodiments, the cysteine mutation is LC-V205C (Kabat numbering). In other embodiments, the cysteine mutation is LC-K1490 (Kabat numbering).

In some instances, the invention provides an antibody comprising (a) a heavy chain comprising the amino acid sequence of SEQ ID NO: 90 and/or (b) a light chain comprising the amino acid sequence of SEQ ID NO: 89.

In some instances, the invention provides an antibody comprising (a) a heavy chain comprising the amino acid sequence of SEQ ID NO: 92 and/or (b) a light chain comprising the amino acid sequence of SEQ ID NO: 91.

In some instances, the invention provides an antibody comprising (a) a heavy chain comprising the amino acid sequence of SEQ ID NO: 94 and/or (b) a light chain comprising the amino acid sequence of SEQ ID NO: 93.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, and the like. Additional antibody conjugates are described herein, for example, in Section G below and in Examples 1 and 2.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

f) Isoelectric Point Variants

The invention provides antibodies variants with altered isoelectric points. For example, the invention provides antibodies variants with a reduced isoelectric point (pI), for example, as compared to an anti-VEGF antibody, for instance, G6.31. In some instances, the surface charge is reduced at physiological pH. In some instances, the anti-VEGF antibody has a pI equal to or lower than about 8 (e.g., about 8, about 7, about 6, about 5, or about 4). In some instances, the antibody has a pI from about 4 to about 8 (e.g., about 4, about 5, about 6, about 7, or about 8). In some instances, the anti-VEGF antibody has a pI from about 5 to about 7 (e.g., about 5, about 6, or about 7). In some instances, the anti-VEGF antibody has a pI from about 5 to about 6 (e.g., about 5.1, about 5.2, about 5.3, about 5.4, about 5.5, about 5.6, about 5.7, about 5.8, about 5.9, or about 6).

Antibodies of the invention may be engineered to have a reduced pI, for example, by substituting wild-type amino acid residues at a given position with an amino acid having a lower pI. The pI of an amino acid can be determined based on the pKa values of the amine ($-NH_2$), carboxylic acid ($-COOH$), and side-chain of the amino acid, which are known in the art. In some embodiments, surface-exposed amino acid residues may be substituted to reduce the pI of an antibody. In one embodiment, surface-exposed amino acid residues may be substituted with glutamate (E). In one embodiment, surface-exposed amino acid residues may be substituted with aspartate (D).

B. Recombinant Methods and Compositions

Any of the antibodies (e.g., anti-VEGF antibodies, including cysteine engineered anti-VEGF antibodies) described herein may be produced using recombinant methods and compositions, for example, as described in U.S. Pat. No. 4,816,567. In one embodiment, an isolated nucleic acid encoding an anti-VEGF antibody described herein is provided. Such a nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such a nucleic acid are provided. In a further embodiment, a host cell comprising such a nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, for example, a Chinese Hamster Ovary (CHO) cell or lymphoid cell (e.g., Y0, NS0, Sp20 cell). In one embodiment, a method of making an anti-VEGF antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody (e.g., an anti-VEGF antibody, including a cysteine engineered anti-VEGF antibody), nucleic acid encoding an antibody, for example, as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, for example, U.S. Pat. Nos. 5,648,237, 5,789,199, and 5,840,523. See also Charlton, *Methods in Molecular Biology*, Vol. 248 (B. K. C. Lo, ed., Humana Press, Totowa, NJ, 2003), pp. 245-254, describing expression of antibody fragments in *E. coli*. After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, for example, U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, for example, Yazaki and Wu, *Methods in Molecular Biology*, Vol. 248 (B. K. C. Lo, ed., Humana Press, Totowa, NJ), pp. 255-268 (2003).

C. Assays

Antibodies (e.g., anti-VEGF antibodies described herein, including cysteine engineered anti-VEGF antibodies), as well as antibody conjugates (e.g., antibody conjugates that include anti-VEGF antibodies (e.g., any anti-VEGF antibody provided herein)), may be identified, screened for, or characterized for their physical/chemical properties and/or biological activities by various assays known in the art.

1. Binding Assays and Other Assays

In one aspect, an antibody (e.g., an anti-VEGF antibody, including a cysteine engineered anti-VEGF antibody), or an antibody conjugate thereof, is tested for its antigen binding activity, e.g., by known methods such as ELISA, Western blot, etc.

In another aspect, competition assays may be used to identify an antibody that competes with an antibody as described herein, or an antibody conjugate thereof, for binding to an antigen (e.g., VEGF). In certain embodiments, such a competing antibody binds to the same epitope (e.g., a linear or a conformational epitope) that is bound by an antibody as described herein. Detailed exemplary methods for mapping an epitope to which an antibody binds are provided in Morris (1996) "Epitope Mapping Protocols," in *Methods in Molecular Biology* vol. 66 (Humana Press, Totowa, NJ).

In an exemplary competition assay, immobilized VEGF is incubated in a solution comprising a first labeled antibody that binds to VEGF and a second unlabeled antibody that is being tested for its ability to compete with the first antibody for binding to VEGF. The second antibody may be present in a hybridoma supernatant. As a control, immobilized VEGF is incubated in a solution comprising the first labeled antibody but not the second unlabeled antibody. After incubation under conditions permissive for binding of the first antibody to VEGF, excess unbound antibody is removed, and the amount of label associated with immobilized VEGF is measured. If the amount of label associated with immobilized VEGF is substantially reduced in the test sample relative to the control sample, then that indicates that the second antibody is competing with the first antibody for binding to VEGF. Similar assays may be performed for other antigens. See Harlow and Lane (1988) *Antibodies: A Laboratory Manual* ch. 14 (Cold Spring Harbor Laboratory, Cold Spring Harbor, NY).

2. Activity Assays

In one aspect, assays are provided for identifying antibodies (e.g., anti-VEGF antibodies, including cysteine engineered anti-VEGF antibodies), or antibody conjugates thereof, having biological activity. Biological activity may include, for example, binding to an antigen (e.g., VEGF (e.g., VEGF in the blood stream)), or a peptide fragment thereof, either in vivo, in vitro, or ex vivo. In certain embodiments, biological activity may include blocking or neutralizing an antigen. For example, in certain embodiments, biological activity may include blocking or neutralizing VEGF, or preventing VEGF from binding to a ligand, for example, a receptor such as KDR or Flt-1. Antibodies, or antibody conjugates thereof, having such biological activity in vivo and/or in vitro are also provided. In certain embodiments, an antibody of the invention, or an antibody conjugate thereof, is tested for such biological activity.

3. Stability Assays

In one aspect, assays are provided for determining the stability (e.g., thermostability) of an antibody (e.g., an anti-VEGF antibody, including a cysteine engineered anti-VEGF antibody), or an antibody conjugate thereof. For example, the stability of an antibody, or an antibody conjugate thereof, may be determined using any method known in the art, for example, differential scanning fluorimetry (DSF), circular dichroism (CD), intrinsic protein fluorescence, differential scanning calorimetry, spectroscopy, light scattering (e.g., dynamic light scattering (DLS) and static light scattering (SLS), self-interaction chromatography (SIC). The stability of an antibody, or an antibody conjugate thereof, may be determined as described herein, for example, using DSF as described, for example, in Examples 1 and 2 of International Patent Application No. PCT/US2016/053454. In some instances, the stability of an antibody conjugate can be determined by size exclusion chromatography in-line with refractive index and multi-angle light scattering detectors (SEC-RI-MALS), for example, as described in Example 1.

D. Pharmaceutical Formulations

Pharmaceutical formulations of an antibody (e.g., an anti-VEGF antibody, including a cysteine engineered anti-VEGF antibody) or antibody conjugate thereof provided herein are prepared by mixing such antibody or antibody conjugate having the desired degree of purity with one or more optional pharmaceutically acceptable carriers (Remington's Pharmaceutical Sciences 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

The formulations to be used for in vivo administration are generally sterile. Sterility may be readily accomplished, for example, by filtration through sterile filtration membranes.

In certain embodiments, the pharmaceutical formulation includes one or more additional compounds. In certain embodiments, the additional compound binds to a second biological molecule selected from the group consisting of IL-1β; IL-6; IL-6R; IL-13; IL-13R; PDGF; angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor; ST-2 receptor; and proteins genetically linked to age-related macular degeneration (AMD) risk, such as complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC; COL10A1; and TNFRSF10A. In certain embodiments, the additional compound is an antibody or antigen-binding fragment thereof.

For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157.

In another example, in some instances, the additional compound is an anti-IL-6 antibody, for example, EBI-031 (Eleven Biotherapeutics; see, e.g., WO 2016/073890), siltuximab (SYLVANT®), olokizumab, clazakizumab, sirukumab, elsilimomab, gerilimzumab, OPR-003, MEDI-5117, PF-04236921, or a variant thereof.

In a still further example, in some instances, the additional compound is an anti-IL-6R antibody, for example, tocilizumab (ACTEMRA®) (see, e.g., WO 1992/019579), sarilumab, vobarilizumab (ALX-0061), SA-237, or a variant thereof.

E. Therapeutic Methods and Compositions

Any of the antibodies (e.g., anti-VEGF antibodies, including cysteine engineered anti-VEGF antibodies) or antibody conjugates thereof (e.g., monodisperse HA conjugates) provided herein may be used in therapeutic methods.

In one aspect, an anti-VEGF antibody (e.g., an engineered cysteine anti-VEGF antibody) for use as a medicament is provided. In another aspect, an antibody conjugate (e.g., a monodisperse HA conjugate) for use as a medicament is provided. In further aspects, the invention provides an anti-VEGF antibody (e.g., an engineered cysteine anti-VEGF antibody) for use in treating a disorder associated with pathological angiogenesis. In another aspect, the invention provides an antibody conjugate (e.g., a monodisperse HA conjugate) for use in treating a disorder associated with pathological angiogenesis. In some embodiments, the disorder associated with pathological angiogenesis is an ocular disorder. In some instances, the ocular disorder is AMD (e.g., wet AMD, dry AMD, intermediate AMD, advanced AMD, or geographic atrophy (GA)), macular degeneration, macular edema, DME (e.g., focal, non-center DME or diffuse, center-involved DME), retinopathy, diabetic retinopathy (DR) (e.g., proliferative DR (PDR), non-proliferative DR (NPDR), or high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g., allergic) conjunctivitis), Leber congenital amaurosis, uveitis (including infectious and non-infectious uveitis), choroiditis (e.g., multifocal choroiditis), ocular histoplasmosis, blepharitis, dry eye, traumatic eye injury, or Sjögren's disease.

In another aspect, an anti-VEGF antibody (e.g., an engineered cysteine anti-VEGF antibody) for use in a method of treatment is provided. In another aspect, an antibody conjugate (e.g., a monodisperse HA conjugate) for use in a method of treatment is provided. In certain instances, the invention provides an anti-VEGF antibody (e.g., an engineered cysteine anti-VEGF antibody) for use in a method of treating a subject having a disorder associated with pathological angiogenesis comprising administering to the individual an effective amount of the anti-VEGF antibody. The invention also provides an antibody conjugate (e.g., a monodisperse HA conjugate) for use in a method of treating a subject having a disorder associated with pathological angiogenesis comprising administering to the individual an effective amount of the antibody conjugate. In some instances, the disorder associated with pathological angiogenesis is an ocular disorder. In some instances, the ocular disorder is AMD (e.g., wet AMD, dry AMD, intermediate AMD, advanced AMD, or geographic atrophy (GA)), macular degeneration, macular edema, DME (e.g., focal, non-center DME or diffuse, center-involved DME), retinopathy, diabetic retinopathy (DR) (e.g., proliferative DR (PDR), non-proliferative DR (NPDR), or high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g., allergic) conjunctivitis), Leber congenital amaurosis, uveitis (including infectious and non-infectious uveitis), choroiditis (e.g., multifocal choroiditis), ocular histoplasmosis, blepharitis, dry eye, traumatic eye injury, or Sjögren's disease.

In some instances, the invention provides an anti-VEGF antibody (e.g., an engineered cysteine anti-VEGF antibody) for use in reducing or inhibiting angiogenesis in a subject. In another aspect, an antibody conjugate (e.g., a monodisperse HA conjugate) for use in reducing or inhibiting angiogenesis in a subject is provided. In certain embodiments, the invention provides an anti-VEGF antibody (e.g., an engineered cysteine anti-VEGF antibody) for use in a method of reducing or inhibiting angiogenesis in a subject comprising administering to the individual an effective of the anti-VEGF antibody to reduce or inhibit angiogenesis. The invention also provides an antibody conjugate (e.g., a monodisperse HA conjugate) for use in a method of reducing or inhibiting angiogenesis in a subject comprising administering to the individual an effective amount of the antibody conjugate. A "subject" according to any of the above uses may be a human.

The invention provides for the use of an anti-VEGF antibody (e.g., an engineered cysteine anti-VEGF antibody) in the manufacture or preparation of a medicament. The invention also provides for the use of an antibody conjugate (e.g., a monodisperse HA conjugate) in the manufacture or preparation of a medicament. For example, in one instance, the medicament is for treatment of a disorder associated with pathological angiogenesis. In a further instance, the medicament is for use in a method of treating a disorder associated with pathological angiogenesis comprising administering to a subject having a disorder associated with pathological angiogenesis an effective amount of the medicament. In some instances, the disorder associated with pathological angiogenesis is an ocular disorder. In some instances, the ocular disorder is AMD (e.g., wet AMD, dry AMD, intermediate AMD, advanced AMD, or geographic atrophy (GA)), macular degeneration, macular edema, DME (e.g., focal, non-center DME or diffuse, center-involved DME), retinopathy, diabetic retinopathy (DR) (e.g., proliferative DR (PDR), non-proliferative DR (NPDR), or high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g., allergic) conjunctivitis), Leber congenital amaurosis, uveitis (including infectious and non-infectious uveitis), choroiditis (e.g., multifocal choroiditis), ocular histoplasmosis, blepharitis, dry eye, traumatic eye injury, or Sjögren's disease. In a further instance, the medicament is for reducing or inhibiting angiogenesis in a subject. In a further instance, the medicament is for use in a method of reducing or inhibiting angiogenesis in a subject comprising administering to the subject an amount effective of the medicament to reduce or inhibit angiogenesis. In any of the preceding uses of medicaments, the method may include administering to the individual an effective amount of at least one additional therapeutic agent, e.g., as described below.

The invention provides a method for treating a disorder associated with pathological angiogenesis. In one embodiment, the method comprises administering to an individual having a disorder associated with pathological angiogenesis an effective amount of an anti-VEGF antibody (e.g., an engineered cysteine anti-VEGF antibody). In another example, the method comprises administering to an individual having a disorder associated with pathological angiogenesis an effective amount of an antibody conjugate (e.g., a monodisperse HA conjugate). In some instances, the disorder associated with pathological angiogenesis is an ocular disorder. In some instances, the ocular disorder is AMD (e.g., wet AMD, dry AMD, intermediate AMD, advanced AMD, or geographic atrophy (GA)), macular degeneration, macular edema, DME (e.g., focal, non-center DME or diffuse, center-involved DME), retinopathy, diabetic retinopathy (DR) (e.g., proliferative DR (PDR), non-proliferative DR (NPDR), or high-altitude DR), other ischemia-related retinopathies, ROP, retinal vein occlusion (RVO) (e.g., central (CRVO) and branched (BRVO) forms), CNV (e.g., myopic CNV), corneal neovascularization, diseases associated with corneal neovascularization, retinal neovascularization, diseases associated with retinal/choroidal neovascularization, pathologic myopia, von Hippel-Lindau disease, histoplasmosis of the eye, FEVR, Coats' disease, Norrie Disease, OPPG, subconjunctival hemorrhage, rubeosis, ocular neovascular disease, neovascular glaucoma, retinitis pigmentosa (RP), hypertensive retinopathy, retinal angiomatous proliferation, macular telangiectasia, iris neovascularization, intraocular neovascularization, retinal degeneration, cystoid macular edema (CME), vasculitis, papilloedema, retinitis, conjunctivitis (e.g., infectious conjunctivitis and non-infectious (e.g., allergic) conjunctivitis), Leber congenital amaurosis, uveitis (including infectious and non-infectious uveitis), choroiditis (e.g., multifocal choroiditis), ocular histoplasmosis, blepharitis, dry eye, traumatic eye injury, or Sjögren's disease. In further instances, the method further comprises administering to the individual an effective amount of at least one additional therapeutic agent, as described below. A "subject" according to any of the above methods may be a human.

It is contemplated that the antibody (e.g., cysteine engineered anti-VEGF antibody) or antibody conjugate (e.g., monodisperse HA conjugate) of the present invention may be used to treat a mammal. In one embodiment, the antibody (e.g., cysteine engineered anti-VEGF antibody) or antibody conjugate (e.g., monodisperse HA conjugate) is administered to a nonhuman mammal for the purposes of obtaining preclinical data, for example. Exemplary nonhuman mammals to be treated include nonhuman primates, dogs, cats, rodents (e.g., mice and rats) and other mammals in which preclinical studies are performed. Such mammals may be established animal models for a disease to be treated with the antibody or may be used to study toxicity or pharmacokinetics of the antibody of interest. In each of these embodiments, dose escalation studies may be performed in the mammal. The antibody (e.g., cysteine engineered anti-VEGF antibody) or antibody conjugate (e.g., monodisperse HA conjugate) may be administered to a host rodent in a solid tumor model, for example. The antibody or antibody conjugate may be administered to a host (e.g., a rodent, e.g., a rabbit) for ocular pharmacokinetic studies, for example, by intravitreal administration (e.g., intravitreal injection) or using a port delivery device.

In a further aspect, the invention provides pharmaceutical formulations comprising any of the antibodies (e.g., cysteine engineered anti-VEGF antibodies) or antibody conjugates (e.g., monodisperse HA conjugates) provided herein, for example, for use in any of the above therapeutic methods. In one embodiment, a pharmaceutical formulation comprises any of the antibodies (e.g., cysteine engineered anti-VEGF antibodies) or antibody conjugates (e.g., monodisperse HA conjugates) provided herein and a pharmaceutically acceptable carrier. In another embodiment, a pharmaceutical formulation comprises any of the antibodies (e.g., cysteine engineered anti-VEGF antibodies) or antibody conjugates (e.g., monodisperse HA conjugates) provided herein and at least one additional therapeutic agent, for example, as described below. In certain embodiments, the pharmaceutical formulation comprises one or more additional compounds. In certain embodiments, the additional compound binds to a second biological molecule selected from the group consisting of IL-1β; IL-6; IL-6R; IL-13; IL-13R; PDGF; angiopoietin; Ang2; Tie2; S1P; integrins αvβ3, αvβ5, and α5β1; betacellulin; apelin/APJ; erythropoietin; complement factor D; TNFα; HtrA1; a VEGF receptor; ST-2 receptor; and proteins genetically linked to age-related macular degeneration (AMD) risk, such as complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC, COL10A1; and TNFRSF10A. In certain embodiments, the additional compound is an antibody or antigen-binding fragment thereof. For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof. In another example, in some instances, the additional compound is an anti-IL-6 antibody, for example, EBI-031 (Eleven Biotherapeutics; see, e.g., WO 2016/073890), siltuximab (SYLVANT®), olokizumab, clazakizumab, sirukumab, elsilimomab, gerilimzumab, OPR-003, MEDI-5117, PF-04236921, or a variant thereof. In a still further example, in some instances, the additional compound is an anti-IL-6R antibody, for example, tocilizumab (ACTEMRA®) (see, e.g., WO 1992/019579), sarilumab, vobarilizumab (ALX-0061), SA-237, or a variant thereof.

Antibodies (e.g., cysteine engineered anti-VEGF antibodies) or antibody conjugates (e.g., monodisperse HA conjugates) can be used either alone or in combination with other agents in a therapy. For instance, an antibody (e.g., a cysteine engineered anti-VEGF antibody) or antibody conjugate (e.g., a monodisperse HA conjugate) may be co-administered with at least one additional therapeutic agent.

In certain embodiments, an additional therapeutic agent is another antibody, an anti-angiogenic agent, an immunosuppressive agent, a cytokine, a cytokine antagonist, a corticosteroid, an anti-emetic, a cancer vaccine, an analgesic, or combinations thereof.

For example, in certain embodiments, any of the preceding methods further comprises administering one or more additional compounds. In certain embodiments, the antibody (e.g., a cysteine engineered anti-VEGF antibody) or antibody conjugate (e.g., a monodisperse HA conjugate) is administered simultaneously with the additional compound(s). In certain embodiments, the antibody or antibody conjugate is administered before or after the additional compound(s). In certain embodiments, the additional compound binds to a second biological molecule selected from the group consisting of IL-1β; IL-6; IL-6R; IL-13; IL-13R; PDGF; angiopoietin; Ang2; Tie2; S1P; integrins αvβ3, αvβ5, and α5β1; betacellulin; apelin/APJ; erythropoietin; complement factor D; TNFα; HtrA1; a VEGF receptor; ST-2 receptor; and proteins genetically linked to AMD risk, such as complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC; COL10A1; and TNFRSF10A. In certain embodiments, the additional compound is an antibody or antigen-binding fragment thereof.

In certain embodiments according to (or as applied to) any of the embodiments above, the ocular disorder is an intraocular neovascular disease selected from the group consisting of proliferative retinopathies, choroidal neovascularization (CNV), age-related macular degeneration (AMD), diabetic and other ischemia-related retinopathies, diabetic macular edema, pathological myopia, von Hippel-Lindau disease, histoplasmosis of the eye, retinal vein occlusion (RVO), including CRVO and BRVO, corneal neovascularization, retinal neovascularization, and retinopathy of prematurity (ROP). For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof. In another example, in some instances, the additional compound is an anti-IL-6 antibody, for example, EBI-031 (Eleven Biotherapeutics; see, e.g., WO 2016/073890), siltuximab (SYLVANT®), olokizumab, clazakizumab, sirukumab, elsilimomab, gerilimzumab, OPR-003, MEDI-5117, PF-04236921, or a variant thereof. In a still further example, in some instances, the additional compound is an anti-IL-6R antibody, for example, tocilizumab (ACTEMRA®) (see, e.g., WO 1992/019579), sarilumab, vobarilizumab (ALX-0061), SA-237, or a variant thereof.

In some instances, an antibody (e.g., a cysteine engineered anti-VEGF antibody) or an antibody conjugate (e.g., a monodisperse HA conjugate) of the invention may be administered in combination with at least one additional therapeutic agent for treatment of an ocular disorder, for example, an ocular disorder described herein (e.g., AMD (e.g., wet AMD), DME, DR, or RVO). Exemplary additional therapeutic agents for combination therapy for treatment of ocular disorders include, without limitation, anti-angiogenic agents, such as VEGF antagonists, including, for example, anti-VEGF antibodies (e.g., the anti-VEGF Fab LUCENTIS® (ranibizumab)), soluble receptor fusion proteins (e.g., the recombinant soluble receptor fusion protein EYLEA® (aflibercept, also known as VEGF Trap Eye; Regeneron/Aventis)), aptamers (e.g., the anti-VEGF pegylated aptamer MACUGEN® (pegaptanib sodium; NeXstar Pharmaceuticals/OSI Pharmaceuticals)), and VEGFR tyrosine kinase inhibitors (e.g., 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787), semaxaminib (SU5416; SUGEN), and SUTENT® (sunitinib)); Tryptophanyl-tRNA synthetase (TrpRS); squalamine; RETAANE® (anecortave acetate for depot suspension; Alcon, Inc.); Combretastatin A4 Prodrug (CA4P); MIFEPREX® (mifepristone-ru486); subtenon triamcinolone acetonide; intravitreal crystalline triamcinolone acetonide; matrix metalloproteinase inhibitors (e.g., Prinomastat (AG3340; Pfizer)); fluocinolone acetonide (including fluocinolone intraocular implant; Bausch & Lomb/Control Delivery Systems); linomide; inhibitors of integrin β3 function; angiostatin, and combinations thereof. These and other therapeutic agents that can be administered in combination with an antibody conjugate of the invention are described, for example, in U.S. Patent Application No. US 2014/0017244, which is incorporated herein by reference in its entirety.

Further examples of additional therapeutic agents that can be used in combination with an antibody (e.g., a cysteine engineered anti-VEGF antibody) or an antibody conjugate (e.g., a monodisperse HA conjugate) of the invention for treatment of an ocular disorder (e.g., AMD, DME, DR, or RVO), include, but are not limited to, VISUDYNE® (verteporfin; a light-activated drug that is typically used in conjunction with photodynamic therapy with a non-thermal laser), PKC412, Endovion (NS 3728; NeuroSearch A/S), neurotrophic factors (e.g., glial derived neurotrophic factor (GDNF) and ciliary neurotrophic factor (CNTF)), diltiazem, dorzolamide, PHOTOTROP®, 9-cis-retinal, eye medication (e.g., phospholine iodide, echothiophate, or carbonic anhydrase inhibitors), veovastat (AE-941; AEterna Laboratories, Inc.), Sirna-027 (AGF-745; Sima Therapeutics, Inc.), neurotrophins (including, by way of example only, NT-4/5, Genentech), Cand5 (Acuity Pharmaceuticals), INS-37217 (Inspire Pharmaceuticals), integrin antagonists (including those from Jerini AG and Abbott Laboratories), EG-3306 (Ark Therapeutics Ltd.), BDM-E (BioDiem Ltd.), thalidomide (as used, for example, by EntreMed, Inc.), cardiotrophin-1 (Genentech), 2-methoxyestradiol (Allergan/Oculex), DL-8234 (Toray Industries), NTC-200 (Neurotech), tetrathiomolybdate (University of Michigan), LYN-002 (Lynkeus Biotech), microalgal compound (Aquasearch/Albany, Mera Pharmaceuticals), D-9120 (Celltech Group plc), ATX-S10 (Hamamatsu Photonics), TGF-beta 2 (Genzyme/Celtrix), tyrosine kinase inhibitors (e.g., those from Allergan, SUGEN, or Pfizer), NX-278-L (NeXstar Pharmaceuticals/Gilead Sciences), Opt-24 (OPTIS France SA), retinal cell ganglion neuroprotectants (Cogent Neurosciences), N-nitropyrazole derivatives (Texas A&M University System), KP-102 (Krenitsky Pharmaceuticals), cyclosporin A, therapeutic agents used in photodynamic therapy (e.g., VISUDYNE®; receptor-targeted PDT, Bristol-Myers Squibb, Co.; porfimer sodium for injection with PDT; verteporfin, QLT Inc.; rostaporfin with PDT, Miravent Medical Technologies; talaporfin sodium with PDT, Nippon Petroleum; and motexafin lutetium, Pharmacyclics, Inc.), antisense oligonucleotides (including, by way of example, products tested by Novagali Pharma SA and ISIS-13650, Isis Pharmaceuticals), and combinations thereof.

An antibody (e.g., a cysteine engineered anti-VEGF antibody) or antibody conjugate (e.g., a monodisperse HA conjugate) of the invention may be administered in combination with a therapy or surgical procedure for treatment of an ocular disorder (e.g., AMD, DME, DR, or RVO), including, for example, laser photocoagulation (e.g., panretinal photocoagulation (PRP)), drusen lasering, macular hole surgery, macular translocation surgery, implantable miniature telescopes, PHI-motion angiography (also known as microlaser therapy and feeder vessel treatment), proton beam therapy, microstimulation therapy, retinal detachment and vitreous surgery, scleral buckle, submacular surgery, transpupillary thermotherapy, photosystem I therapy, use of RNA interference (RNAi), extracorporeal rheopheresis (also known as membrane differential filtration and rheotherapy), microchip implantation, stem cell therapy, gene replacement therapy, ribozyme gene therapy (including gene therapy for hypoxia response element, Oxford Biomedica; Lentipak, Genetix; and PDEF gene therapy, GenVec), photoreceptor/retinal cells transplantation (including transplantable retinal epithelial cells, Diacrin, Inc.; retinal cell transplant, Cell Genesys, Inc.), acupuncture, and combinations thereof.

In some instances, an antibody (e.g., a cysteine engineered anti-VEGF antibody) or antibody conjugate (e.g., a monodisperse HA conjugate) of the invention can be administered in combination with an anti-angiogenic agent for treatment of an ocular disorder (e.g., AMD, DME, DR, or RVO). Any suitable anti-angiogenic agent can be used in combination with an antibody (e.g., a cysteine engineered anti-VEGF antibody) or an antibody conjugate of the invention, including, but not limited to, those listed by Carmeliet et al. Nature 407:249-257, 2000. In some embodiments, the anti-angiogenic agent is a VEGF antagonist, including, but not limited to, an anti-VEGF antibody (e.g., the anti-VEGF Fab LUCENTIS® (ranibizumab), RTH-258 (formerly ESBA-1008, an anti-VEGF single-chain antibody fragment; Novartis), or a bispecific anti-VEGF antibody (e.g., an anti-VEGF/anti-angiopoeitin 2 bispecific antibody such as RG-7716; Roche)), a soluble recombinant receptor fusion protein (e.g., EYLEA® (aflibercept)), a VEGF variant, a soluble VEGFR fragment, an aptamer capable of blocking VEGF (e.g., pegaptanib) or VEGFR, a neutralizing anti-VEGFR antibody, a small molecule inhibitor of VEGFR tyrosine kinases, an anti-VEGF DARPin® (e.g., abicipar pegol), a small interfering RNAs which inhibits expression of VEGF or VEGFR, a VEGFR tyrosine kinase inhibitor (e.g., 4-(4-bromo-2-fluoroanilino)-6-methoxy-7-(1-methylpiperidin-4-ylmethoxy)quinazoline (ZD6474), 4-(4-fluoro-2-methylindol-5-yloxy)-6-methoxy-7-(3-pyrrolidin-1-ylpropoxy)quinazoline (AZD2171), vatalanib (PTK787), semaxaminib (SU5416; SUGEN), and SUTENT® (sunitinib)), and combinations thereof. In some instances, the bispecific anti-VEGF antibody binds to a second biological molecule, including but not limited to IL-1β; IL-6; IL-6R; PDGF (e.g., PDGF-BB); angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor (e.g., VEGFR1, VEGFR2, VEGFR3, mbVEGFR, or sVEGFR); ST-2 receptor; and proteins genetically linked to age-related macular degeneration (AMD) risk, such as complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC; COL10A1; and TNFRSF10A. For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof.

Other suitable anti-angiogenic agents that may be administered in combination with an antibody (e.g., a cysteine engineered anti-VEGF antibody) or an antibody conjugate (e.g., a monodisperse HA conjugate) of the invention for treatment of an ocular disorder (e.g., AMD, DME, DR, or RVO) include corticosteroids, angiostatic steroids, anecortave acetate, angiostatin, endostatin, tyrosine kinase inhibitors, matrix metalloproteinase (MMP) inhibitors, insulin-like growth factor-binding protein 3 (IGFBP3), stromal derived factor (SDF-1) antagonists (e.g., anti-SDF-1 antibodies), pigment epithelium-derived factor (PEDF), gamma-secretase, Delta-like ligand 4, integrin antagonists, hypoxia-inducible factor (HIF)-1α antagonists, protein kinase CK2 antagonists, agents that inhibit stem cell (e.g., endothelial progenitor cell) homing to the site of neovascularization (e.g., an anti-vascular endothelial cadherin (CD-144) antibody and/or an anti-SDF-1 antibody), and combinations thereof.

In a further example, in some instances, an antibody (e.g., a cysteine engineered anti-VEGF antibody) or an antibody conjugate (e.g., a monodisperse HA conjugate) of the invention can be administered in combination with an agent that has activity against neovascularization for treatment of an ocular disorder (e.g., AMD, DME, DR, or RVO), such as an anti-inflammatory drug, a mammalian target of rapamycin (mTOR) inhibitor (e.g., rapamycin, AFINITOR® (everolimus), and TORISEL® (temsirolimus)), cyclosporine, a tumor necrosis factor (TNF) antagonist (e.g., an anti-TNFα antibody or antigen-binding fragment thereof (e.g., infliximab, adalimumab, certolizumab pegol, and golimumab) or a soluble receptor fusion protein (e.g., etanercept)), an anti-complement agent, a nonsteroidal antiinflammatory agent (NSAID), or combinations thereof.

In a still further example, in some instances, an antibody (e.g., a cysteine engineered anti-VEGF antibody) or an antibody conjugate (e.g., a monodisperse HA conjugate) of the invention can be administered in combination with an agent that is neuroprotective and can potentially reduce the progression of dry AMD to wet AMD, such as the class of drugs called the "neurosteroids," which include drugs such as dehydroepiandrosterone (DHEA) (brand names: PRASTERA™ and FIDELIN®), dehydroepiandrosterone sulfate, and pregnenolone sulfate.

Any suitable AMD therapeutic agent can be administered as an additional therapeutic agent in combination with an antibody (e.g., a cysteine engineered anti-VEGF antibody) or an antibody conjugate (e.g., a monodisperse HA conjugate) of the invention for treatment of an ocular disorder (e.g., AMD, DME, DR, or RVO), including, but not limited to, a VEGF antagonist, for example, an anti-VEGF antibody (e.g., LUCENTIS® (ranibizumab), RTH-258 (formerly ESBA-1008, an anti-VEGF single-chain antibody fragment; Novartis), or a bispecific anti-VEGF antibody (e.g., an anti-VEGF/anti-angiopoeitin 2 bispecific antibody such as RG-7716; Roche)), a soluble VEGF receptor fusion protein (e.g., EYLEA® (aflibercept)), an anti-VEGF DARPin® (e.g., abicipar pegol; Molecular Partners AG/Allergan), or an anti-VEGF aptamer (e.g., MACUGEN® (pegaptanib sodium)); a platelet-derived growth factor (PDGF) antagonist, for example, an anti-PDGF antibody, an anti-PDGFR antibody (e.g., REGN2176-3), an anti-PDGF-BB pegylated aptamer (e.g., FOVISTA®; Ophthotech/Novartis), a soluble PDGFR receptor fusion protein, or a dual PDGF/VEGF antagonist (e.g., a small molecule inhibitor (e.g., DE-120 (Santen) or X-82 (TyrogeneX)) or a bispecific anti-PDGF/anti-VEGF antibody)); VISUDYNE® (verteporfin) in combination with photodynamic therapy; an antioxidant; a complement system antagonist, for example, a complement factor C5 antagonist (e.g., a small molecule inhibitor (e.g., ARC-1905; Opthotech) or an anti-05 antibody (e.g., LFG-316; Novartis), a properdin antagonist (e.g., an anti-properdin antibody, e.g., CLG-561; Alcon), or a complement factor D antagonist (e.g., an anti-complement factor D antibody, e.g., lampalizumab; Roche)); a visual cycle modifier (e.g., emixustat hydrochloride); squalamine (e.g., OHR-102; Ohr Pharmaceutical); vitamin and mineral supplements (e.g., those described in the Age-Related Eye Disease Study 1 (AREDS1; zinc and/or antioxidants) and Study 2 (AREDS2; zinc, antioxidants, lutein, zeaxanthin, and/or omega-3 fatty acids)); a cell-based therapy, for example, NT-501 (Renexus); PH-05206388 (Pfizer), huCNS-SC cell transplantation (StemCells), CNTO-2476 (Janssen), OpRegen (Cell Cure Neurosciences), or MA09-hRPE cell transplantation (Ocata Therapeutics); a tissue factor antagonist (e.g., h1-con1; Iconic Therapeutics); an alpha-adrenergic receptor agonist (e.g., brimonidine tartrate); a peptide vaccine (e.g., S-646240; Shionogi); an amyloid beta antagonist (e.g., an anti-beta amyloid monoclonal antibody, e.g., GSK-933776); an S1P antagonist (e.g., an anti-S1P antibody, e.g., iSONEP™; Lpath Inc); a ROBO4 antagonist (e.g., an anti-ROBO4 antibody, e.g., DS-7080a; Daiichi Sankyo); a lentiviral vector expressing endostatin and angiostatin (e.g., RetinoStat); and any combination thereof. In some instances, AMD therapeutic agents (including any of the preceding AMD therapeutic agents) can be co-formulated. For example, the anti-PDGFR antibody REGN2176-3 can be co-formulated with aflibercept (EYLEA®). In some instances, such a co-formulation can be administered in combination with an antibody of the invention. In some instances, the ocular disorder is AMD (e.g., wet AMD).

An antibody (e.g., a cysteine engineered anti-VEGF antibody) or an antibody conjugate (e.g., a monodisperse HA conjugate) of the invention can be administered in combination with LUCENTIS® (ranibizumab) for treatment of an ocular disorder (e.g., AMD, DME, DR, or RVO). LUCENTIS® (ranibizumab) may be administered, for example, at 0.3 mg/eye or 0.5 mg/eye by intravitreal injection, for example, every month. In some instances, the ocular disorder is AMD (e.g., wet AMD).

An antibody (e.g., a cysteine engineered anti-VEGF antibody) or an antibody conjugate (e.g., a monodisperse HA conjugate) of the invention can be administered in combination with EYLEA® (aflibercept) for treatment of an ocular disorder (e.g., AMD, DME, DR, or RVO). EYLEA® (aflibercept) may be administered, for example, at 2 mg/eye by intravitreal injection, for example, every four weeks (Q4W), or Q4W for the first three months, followed by injections once every two months for maintenance. In some instances, the ocular disorder is AMD (e.g., wet AMD).

An antibody (e.g., a cysteine engineered anti-VEGF antibody) or an antibody conjugate (e.g., a monodisperse HA conjugate) of the invention can be administered in combination with MACUGEN® (pegaptanib sodium) for treatment of an ocular disorder (e.g., AMD, DME, DR, or RVO). MACUGEN® (pegaptanib sodium) may be administered, for example, at 0.3 mg/eye by intravitreal injection every six weeks. In some instances, the ocular disorder is AMD (e.g., wet AMD).

An antibody (e.g., a cysteine engineered anti-VEGF antibody) or an antibody conjugate (e.g., a monodisperse HA conjugate) of the invention can be administered in combination with VISUDYNE® (verteporfin) in combination with photodynamic therapy for treatment of an ocular disorder (e.g., AMD, DME, DR, or RVO). VISUDYNE® can be administered, for example, by intravenous infusion at any suitable dose (e.g., 6 mg/m² of body surface area) and delivered once every three months (e.g., over 10 minutes of infusion). In some instances, the ocular disorder is AMD (e.g., wet AMD).

An antibody (e.g., a cysteine engineered anti-VEGF antibody) or an antibody conjugate (e.g., a monodisperse HA conjugate) of the invention can be administered in combination with a PDGF antagonist for treatment of an ocular disorder (e.g., AMD, DME, DR, or RVO). Exemplary PDGF antagonists which may be used in combination with an antibody of the invention include an anti-PDGF antibody, an anti-PDGFR antibody, a small molecule inhibitor (e.g., squalamine), an anti-PDGF-B pegylated aptamer such as FOVISTA® (E10030; Ophthotech/Novartis), or a dual PDGF/VEGF antagonist (e.g., a small molecule inhibitor (e.g., DE-120 (Santen) or X-82 (TyrogeneX)) or a bispecific anti-PDGF/anti-VEGF antibody). For example, FOVISTA® can be administered as an adjunct therapy to an antibody of the invention. FOVISTA® can be administered at any suitable dose, for example, from 0.1 mg/eye to 2.5 mg/eye, e.g., at 0.3 mg/eye or 1.5 mg/eye, for example, by intravitreal injection, for example every four weeks (04W). OHR-102 (squalamine lactate ophalmic solution, 0.2%) can be administered by eye drop, for example, twice daily. OHR-102 can be administered in combination with VEGF antagonists such as LUCENTIS® or EYLEA®. In some embodiments, an antibody conjugate of the invention can be administered in combination with OHR-102, LUCENTIS®, and/or EYLEA®. In some instances, the ocular disorder is AMD (e.g., wet AMD).

An antibody (e.g., a cysteine engineered anti-VEGF antibody) or an antibody conjugate (e.g., a monodisperse HA conjugate) of the invention can be administered in combination with RTH-258 for treatment of an ocular disorder (e.g., AMD, DME, DR, or RVO). RTH-258 can be administered, for example, by intravitreal injection or eye infusion. For intravitreal injection, RTH-258 can be administered at any suitable dose (e.g., 3 mg/eye or 6 mg/eye), for example, once every four weeks (04W) for the first three months as loading, followed by injection every 12 weeks (Q12W) or every eight weeks (Q8W) for maintenance. In some instances, the ocular disorder is AMD (e.g., wet AMD).

An antibody (e.g., a cysteine engineered anti-VEGF antibody) or an antibody conjugate (e.g., a monodisperse HA conjugate) of the invention can be administered in combination with abicipar pegol for treatment of an ocular disorder (e.g., AMD, DME, DR, or RVO). Abicipar pegol can be administered, for example, by intravitreal injection. Abicipar pegol can be administered at any suitable dose (e.g., 1 mg/eye, 2 mg/eye, 3 mg/eye, 4 mg/eye, or 4.2 mg/eye), for example, once every four weeks (04W) for the first three months as loading, followed by injection every 12 weeks (Q12W) or every eight weeks (Q8W) for maintenance. In some instances, the ocular disorder is AMD (e.g., wet AMD).

Any suitable DME and/or DR therapeutic agent can be administered in combination with an antibody (e.g., a cysteine engineered anti-VEGF antibody) an antibody conjugate (e.g., a monodisperse HA conjugate) of the invention for treatment of an ocular disorder (e.g., AMD, DME, DR, or RVO), including, but not limited, to a VEGF antagonist (e.g., LUCENTIS® or EYLEA®), a corticosteroid (e.g., a corticosteroid implant (e.g., OZURDEX® (dexamethasone intravitreal implant) or ILUVIEN® (fluocinolone acetonide intravitreal implant)) or a corticosteroid formulated for administration by intravitreal injection (e.g., triamcinolone acetonide)), or combinations thereof. In some instances, the ocular disorder is DME and/or DR.

An antibody (e.g., a cysteine engineered anti-VEGF antibody) or an antibody conjugate (e.g., a monodisperse HA conjugate) of the invention can be administered in combination with LUCENTIS® (ranibizumab) for treatment of DME and/or DR (e.g., NPDR or PDR). LUCENTIS® (ranibizumab) may be administered, for example, at 0.3 mg/eye or 0.5 mg/eye by intravitreal injection, for example, every four weeks (04W).

An antibody (e.g., a cysteine engineered anti-VEGF antibody) or an antibody conjugate (e.g., a monodisperse HA conjugate) of the invention can be administered in combination with EYLEA® (aflibercept) for treatment of DME and/or DR (e.g., NPDR or PDR). EYLEA® (aflibercept) may be administered, for example, at 2 mg/eye by intravitreal injection, for example, every four weeks (Q4W), or Q4W for the first five months, followed by injections once every eight weeks (Q8W) for maintenance.

An antibody (e.g., a cysteine engineered anti-VEGF antibody) or an antibody conjugate (e.g., a monodisperse HA conjugate) of the invention can be administered in combination with OZURDEX® (dexamethasone intravitreal implant) for treatment of DME and/or DR. OZURDEX® can be administered as a 0.7 mg dexamethasone intravitreal implant, which can be administered up to every six months.

An antibody (e.g., a cysteine engineered anti-VEGF antibody) or an antibody conjugate (e.g., a monodisperse HA conjugate) of the invention can be administered in combination with ILUVIEN® (dexamethasone intravitreal implant) for treatment of DME and/or DR. OZURDEX® can be administered as a 0.19 mg fluocinolone acetonide intravitreal implant, which can be eluted at a rate of 0.25 µg/day, and can last up to about 36 months.

In some cases, the TAO/PRN treatment regimen or TAE treatment regimen may be used to administer an AMD therapeutic agent (e.g., ranibizumab or aflibercept) in combination with an antibody (e.g., a cysteine engineered anti-VEGF antibody) or an antibody conjugate (e.g., a monodisperse HA conjugate) of the invention. For the TAO/PRN regimen, following initial intravitreal injections every four weeks (04W) (typically for about 3 months), the subject is monitored monthly or every other month (or at even longer intervals), with injections administered in the event of evidence of disease activity (e.g., a decline in visual acuity or fluid on optical coherence tomography (OCT)). For the TAE regimen, a subject may be treated every four weeks (04W), followed by extending the interval of treatment by a fixed number of weeks (e.g., +2 weeks) for each subsequent visit up to a maximal interval (e.g., every 6 weeks, ever 8 weeks, every 10 weeks, or every 12 weeks). The eye(s) may be observed and treated at each visit, even if there is no evidence of disease activity. If the macula appears wet (e.g., by OCT), the interval for injections can be shortened (e.g., −2 weeks) until the macula appears dry again. In some instances, the ocular disorder is AMD (e.g., wet AMD).

Such combination therapies noted above encompass combined administration (where two or more therapeutic agents are included in the same or separate formulations), and separate administration, in which case, administration of the antibody or antibody conjugate of the invention can occur prior to, simultaneously, and/or following, administration of the additional therapeutic agent or agents. In one embodiment, administration of the antibody or antibody conjugate and administration of an additional therapeutic agent occur within about one, two, three, four, or five months, or within about one, two or three weeks, or within about one, two, three, four, five, or six days, of each other.

An antibody (e.g., a cysteine engineered anti-VEGF antibody) or an antibody conjugate (e.g., a monodisperse HA conjugate) of the invention (and any additional therapeutic agent) for prevention or treatment of an ocular disease or condition can be administered by any suitable means, including but not limited to, for example, ocular, intraocular, and/or intravitreal injection, and/or juxtascleral injection, and/or subtenon injection, and/or superchoroidal injection, and/or topical administration in the form of eye drops and/or ointment. Such antibodies or antibody conjugates may be delivered by a variety of methods, for example, intravitreally as a device and/or a depot that allows for slow release of the compound into the vitreous, including those described in references such as Intraocular Drug Delivery, Jaffe, Jaffe, Ashton, and Pearson, editors, Taylor & Francis (March 2006). In one example, a device may be in the form of a mini pump and/or a matrix and/or a passive diffusion system and/or encapsulated cells that release the compound for a prolonged period of time (Intraocular Drug Delivery, Jaffe, Jaffe, Ashton, and Pearson, editors, Taylor & Francis (March 2006). Additional approaches which may be used are described in Section G below.

Formulations for ocular, intraocular, or intravitreal administration can be prepared by methods and using excipients known in the art. An important feature for efficient treatment is proper penetration through the eye. Unlike diseases of the front of the eye, where drugs can be delivered topically, retinal diseases typically benefit from a more site-specific approach. Eye drops and ointments rarely penetrate the back of the eye, and the blood-ocular barrier hinders penetration of systemically administered drugs into ocular tissue. Accordingly, a method of choice for drug delivery to treat retinal disease, such as AMD and CNV, is typically direct intravitreal injection. Intravitreal injections are usually repeated at intervals which depend on the patients condition, and the properties and half-life of the drug delivered. Additional approaches which may be used are described in Section G below.

The amount of antibody or antibody conjugate which will be effective in the treatment of a particular ocular disorder or condition will depend on the nature of the disorder or condition, and can be determined by standard clinical techniques. Where possible, it is desirable to determine the dose-response curve and the pharmaceutical compositions of the invention first in vitro, and then in useful animal model systems prior to testing in humans.

Additional suitable administration means include parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, for example, by injections, such as intravenous or subcutaneous injections, depending in part on whether the administration is brief or chronic. Various dosing schedules including but not limited to single or multiple administrations over various time-points, bolus administration, and pulse infusion are contemplated herein. In some instances, an antibody conjugate of the invention may be administered intravenously, intramuscularly, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, intraperitoneally, peritoneally, intraventricularly, subcutaneously, subconjunctivally, intravesicularly, mucosally, intrapericardially, intraumbilically, intraorbitally, orally, topically, transdermally, by inhalation, by injection, by implantation, by infusion, by continuous infusion, by localized perfusion bathing target cells directly, by catheter, by lavage, in cremes, or in lipid compositions For the prevention or treatment of disease, the appropriate dosage of an antibody (e.g., a cysteine engineered anti-VEGF antibody) or an antibody conjugate (e.g., a monodisperse HA conjugate) of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody (e.g., a cysteine engineered anti-VEGF antibody) or antibody conjugate (e.g., a monodisperse HA conjugate) is suitably administered to the patient at one time or over a series of treatments. Depending on the type and severity of the disease, about 1 µg/kg to 15 mg/kg (e.g., 0.1 mg/kg, 0.2 mg/kg, 0.4 mg/kg, 0.6 mg/kg, 0.8 mg/kg, 1 mg/kg, 2 mg/kg, 3 mg/kg, 4 mg/kg, 5 mg/kg, 6 mg/kg, 7 mg/kg, 8 mg/kg, 9 mg/kg, or 10 mg/kg) of antibody or antibody conjugate can be an initial candidate dosage for administration to the patient, whether, for example, by one or more separate administrations, or by continuous infusion. In some embodiments, the antibody or antibody conjugate used is about 0.01 mg/kg to about 45 mg/kg, about 0.01 mg/kg to about 40 mg/kg, about 0.01 mg/kg to about 35 mg/kg, about 0.01 mg/kg to about 30 mg/kg, about 0.01 mg/kg to about 25 mg/kg, about 0.01 mg/kg to about 20 mg/kg, about 0.01 mg/kg to about 15 mg/kg, about 0.01 mg/kg to about 10 mg/kg, about 0.01 mg/kg to about 5 mg/kg, or about 0.01 mg/kg to about 1 mg/kg. For antibody conjugates, the dosing may be based on the weight of the antibody component of the conjugate. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs.

In some embodiments, the methods may further comprise an additional therapy. The additional therapy may be radiation therapy, surgery, chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy may be a separate administration of one or more of the therapeutic agents described above.

It is understood that any of the above formulations or therapeutic methods may be carried out using an immunoconjugate of the invention in place of or in addition to an anti-VEGF antibody.

It is understood that any of the above formulations or therapeutic methods may be carried out using an antibody conjugate of the invention (e.g., any described herein, e.g., in Section G below).

F. Articles of Manufacture

In another aspect of the invention, an article of manufacture containing materials useful for the treatment and/or prevention of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody composition (e.g., an antibody (e.g., a cysteine engineered anti-VEGF antibody) or antibody conjugate thereof) of the invention. The label or package insert indicates that the composition is used for treating the condition of choice. Moreover, the article of manufacture may comprise (a) a first container with a composition contained therein, wherein the composition comprises an antibody or antibody composition thereof of the invention; and optionally (b) a second container with a composition contained therein, wherein the composition comprises an additional therapeutic agent. The article of manufacture in this embodiment of the invention may further comprise a package insert indicating that the composition(s) can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include any of the antibodies or antibody conjugates thereof described herein and/or any additional therapeutic agents.

G. Ocular Long-Acting Delivery Approaches

The invention provides compositions for treatment of ocular disorders, which may be used for long-acting delivery of antibodies (e.g., anti-VEGF antibodies (including any anti-VEGF antibody described herein, such as G6.31 AARR)) to the eye. For example, the invention provides antibody conjugates (e.g., monodisperse HA conjugates) that include an anti-VEGF antibody described herein (e.g., Fab, Fab-C, or cysteine engineered antibody (e.g., ThioFab) conjugates). The invention also provides devices that can be used for ocular administration of an antibody or antibody conjugate described herein. The invention further provides pharmaceutical compositions that include antibodies or antibody conjugates described herein. These compositions can be used in any of the therapeutic methods described herein, for example, methods of treating an ocular disorder (e.g., AMD (e.g., wet AMD), DME, DR (e.g., NPDR or PDR), or RVO (e.g., CRVO or BRVO)).

1. Antibody Conjugates

The invention provides antibody conjugates that include an antibody (e.g., an anti-VEGF antibody) and a monodisperse polymer covalently attached to the antibody. The antibody (e.g., the anti-VEGF antibody) may be covalently attached to the monodisperse polymer in an irreversible fashion or a reversible fashion. Any suitable monodisperse polymer may be used, including those described herein or others known in the art.

The invention provides an antibody conjugate that includes an antibody and a monodisperse polymer (e.g., a monodisperse HA polymer) covalently attached to the antibody. The polymer can have a polydispersity index (PDI) of about 1.1 or lower. It is to be understood that the PDI value can refer to the PDI value of the polymer used to prepare the antibody conjugate. For example, in some embodiments, the polymer has a PDI between 1.0 to about 1.1 (e.g., between 1 to about 1.1, between 1 to about 1.09, between 1 to about 1.08, between 1 to about 1.07, between 1 to about 1.06, between 1 to about 1.05, between 1 to about 1.04, between 1 to about 1.03, between 1 to about 1.02, between 1 to about 1.01, between 1 to about 1.005, between about 1.001 to about 1.1, between about 1.001 to about 1.1, between about 1.001 to about 1.09, between about 1.001 to about 1.08, between about 1.001 to about 1.07, between about 1.001 to about 1.06, between about 1.001 to about 1.05, between about 1.001 to about 1.04, between about 1.001 to about 1.03, between about 1.001 to about 1.02, between about 1.001 to about 1.01, between about 1.001 to about 1.005, between about 1.001 to about 1.004, between about 1.001 to about 1.003, between about 1.001 to about 1.002, between about 1.0001 to about 1.1, between about 1.0001 to about 1.09, between about 1.0001 to about 1.08, between about 1.0001 to about 1.07, between about 1.0001 to about 1.06, between about 1.0001 to about 1.05, between about 1.0001 to about 1.04, between about 1.0001 to about 1.03, between about 1.0001 to about 1.02, between about 1.0001 to about 1.01, between about 1.0001 to about 1.005, between about 1.0001 to about 1.004, between about 1.0001 to about 1.003, between about 1.0001 to about 1.002, or between about 1.0001 to about 1.005).

For example, in some embodiments, the monodisperse polymer (e.g., monodisperse HA polymer) has a PDI of 1.001, about 1.0001, about 1.00001, about 1.000001, about 1.0000001, or lower. In some embodiments, the monodisperse polymer (e.g., monodisperse HA polymer) has a PDI of 1.0, about 1.001, about 1.002, about 1.003, about 1.004, about 1.005, about 1.006, about 1.007, about 1.008, about 1.009, about 1.01, about 1.011, about 1.012, about 1.013, about 1.014, about 1.015, about 1.016, about 1.017, about 1.018, about 1.019, about 1.02, about 1.021, about 1.022, about 1.023, about 1.024, about 1.025, about 1.026, about 1.027, about 1.028, about 1.029, about 1.03, about 1.031, about 1.032, about 1.033, about 1.034, about 1.035, about 1.036, about 1.037, about 1.038, about 1.039, about 1.04, about 1.041, about 1.042, about 1.043, about 1.044, about 1.045, about 1.046, about 1.047, about 1.048, about 1.049, about 1.05, about 1.051, about 1.052, about 1.053, about 1.054, about 1.055, about 1.056, about 1.057, about 1.058, about 1.059, about 1.06, about 1.061, about 1.062, about 1.063, about 1.064, about 1.065, about 1.066, about 1.067, about 1.068, about 1.069, about 1.07, about 1.071, about 1.072, about 1.073, about 1.074, about 1.075, about 1.076, about 1.077, about 1.078, about 1.079, about 1.08, about 1.081, about 1.082, about 1.083, about 1.084, about 1.085, about 1.086, about 1.087, about 1.088, about 1.089, about 1.09, about 1.091, about 1.092, about 1.093, about 1.094, about 1.095, about 1.096, about 1.097, about 1.098, about 1.099, or about 1.1. In some embodiments, the polymer (e.g., HA polymer) has a PDI of about 1.001.

The monodisperse polymer may be a hydrophilic polymer or a hydrophobic polymer. It is to be understood that a hydrophilic polymer may be a water-soluble polymer. Any suitable hydrophilic polymer may be used, for example, a hydrophilic polymer described in International Patent Application Publication No. WO 2011/066417 and/or Pelegri-O'Day et al. J. Am. Chem. Soc. 136:14323-14332, 2014, which are incorporated herein by reference in their entirety. Exemplary, non-limiting hydrophilic polymers that can be used include hyaluronic acid (HA), polyethylene glycol (PEG; also known as poly(ethylene glycol)) (e.g., straight-chain PEG, branched PEG, comb-like PEG, and dendritic PEG), poly[ethylene oxide)-co-(methylene ethylene oxide)], poly(poly(ethylene glycol) methyl ether methacrylate) (pPEGMA), agarose, alginate, carageenans, carboxymethylcellulose, cellulose, cellulose derivatives, chitosan, chondroitin sulfate, collagen, dermatan sulfate, dextran, dextran sulfate, fibrin, fibrinogen, fibronectin, fucoidan, gelatin, glycosaminoglycans (GAGs), a glycopolymer, heparin, heparin sulfate, a highly-branched polysaccharide (e.g., a galactose dendrimer), keratan sulfate, methyl cellulose, hydroxypropylmethylcellulose (H PMC), poly(N-(2-hydroxypropyl) methacrylamide) (pHPMA), pectins, pectin derivatives, pentosane polysulfate, starch, hydroxylethyl starch (HES), styrene, vitronectin, poly(acrylic acid), poly(methacrylic acid), poly(acrylamide), poly(acrylic acid), poly(amines), poly(amino acids), poly(carboxybetaine) (PCB), polyelectrolytes, poly(glutamic acid) (PGA), poly(glycerol) (PG) (e.g., linear, midfunctional, hyperbranched, or linear hyperbranched PG), poly(maleic acid), poly(2-oxazoline) (POZ), poly(2-ethyl-2-oxazoline, polysialic acid (PSA), polystyrene, polystyrene derivatives (e.g., charged polystyrene derivatives), poly(styrenesulfonate-co-PEGMA), polyvinylpyrrolidone (PVP), poly(N-acryloylmorpholine) (pNAcM), and copolymers thereof. In some instances, the polymer is a hydrophobic polymer, for example, poly(lactic-co-glycolic acid) (PLGA), polylactide (PLA), and polyglycolide (PGA). The polymer may be biodegradable and/or biocompatible. In particular embodiments, the polymer is HA.

By way of example, the monodisperse polymer (e.g., HA polymer) may include any suitable number of monomers, for example, between 2 and about $1\times10^4$ monomers (e.g., about 10, about 50, about 100, about 200, about 300, about 400, about 500, about 600, about 700, about 800, about 900, about 1000, about 2000, about 3000, about 4000, about 5000, about 6000, about 7000, about 8000, about 9000, or about $1\times10^4$ monomers), or more. For example, the polymer (e.g., HA polymer) may include between about 50 and about 250 monomers, about 50 and about 500 monomers, between about 50 and about 1000 monomers, between about 50 and about 2000 monomers, between about 50 and about 3000 monomers, between about 50 and about 4000 monomers, between about 50 and about 5000 monomers, between about 50 and about 6000 monomers, between about 50 and about 7000 monomers, between about 50 and about 8000 monomers, between about 50 and about 9000 monomers, between about 50 and about 10000 monomers, between about 100 and about 250 monomers, about 100 and about 500 monomers, between about 100 and about 1000 monomers, between about 100 and about 2000 monomers, between about 100 and about 3000 monomers, between about 100 and about 4000 monomers, between about 100 and about 5000 monomers, between about 100 and about 6000 monomers, between about 100 and about 7000 monomers, between about 100 and about 8000 monomers, between about 100 and about 9000 monomers, between about 100 and about 10000 monomers, between about 250 and about 500 monomers, between about 250 and about 1000 monomers, between about 250 and about 2000 monomers, between about 250 and about 3000 monomers, between about 250 and about 4000 monomers, between about 250 and about 5000 monomers, between about 250 and about 6000 monomers, between about 250 and about 7000 monomers, between about 250 and about 8000 monomers, between about 250 and about 9000 monomers, between about 250 and about 10000 monomers. between about 500 and about 1000 monomers, between about 500 and about 2000 monomers, between about 500 and about 3000 monomers, between about 500 and about 4000 monomers, between about 500 and about 5000 monomers, between about 500 and about 6000 monomers, between about 500 and about 7000 monomers, between about 500 and about 8000 monomers, between about 500 and about 9000 monomers, or between about 500 and about 10000 monomers. In some instances, the polymer (e.g., HA polymer) may include about 500 monomers.

The invention provides an antibody conjugate that includes an antibody (e.g., an anti-VEGF antibody such as G6.31 AARR) covalently attached to a monodisperse HA polymer. Such antibody conjugates are sometimes referred to herein as "monodisperse HA conjugates." The monodisperse HA polymer can have a polydispersity index (PDI) of about 1.1 or lower. For example, in some embodiments, the monodisperse HA polymer has a PDI between 1.0 to about 1.1 (e.g., between 1 to about 1.1, between 1 to about 1.09, between 1 to about 1.08, between 1 to about 1.07, between 1 to about 1.06, between 1 to about 1.05, between 1 to about 1.04, between 1 to about 1.03, between 1 to about 1.02, between 1 to about 1.01, between 1 to about 1.005, between about 1.001 to about 1.1, between about 1.001 to about 1.1, between about 1.001 to about 1.09, between about 1.001 to about 1.08, between about 1.001 to about 1.07, between about 1.001 to about 1.06, between about 1.001 to about 1.05, between about 1.001 to about 1.04, between about 1.001 to about 1.03, between about 1.001 to about 1.02, between about 1.001 to about 1.01, between about 1.001 to about 1.005, between about 1.001 to about 1.004, between about 1.001 to about 1.003, between about 1.001 to about 1.002, between about 1.0001 to about 1.1, between about 1.0001 to about 1.09, between about 1.0001 to about 1.08, between about 1.0001 to about 1.07, between about 1.0001 to about 1.06, between about 1.0001 to about 1.05, between about 1.0001 to about 1.04, between about 1.0001 to about 1.03, between about 1.0001 to about 1.02, between about 1.0001 to about 1.01, between about 1.0001 to about 1.005, between about 1.0001 to about 1.004, between about 1.0001 to about 1.003, between about 1.0001 to about 1.002, or between about 1.0001 to about 1.005).

For example, in some embodiments, the monodisperse HA polymer has a PDI of 1.001, about 1.0001, about 1.00001, about 1.000001, about 1.0000001, or lower. In some embodiments, the monodisperse HA polymer has a PDI of 1.0, about 1.001, about 1.002, about 1.003, about 1.004, about 1.005, about 1.006, about 1.007, about 1.008, about 1.009, about 1.01, about 1.011, about 1.012, about 1.013, about 1.014, about 1.015, about 1.016, about 1.017, about 1.018, about 1.019, about 1.02, about 1.021, about 1.022, about 1.023, about 1.024, about 1.025, about 1.026, about 1.027, about 1.028, about 1.029, about 1.03, about 1.031, about 1.032, about 1.033, about 1.034, about 1.035, about 1.036, about 1.037, about 1.038, about 1.039, about 1.04, about 1.041, about 1.042, about 1.043, about 1.044, about 1.045, about 1.046, about 1.047, about 1.048, about 1.049, about 1.05, about 1.051, about 1.052, about 1.053, about 1.054, about 1.055, about 1.056, about 1.057, about 1.058, about 1.059, about 1.06, about 1.061, about 1.062, about 1.063, about 1.064, about 1.065, about 1.066, about 1.067, about 1.068, about 1.069, about 1.07, about 1.071, about 1.072, about 1.073, about 1.074, about 1.075, about 1.076, about 1.077, about 1.078, about 1.079, about 1.08, about 1.081, about 1.082, about 1.083, about 1.084, about 1.085, about 1.086, about 1.087, about 1.088, about 1.089, about 1.09, about 1.091, about 1.092, about 1.093, about 1.094, about 1.095, about 1.096, about 1.097, about 1.098, about 1.099, or about 1.1. In some embodiments, the monodisperse HA polymer has a PDI of about 1.001.

In some instances, the monodisperse HA polymer has a molecular weight of about 2.5 megadalton (MDa) or lower (e.g., about 2.5 MDa or lower, about 2.4 MDa or lower, about 2.3 MDa or lower, about 2.2. MDa or lower, about 2.1 MDa or lower, about 2.0 MDa or lower, about 1.9 MDa or lower, about 1.8 MDa or lower, about 1.7 MDa or lower, about 1.6 MDa or lower, about 1.5 MDa or lower, about 1.4 MDa or lower, about 1.3 MDa or lower, about 1.2 MDa or lower, about 1.1 MDa or lower, about 1.0 MDa or lower, about 900 kDa or lower, about 800 kDa or lower, about 700 kDa or lower, about 600 kDa or lower, about 500 kDa or lower, about 400 kDa or lower, about 300 kDa or lower, about 200 kDa or lower, or about 100 kDa or lower). In some instances, the HA polymer has a molecular weight of about 1 MDa or lower (e.g., about 1.0 MDa or lower, about 900 kDa or lower, about 800 kDa or lower, about 700 kDa or lower, about 600 kDa or lower, about 500 kDa or lower, about 400 kDa or lower, about 300 kDa or lower, about 200 kDa or lower, or about 100 kDa or lower). In some instances, the HA polymer has a molecular weight between about 25 kDa and about 2.5 MDa (e.g., between about 25 kDa and about 2.5 mDa, between about 25 kDa and about 2 MDa, between about 25 kDa and about 1.5 MDa, between about 25 kDa and about 1 MDa, between about 25 kDa and about 900 kDa, between about 25 kDa and about 800 kDa, between about 25 kDa and about 700 kDa, between about 25 kDa and about 600 kDa, between about 25 kDa and about 500 kDa, between about 100 kDa and about 2.5 mDa, between about 100 kDa and about 2 MDa, between about 100 kDa and about 1.5 MDa, between about 100 kDa and about 1 MDa, between about 100 kDa and about 900 kDa, between about 100 kDa and about 800 kDa, between about 100 kDa and about 700 kDa, between about 100 kDa and about 600 kDa, between about 100 kDa and about 500 kDa, between about 250 kDa and about 2.5 MDa, between about 250 kDa and about 2 MDa, between about 250 kDa and about 1.5 MDa, between about 250 kDa and about 1 MDa, between about 250 kDa and about 900 kDa, between about 250 kDa and about 800 kDa, between about 250 kDa and about 700 kDa, between about 250 kDa and about 600 kDa, between about 250 kDa and about 500 kDa, between about 500 kDa and about 2.5 MDa, between about 500 kDa and about 2 MDa, between about 500 kDa and about 1.5 MDa, between about 500 kDa and about 1 MDa, between about 500 kDa and about 900 kDa, between about 500 kDa and about 800 kDa, between about 500 kDa and about 700 kDa, between about 500 kDa and about 600 kDa, between about 1 MDa and about 2.5 MDa, between about 1 MDa and about 2 MDa, between about 1 MDa and about 1.5 MDa, between about 1 MDa and about 1.25 MDa, between about 1.25 MDa and about 2.5 MDa, between about 1.25 MDa and about 2 MDa, between about 1.25 MDa and about 1.5 MDa, between about 1.5 MDa and about 2.5 MDa, between about 1.5 MDa and about 2 MDa, between about 1.5 MDa and about 1.75 MDa, or between about 1.75 MDa and about 2.5 MDa).

In some instances, the monodisperse HA polymer has a molecular weight between about 25 kDa and about 500 kDa (e.g., between about 25 kDa and about 500 kDa, between about 25 kDa and about 450 kDa, between about 25 kDa and about 400 kDa, between about 25 kDa and about 350 kDa, between about 25 kDa and about 300 kDa, between about 25 kDa and about 300 kDa, between about 25 kDa and about 250 kDa, between about 25 kDa and about 200 kDa, between about 25 kDa and about 150 kDa, between about 25 kDa and about 100 kDa, between about 25 kDa and about 50 kDa, between about 40 kDa and about 500 kDa, between about 40 kDa and about 450 kDa, between about 40 kDa and about 400 kDa, between about 40 kDa and about 350 kDa, between about 40 kDa and about 300 kDa, between about 40 kDa and about 300 kDa, between about 40 kDa and about 250 kDa, between about 40 kDa and about 200 kDa, between about 40 kDa and about 150 kDa, between about 40 kDa and about 100 kDa, between about 40 kDa and about 50 kDa, between about 50 kDa and about 500 kDa, between about 50 kDa and about 450 kDa, between about 50 kDa and about 400 kDa, between about 50 kDa and about 350 kDa, between about 50 kDa and about 300 kDa, between about 50 kDa and about 300 kDa, between about 50 kDa and about 250 kDa, between about 50 kDa and about 200 kDa, between about 50 kDa and about 150 kDa, between about 50 kDa and about 100 kDa, between about 50 kDa and about 75 kDa, between about 100 kDa and about 500 kDa, between about 100 kDa and about 450 kDa, between about 100 kDa and about 400 kDa, between about 100 kDa and about 350 kDa, between about 100 kDa and about 300 kDa, between about 100 kDa and about 300 kDa, between about 100 kDa and about 250 kDa, between about 100 kDa and about 200 kDa, between about 100 kDa and about 150 kDa, between about 150 kDa and about 500 kDa, between about 150 kDa and about 450 kDa, between about 150 kDa and about 400 kDa, between about 150 kDa and about 350 kDa, between about 150 kDa and about 300 kDa, between about 150 kDa and about 300 kDa, between about 150 kDa and about 250 kDa, between about 150 kDa and about 200 kDa, between about 175 kDa and about 500 kDa, between about 175 kDa and about 450 kDa, between about 175 kDa and about 400 kDa, between about 175 kDa and about 350 kDa, between about 175 kDa and about 300 kDa, between about 175 kDa and about 300 kDa, between 175 200 kDa and about 250 kDa, between about 175 kDa and about 225 kDa, between about 200 kDa and about 500 kDa, between about 200 kDa and about 450 kDa, between about 200 kDa and about 400 kDa, between about 200 kDa and about 350 kDa, between about 200 kDa and about 300 kDa, between about 200 kDa and about 300 kDa, between about 200 kDa and about 250 kDa, or between about 200 kDa and about 225 kDa).

In some instances, the monodisperse HA polymer has a molecular weight between about 100 kDa and about 250 kDa (e.g., about 100 kDa, about 110 kDa, about 120 kDa, about 130 kDa, about 140 kDa, about 150 kDa, about 160 kDa, about 170 kDa, about 180 kDa, about 190 kDa, about 200 kDa, about 210 kDa, about 220 kDa, about 230 kDa, about 240 kDa, or about 250 kDa). In particular instances, the HA polymer has a molecular weight of about 200 kDa.

Any of the preceding molecular weights may be a weight-average molecular weight (also known as weight-average molar mass).

In some instances, any of the preceding monodisperse HA polymers is linear, i.e., not cross-linked.

In other instances, the invention provides an antibody conjugate that includes an antibody (e.g., an anti-VEGF antibody such as G6.31 AARR) covalently attached to a monodisperse PEG polymer. Such antibody conjugates are sometimes referred to as "PEG conjugates" herein. Any suitable monodisperse PEG polymer may be used. It is to be understood that monodisperse PEG polymers may have different PDI values as compared to monodisperse HA polymers. For example, commercially available PEG polymers may have a PDI below 1.1; thus, a monodisperse PEG polymer would be defined by a different range of PDI values compared to a monodisperse HA polymer. For example, a monodisperse PEG polymer may have a PDI from about 1 to about 1.02 (e.g., a PDI of 1, about 1.001, about 1.002, about 1.003, about 1.004, about 1.005, about 1.006, about 1.007, about 1.008, about 1.009, about 1.01, about 1.011, about 1.012, about 1.013, about 1.014, about 1.015, about 1.016, about 1.017, about 1.018, about 1.019, or about 1.02). The PEG may be a branched PEG, a star PEG, or a comb PEG. The PEG polymer may be, for example, a PEG tetramer, a PEG hexamer, or a PEG octamer. In some instances, the antibody conjugate includes an anti-VEGF antibody (e.g., an anti-VEGF antibody described herein, such as G6.31 AARR) covalently attached to a PEG dendrimer. PEG polymers are commercially available, for example, from JenKem Technology, Quanta BioDesign, NOF America Corporation, and other vendors.

In some instances, the monodisperse PEG polymer has a molecular weight between about 1 kDa and about 500 kDa (e.g., between about 1 kDa and about 500 kDa, between about 1 kDa and about 450 kDa, between about 1 kDa and about 400 kDa, between about 1 kDa and about 350 kDa, between about 1 kDa and about 300 kDa, between about 1 kDa and about 300 kDa, between about 1 kDa and about 250 kDa, between about 1 kDa and about 200 kDa, between about 1 kDa and about 150 kDa, between about 1 kDa and about 100 kDa, between about 1 kDa and about 50 kDa, between about 10 kDa and about 500 kDa, between about 10 kDa and about 450 kDa, between about 10 kDa and about 400 kDa, between about 10 kDa and about 350 kDa, between about 10 kDa and about 300 kDa, between about 10 kDa and about 300 kDa, between about 10 kDa and about 250 kDa, between about 10 kDa and about 200 kDa, between about 10 kDa and about 150 kDa, between about 10 kDa and about 100 kDa, between about 10 kDa and about 50 kDa, between about 20 kDa and about 500 kDa, between about 20 kDa and about 450 kDa, between about 20 kDa and about 400 kDa, between about 20 kDa and about 350 kDa, between about 20 kDa and about 300 kDa, between about 20 kDa and about 300 kDa, between about 20 kDa and about 250 kDa, between about 20 kDa and about 200 kDa, between about 20 kDa and about 150 kDa, between about 20 kDa and about 100 kDa, between about 20 kDa and about 75 kDa, between about 30 kDa and about 500 kDa, between about 30 kDa and about 450 kDa, between about 30 kDa and about 400 kDa, between about 30 kDa and about 350 kDa, between about 30 kDa and about 300 kDa, between about 30 kDa and about 300 kDa, between about 30 kDa and about 250 kDa, between about 30 kDa and about 200 kDa, between about 30 kDa and about 150 kDa, between about 40 kDa and about 500 kDa, between about 40 kDa and about 450 kDa, between about 40 kDa and about 400 kDa, between about 40 kDa and about 350 kDa, between about 40 kDa and about 300 kDa, between about 40 kDa and about 300 kDa, between about 40 kDa and about 250 kDa, between about 40 kDa and about 200 kDa, between about 50 kDa and about 500 kDa, between about 50 kDa and about 450 kDa, between about 50 kDa and about 400 kDa, between about 50 kDa and about 350 kDa, between about 50 kDa and about 300 kDa, between about 50 kDa and about 300 kDa, between 50 200 kDa and about 250 kDa, or between about 50 kDa and about 225 kDa).

In some instances, the monodisperse PEG polymer has a molecular weight between about 5 kDa and about 250 kDa (e.g., about 1 kDa, about 5 kDa, about 10 kDa, about 15 kDa, about 20 kDa, about 25 kDa, about 30 kDa, about 35 kDa, about 40 kDa, about 50 kDa, about 60 kDa, about 70 kDa, about 80 kDa, about 90 kDa, 100 kDa, about 110 kDa, about 120 kDa, about 130 kDa, about 140 kDa, about 150 kDa, about 160 kDa, about 170 kDa, about 180 kDa, about 190 kDa, about 200 kDa, about 210 kDa, about 220 kDa, about 230 kDa, about 240 kDa, or about 250 kDa). In particular instances, the PEG polymer has a molecular weight of about 20 kDa. In other instances, the PEG polymer has a molecular weight of about 40 kDa.

Any of the preceding molecular weights may be a weight-average molecular weight (also known as weight-average molar mass).

In some instances, the monodisperse PEG polymer is a PEG tetramer. PEG tetramers are commercially available, for example, NOF America SUNBRIGHT® PTE-400MA, PTE-200MA, PTE-100MA, and JenKem Technology USA 4 arm PEG maleimide (Cat. No. 4ARM-MAL). In some instances, the PEG tetramer has a pentaerythritol core. For example, in some instances, the PEG tetramer includes a structure of formula (I), wherein n is independently any suitable integer:

Formula I

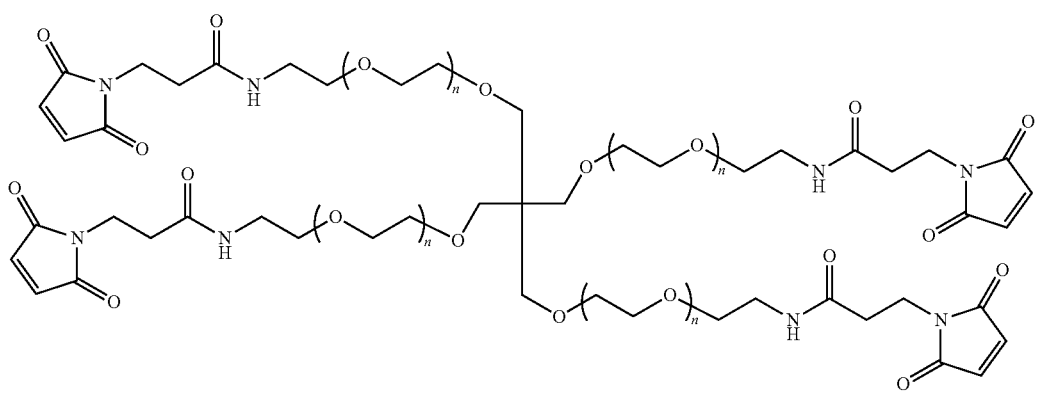

In another example, in some instances, the monodisperse PEG polymer is a PEG hexamer. PEG hexamers are commercially available, for example, JenKem Technology USA 6 arm PEG amine (Cat. No. 6ARM(DP)-NH2HCl), or PEG hexamers from Quanta BioDesign. In some instances, the PEG hexamer includes a dipentylerythritol core.

In some instances, the monodisperse PEG polymer is a PEG octamer. PEG octamers are commercially available, for example, NOF America SUNBRIGHT® HGEO series or JenKem Technology USA 8 arm PEG maleimide (Cat. No. 8ARM(TP)-MAL). In some instances, the PEG octamer may include a tripentaerithritol core. For example, in some instances, the PEG octamer includes a structure of formula (II), wherein n is independently any suitable integer:

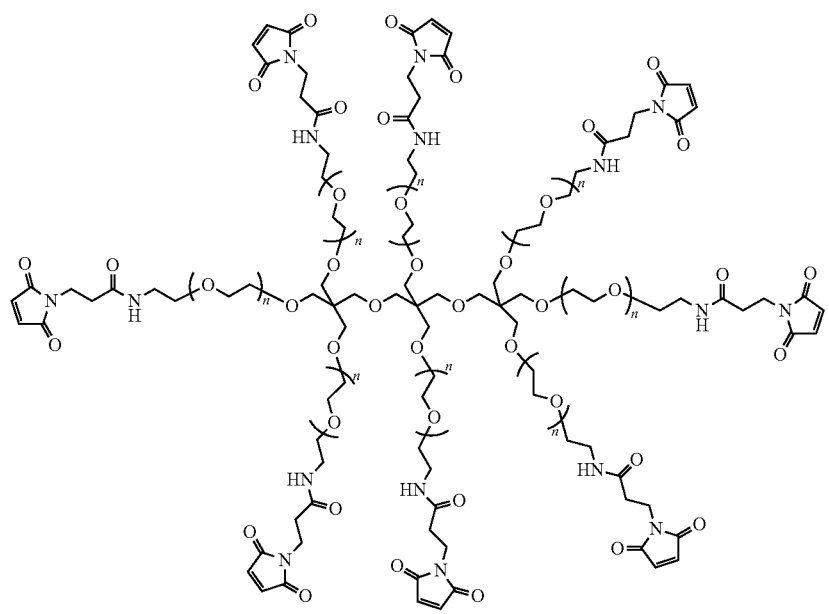

Formula II

In yet another example, in some instances, the PEG octamer includes a tripentaerythritol core.

It is to be understood that any suitable conjugation approach, including those described herein and others known in the art, may be used to conjugate an anti-VEGF antibody of the invention to a monodisperse polymer. For example, the monodisperse polymer may be conjugated to any suitable protein functional group, including a primary amine group, a carboxyl group, a sulfhydryl froup, or a carbonyl group. Any suitable chemical reactive group may be used to target the protein functional group, for example, carbodiimide (e.g., EDC), NHS ester, imidoester, pentafluorophenyl ester, hydroxymethyl phosphine, maleimide, haloacetyl (e.g., bromoacetyl or iodoacetyl), pyridyldisulfide, thiosulfonate, vinylsulfone, hydrazine, alkoxyamine, diazirine, aryl azide, isocyanate, or others known in the art. See, for example, Hermanson, *Bioconjugate Techniques, 3$^{rd}$ Edition*, 2013. In particular embodiments, HA (e.g., monodisperse HA) is modified with maleimide groups (HA-maleimide) and second, an antibody that includes a free thiol on a cysteine (e.g., Fab-C or a cysteine variant (e.g., a THIOMAB™ or ThioFab)) is reacted with HA-maleimide to form covalent HA-Fab conjugates, for example, as described in Example 1.

Any of the preceding antibody conjugates may have a hydrodynamic radius between about 5 nm and about 200 nm (e.g., about 5 nm, about 10 nm, about 20 nm, about 30 nm, about 40 nm, about 50 nm, about 60 nm, about 70 nm, about 80 nm, about 90 nm, about 100 nm, about 110 nm, about 120 nm, about 130 nm, about 140 nm, about 150 nm, about 160 nm, about 170 nm, about 180 nm, about 190 nm, or about 200 nm). In some instances, the antibody conjugate has a hydrodynamic radius between about 5 nm and about 150 nm (e.g., about 5 nm, about 10 nm, about 20 nm, about 30 nm, about 40 nm, about 50 nm, about 60 nm, about 70 nm, about 80 nm, about 90 nm, about 100 nm, about 110 nm, about 120 nm, about 130 nm, about 140 nm, or about 150 nm). In some instances, the antibody conjugate has a hydrodynamic radius between about 5 nm and about 100 nm (e.g., about 5 nm, about 10 nm, about 20 nm, about 30 nm, about 40 nm, about 50 nm, about 60 nm, about 70 nm, about 80 nm, about 90 nm, or about 100 nm). In some instances, the antibody conjugate has a hydrodynamic radius between about 5 nm and about 60 nm (e.g., about 5 nm, about 10 nm, about 20 nm, about 30 nm, about 40 nm, about 50 nm, or about 60 nm). In some instances, the antibody conjugate has a hydrodynamic radius between about 25 nm and about 35 nm (e.g., about 25 nm, about 26 nm, about 27 nm, about 28 nm, about 29 nm, about 30 nm, about 31 nm, about 32 nm, about 33 nm, about 34 nm, or about 35 nm). In some instances, the hydrodynamic radius is about 28 nm.

In some instances, the antibody conjugate has a hydrodynamic radius between about 10 nm and about 200 nm, between about 10 nm and about 180 nm, between about 10 nm and about 160 nm, between about 10 nm and about 140 nm, between about 10 nm and about 120 nm, between about 10 nm and about 100 nm, between about 10 nm and about 80 nm, between about 10 nm and about 60 nm, between about 10 nm and about 50 nm, between about 10 nm and about 40 nm, between about 10 nm and about 30 nm, between about 20 nm and about 200 nm, between about 20 nm and about 180 nm, between about 20 nm and about 160 nm, between about 20 nm and about 140 nm, between about 20 nm and about 120 nm, between about 20 nm and about 100 nm, between about 20 nm and about 80 nm, between about 20 nm and about 60 nm, between about 20 nm and about 50 nm, between about 20 nm and about 40 nm, between about 20 nm and about 30 nm, between about 30 nm and about 200 nm, between about 30 nm and about 180 nm, between about 30 nm and about 160 nm, between about 30 nm and about 140 nm, between about 30 nm and about 120 nm, between about 30 nm and about 100 nm, between about 30 nm and about 80 nm, between about 30 nm and about 60 nm, between about 30 nm and about 50 nm, between about 30 nm and about 40 nm, between about 40 nm and about 200 nm, between about 40 nm and about 180 nm, between about 40 nm and about 160 nm, between about 40 nm and about 140 nm, between about 40 nm and about 120 nm, between about 40 nm and about 100 nm, between about 40 nm and about 80 nm, between about 40 nm and about 60 nm, between about 40 nm and about 50 nm, between about 50 nm and about 200 nm, between about 50 nm and about 180 nm, between about 50 nm and about 160 nm, between about 50 nm and about 140 nm, between about 50 nm and about 120 nm, between about 50 nm and about 100 nm, between about 50 nm and about 80 nm, between about 50 nm and about 60 nm, between about 60 nm and about 200 nm, between about 60 nm and about 180 nm, between about 60 nm and about 160 nm, between about 60 nm and about 140 nm, between about 60 nm and about 120 nm, between about 60 nm and about 100 nm, or between about 60 nm and about 80 nm.

In any of the preceding antibody conjugates, the antibody may be an antibody fragment that binds VEGF, for example, an antibody fragment of an anti-VEGF antibody described herein that binds VEGF. In some instances, the anti-VEGF antibody is a cysteine engineered anti-VEGF antibody, as described herein (see, e.g., Section 1(8)(d) above). In some instances, the antibody fragment is selected from the group consisting of Fab, Fab', Fab-C, Fab'-SH, Fv, scFv, and (Fab')$_2$ fragments. In particular instances, the antibody fragment is an Fab, an Fab', or an Fab-C. In some instances, the antibody fragment is an Fab-C.

Any of the preceding antibody conjugates may have an ocular half-life that is increased relative to a reference antibody that is not covalently attached to the polymer (e.g., the hydrophilic polymer). In some instances, the ocular half-life is increased at least about 2-fold (e.g., about 2-fold, about 3-fold, about 4-fold, about 5-fold, about 6-fold, about 7-fold, about 8-fold, about 9-fold, about 10-fold, about 12-fold, about 14-fold, about 16-fold, about 18-fold, about 20-fold, or more) relative to the reference antibody. In some instances, the ocular half-life is increased at least about 4-fold relative to the reference antibody. In some instances, the ocular half-life is a vitreal half-life. In some instances, the reference antibody is identical to the antibody of the antibody conjugate. In other cases, the reference antibody is non-identical to the antibody of the antibody conjugate.

Any of the preceding antibody conjugates may have an ocular clearance that is that is decreased relative to a reference antibody that is not covalently attached to the polymer (e.g., the hydrophilic polymer). In some instances, the clearance is decreased at least about 2-fold (e.g., about 2-fold, about 3-fold, about 4-fold, about 5-fold, about 6-fold, about 7-fold, about 8-fold, about 9-fold, about 10-fold, about 12-fold, about 14-fold, about 16-fold, about 18-fold, about 20-fold, or more) relative to the reference antibody. In some instances, the clearance is decreased at least about 4-fold relative to the reference antibody. In some instances, the clearance is clearance from the vitreous. In some instances, the reference antibody is identical to the antibody of the antibody conjugate. In other cases, the reference antibody is non-identical to the antibody of the antibody conjugate.

In some instances, the time period between two intraocular administrations (e.g., by intravitreal injection) of any of the preceding antibody conjugates (e.g., HA conjugates) is at least 1 month, e.g., at least 1 month, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 15 weeks, at least 16 weeks, at least 20 weeks, at least 24 weeks, at least 28 weeks, at least 32 weeks, at least 36 weeks, at least 40 weeks, at least 44 weeks, at least 48 weeks, at least 52 weeks or more. In some cases, the maximum period between two intraocular administrations is no longer then four years, e.g., no longer than three years, no longer than two years, or no longer than one year. The antibody conjugate can be administered, for example, every two to twelve months, e.g., every four to ten months. In some instances, the antibody conjugate is administered every six months.

The invention also provides compositions (e.g., pharmaceutical compositions) that include any of the antibody conjugates described above. In certain embodiments, the composition comprises one or more additional compounds. In certain embodiments, the additional compound binds to a second biological molecule selected from the group consisting of IL-1β; IL-6; IL-6R; PDGF; angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor; ST-2 receptor; and proteins genetically linked to age-related macular degeneration (AMD) risk, such as complement pathway components C2, factor B, factor H, CFHR3, C3b, C5, C5a, and C3a; HtrA1; ARMS2; TIMP3; HLA; interleukin-8 (IL-8); CX3CR1; TLR3; TLR4; CETP; LIPC; COL10A1; and TNFRSF10A. In certain embodiments, the additional compound is an antibody or antigen-binding fragment thereof. For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof. In another example, in some instances, the additional compound is an anti-IL-6 antibody, for example, EBI-031 (Eleven Biotherapeutics; see, e.g., WO 2016/073890), siltuximab (SYLVANT®), olokizumab, clazakizumab, sirukumab, elsilimomab, gerilimzumab, OPR-003, MEDI-5117, PF-04236921, or a variant thereof. In a still further example, in some instances, the additional compound is an anti-IL-6R antibody, for example, tocilizumab (ACTEMRA®) (see, e.g., WO 1992/019579), sarilumab, vobarilizumab (ALX-0061), SA-237, or a variant thereof.

The invention further provides compositions (e.g., pharmaceutical compositions) that include any of the antibody conjugates described above and an additional VEGF antagonist.

2. Devices

Any of the antibodies (e.g., cysteine engineered anti-VEGF antibodies) or antibody conjugates (e.g., monodisperse HA conjugates) described herein can be administered to the eye using a port delivery device. A port delivery device is an implantable, refillable device that can release a therapeutic agent (e.g., an anti-VEGF antibody conjugate) over a period of months (e.g., 1, 2, 3, 4, 5, 6, 7, 8, 9, 10, 11, 12, or more months). Exemplary port delivery devices that may be used include those from ForSight Labs, LLC and/or ForSight VISION4, for example, as described in International Patent Application Publication Nos. WO 2010/

088548, WO2015/085234, WO 2013/116061, WO 2012/019176, WO 2013/040247, and WO 2012/019047, which are incorporated herein by reference in their entirety.

For example, the invention provides port delivery devices that include reservoirs containing any of the antibodies or antibody conjugates described herein. The port delivery device may further include a proximal region, a tubular body coupled to the proximal region in fluid communication with the reservoir, and one or more outlets in fluid communication with the reservoir and configured to release the composition into the eye. The tubular body may have an outer diameter configured to be inserted through an incision or opening in the eye of about 0.5 mm or smaller. The device may be about 1 mm to about 15 mm in length (e.g., about 1 mm, about 2 mm, about 4 mm, about 5 mm, about 6 mm, about 7 mm, about 9 mm, about 11 mm, about 13 mm, or about 15 mm in length). The reservoir may have any suitable volume. In some instances, the reservoir has a volume of about 1 µl to about 100 µl (e.g., about 1 µl, about 5 µl, about 10 µl, about 20 µl, about 50 µl, about 75 µl, or about 100 µl). The device or its constituent parts may be made of any suitable material, for example, polyimide.

In some instances, the port delivery device includes a reservoir containing any of the antibodies or antibody conjugates described herein and one or more additional compounds. In certain embodiments, the additional compound binds to a second biological molecule selected from the group consisting of IL-1β; IL-6; IL-6R; PDGF; angiopoietin; angiopoietin 2; Tie2; S1P; integrins $\alpha v\beta 3$, $\alpha v\beta 5$, and $\alpha 5\beta 1$; betacellulin; apelin/APJ; erythropoietin; complement factor D; TNFα; HtrA1; a VEGF receptor; ST-2 receptor; and proteins genetically linked to AMD risk, such as complement pathway components C2, factor B, factor H, CFHR3, C3b, C5, C5a, and C3a; HtrA1; ARMS2; TIMP3; HLA; IL-8; CX3CR1; TLR3; TLR4; CETP; LIPC; COL10A1; and TNFRSF10A. In certain embodiments, the additional compound is an antibody or antigen-binding fragment thereof. For example, in some instances, the additional compound is a bispecific antibody (e.g., an anti-VEGF/anti-Ang2 bispecific antibody, such as RG-7716 or any bispecific anti-VEGF/anti-Ang2 bispecific antibody disclosed in WO 2010/069532 or WO 2016/073157 or a variant thereof. In another example, in some instances, the additional compound is an anti-IL-6 antibody, for example, EBI-031 (Eleven Biotherapeutics; see, e.g., WO 2016/073890), siltuximab (SYLVANT®), olokizumab, clazakizumab, sirukumab, elsilimomab, gerilimzumab, OPR-003, MEDI-5117, PF-04236921, or a variant thereof. In a still further example, in some instances, the additional compound is an anti-IL-6R antibody, for example, tocilizumab (ACTEMRA®) (see, e.g., WO 1992/019579), sarilumab, vobarilizumab (ALX-0061), SA-237, or a variant thereof.

In some instances, the port delivery device includes any of the antibodies or antibody conjugates described herein and an additional VEGF antagonist.

III. EXAMPLES

The following are examples of methods and compositions of the invention. It is understood that various other embodiments may be practiced, given the general description provided above.

Example 1: Linear Hyaluronic Acid (HA) Antibody Conjugates Prepared from Monodisperse HA for Improved Stability Conjugation of Fabs to the biopolymer hyaluronic acid (HA) can significantly improve retention time of the Fab in the eye, for example, by slowing diffusion of the Fab and, thereby, clearance from the vitreous humor. A two step process has been employed for HA-Fab conjugate production: first, commercial HA is modified with maleimide groups (HA-maleimide) and second, Fab-C (Fab with a free thiol on cysteine) is reacted with HA-maleimide to form covalent HA-Fab conjugates.

Figure 1B:
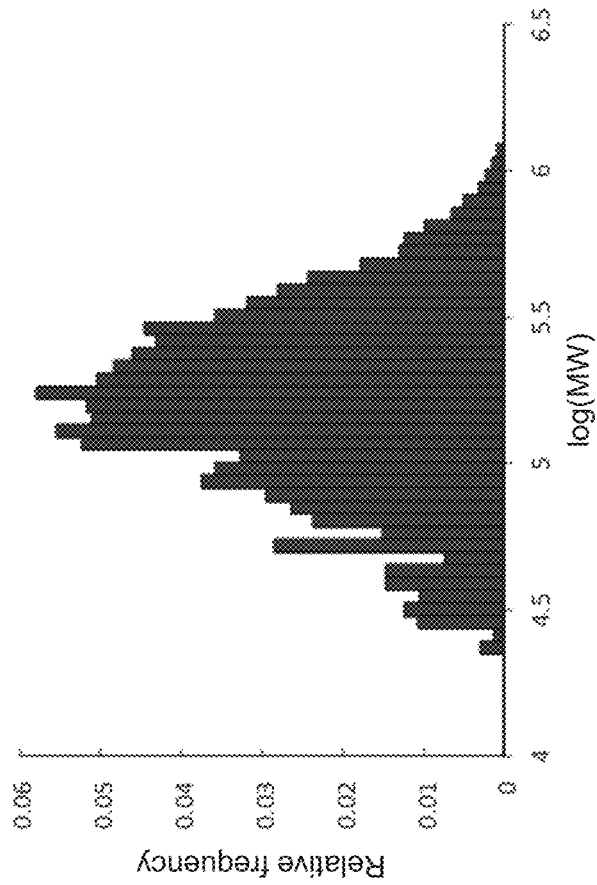
FIG. 1B is a graph showing a population distribution of the number of maleimides on a 200 kDa HA chain resulting from a Monte Carlo simulation of stochastic modification with each acid group having a 5% chance of modification.
Figure 1C:
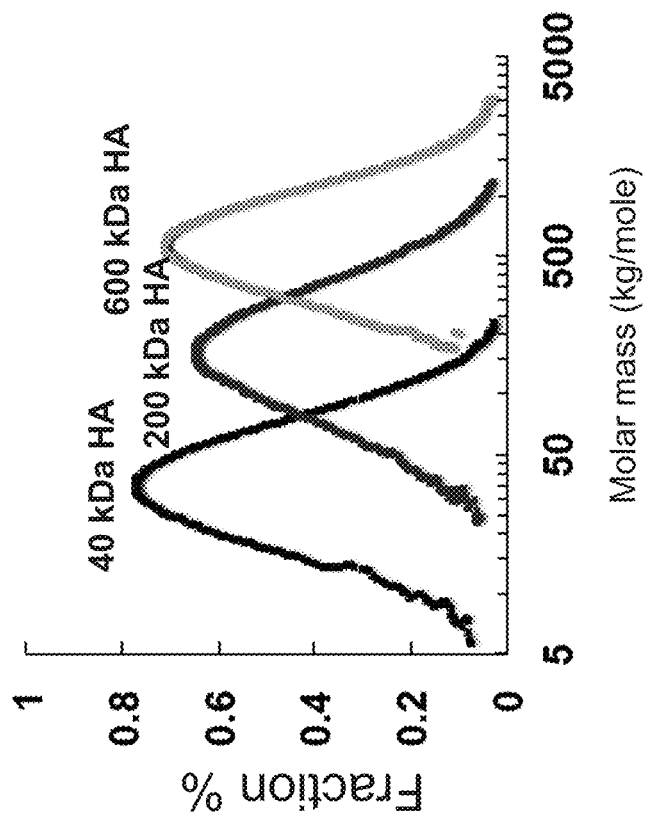
FIG. 1C is a graph showing the polydispersity of 40 kDa, 200 kDa, and 600 kDa HA polymers. The table below the graph shows the number-average molecular weight (Mn), weight-average molecular weight (Mw), polydispersity index (PDI), and molecular weight (MW) range (in terms of Mw) for the indicated samples.

When produced via typical means, HA-protein conjugates can have two orthogonal components of variability. The first source of variability is polydispersity, which is contributed by the polydispersity of the HA backbone (FIG. 1A). The second source is heterogeneity, which is contributed by differences in the number of Fab molecules attached to a given HA chain. This second source of variability is dictated by the stochastic nature of maleimide modification of HA chains in the first step of the HA conjugation process. FIG. 1B shows the results of a Monte Carlo simulation in which each acid group of a 200 kDa HA chain was given a 5% chance of being reacted with a maleimide-containing linker, repeated for 1000 independent HA chains. The results suggest that, although the mean number of maleimides per HA chain across the simulation was the expected value of 24.7, the absolute range was 11 to 42.

It can be desirable to maintain the physical and colloidal stability of antibody conjugates (e.g., antibody conjugates that include linear HA and the anti-VEGF antibody G6.31 AARR; referred to herein as HA-G6.31.AARR antibody conjugates) in aqueous phase and in vitreous humor. Based in part on the simulations described above, it is considered that HA backbone molecular weight and the Fab loading level could be important parameters for physical stability. The Fab loading level refers to the average number of antibody (e.g., G6.31.AARR) molecules attached to each HA chain and is expressed in terms of the percent of acid groups on the HA backbone that are covalently modified with a Fab moiety (each HA repeating unit contains one modifiable acid group on the glucuronic acid saccharide). While other parameters may contribute to conjugate stability (e.g. specific properties of the Fab including net charge, surface charge distribution, hydrophobicity), they are generally uncontrollable within the confines of this specific molecule.

To assess the impact of HA MW and Fab loading level on HA-G6.31.AARR physical stability, conjugates were prepared with three different HA starting MWs (approximately 40 kDa, 200 kDa and 600 kDa) and varying Fab loading levels, stressed under physiological conditions and monitored for physical stability over several months to mimic biological exposure.

(A) Materials and Methods
(i) Materials

Sodium hyaluronate (HA, Lifecore Biomedical, Chaska, MN) of three different molecular weights were used in this study. Their properties, as assessed by size exclusion chromatography in-line with refractive index and multi-angle light scattering detectors (SEC-RI-MALS), are summarized in Table 4. Mn indicates number average molecular weight; Mw indicates weight average molecular weight; PDI indicates polydispersity index; and RH indicates hydrodynamic radius. Table 5 shows data for Mn, Mw, and PDI of various polydisperse HA samples compared to a monodisperse sample as determined by SEC-RI-MALS. The data from Tables 4 and 5 are from two different lots of HA-200K, which had different polydispersity.

TABLE 4

Properties of HA used in this study

| Label Name | Mn, kDa | Mw, kDa | PDI | $R_H$, nm |
|---|---|---|---|---|
| 40K | 28.8 | 45.5 | 1.581 | 8.7 |
| 200K | 143.4 | 204.3 | 1.424 | 23.7 |
| 600K | 481.6 | 619.8 | 1.287 | 35.6 |

TABLE 5

Properties of polydisperse HA samples compared to a monodisperse sample

| Sample | Mn (kDa) | Mw (kDa) | PDI (Mw/Mn) |
|---|---|---|---|
| HA10K | 13.7 | 19.6 | 1.43 |
| HA20K | 21.0 | 32.9 | 1.57 |
| HA40K | 28.7 | 44.7 | 1.56 |
| HA100K | 66.0 | 107 | 1.62 |
| HA200K | 116 | 204 | 1.76 |
| HA350K | 206 | 314 | 1.53 |
| HA700K | 473 | 657 | 1.39 |
| Monodisperse HA150K | 137.2 | 137.3 | 1.001 |

(ii) Synthesis of Maleimide-Functionalized HA (HA-Mal)

HA was modified with maleimide groups using an aqueous reaction with the coupling reagent 4-(4,6-dimethoxy-1,3,5-triazin-2-yl)-4-methylmorpholinium chloride (DMTMM) and the linker N-(2-aminoethyl)maleimide trifluoroacetate salt (AEM). HA was dissolved in 100 mM 2-(N-morpholino)ethanesulfonic acid (MES) (pH 5.5) at 2.5 mg/mL and to this solution was added DMTMM and AEM under stirring. The amounts of DMTMM and AEM added varied and were selected to target different levels of maleimide functionalization ranging from 2 to 10%. The reaction was heated to 70° C. for 2 hours.

Excess AEM and DMTMM were removed from the reaction via a desalting procedure. A HIPREP™ 26/10 Desalting column was mounted on an AKTA™ purification system (GE Life Sciences) and equilibrated with 10 mM sodium acetate (pH 4.0) 150 mM NaCl. The reaction was injected neat onto the column, and the HA-mal peak was collected according to absorbance at 302 nm and concentrated to greater than 5 mg/mL using centrifugal ultrafiltration devices. The maleimide concentration in the HA-mal stock solution was measured by absorbance at 302 nm using a UV-visible spectrophotometer, and the molar ratio of maleimide groups per HA chain was assessed via size exclusion chromatography with multi-angle light scattering (SEC-MALS).

(iii) Conjugation of Fab-C to HA-Mal

A solution of Fab-C was pH adjusted to 6.5 using 1 M phosphate (pH 6.5) to a final phosphate concentration of 50 mM and ethylenediaminetetraacetic acid (EDTA) was spiked to a final concentration of 2.5 mM. The Fab-C solution was stirred and to it was added HA-mal diluted into reaction buffer comprised of 10 mM phosphate (pH 6.5), 150 mM NaCl, and 2.5 mM EDTA. The stoichiometry was set at 1.2 moles of Fab-C per mole of maleimide in the final reaction, and the volume was set to give a final protein concentration of 1 mg/mL. The conjugation reaction was carried out at room temperature under stirring. At 3 hours, mercaptoethanol was added at 2 moles per mole of maleimide to cap unreacted maleimide groups. After 30 minutes the reaction was diluted to less than 50 mM NaCl with 10 mM phosphate (pH 6.5).

Purification was carried out using size exclusion chromatography (SEC) to separate free Fab-C and Fab dimer from the conjugate. A HILOAD® 26/600 SUPERDEX® 200 µg column (GE Healthcare) was equilibrated with 10 mM HisHCl (pH 5.5) 150 mM NaCl and the reaction was injected neat. Peaks associated with conjugate, Fab dimer, and Fab monomer eluted separately and the conjugate peak was collected.

(iv) Analysis of HA-Fab Conjugates by SEC-RI-MALS

Residual free Fab content, total conjugate molar mass, and protein mass fraction were assessed by SEC-RI-MALS-QELS (a combination of size exclusion chromatography (SEC), refractive index (RI) multi-angle light scattering (MALS), and quasi-elastic light scattering (QELS)) on an Agilent 1200 HPLC with a Wyatt OPTILAB® T-rEX™ refractive index (RI) detector and Wyatt HELEOS™-II multi-angle light scattering (MALS) detector in-line. For SEC, two columns were run in series: ACCLAIM™ 7.8× 150 mm 1000 Å pore size followed by ACCLAIM™ 7.8× 150 mm 300 Å pore size with phosphate buffered saline (PBS) (pH 7.4) as the running buffer. A bovine serum albumin (BSA) control was used to normalize MALS detectors and correct for band broadening between detectors. Free Fab content was measured by integrating the UV $A_{280}$ peaks corresponding with Fab and HA-Fab conjugate. Conjugate molar mass was taken as the weight-average molecular weight (Mw) of the conjugate peak. Protein mass fraction was calculated using a protein conjugate analysis using the differential refractive index (dRI) and UV $A_{280}$ signals.

(v) HA-G6.31.AARR Conjugate Physiological Stress and Analysis

Purified conjugates were buffer exchanged into PBS and spiked with 2 mM sodium azide and 0.01% polysorbate 20 (PBSTN). The final concentrations were approximately 5 mg/mL on a Fab basis. The samples were sealed and incubated at 37° C. This condition serves as a surrogate for vitreous humor (mimicking the pH, temperature, and ionic strength of vitreous). The 5 mg/mL concentration represents a "stressful" concentration for assessing precipitation propensity in vitreous (2 mg dose in 4 mL human vitreous is equivalent to 0.5 mg/mL Fab). At specified time points, samples were withdrawn, diluted to 1 mg/mL in 10 mM HisHCl (pH 5.5) with 0.01% polysorbate 20 and 10% (w/v) trehalose, and assayed for soluble protein concentration ($A_{280}$), turbidity ($A_{450}$), SEC retention time, and molecular weight (Mn and Mw by SEC-RI-MALS as above).

(B) Results (i) Characterization of Materials

Table 6 lists the SEC-RI-MALS characterization results of the nine conjugates used in this study. The conjugates differ in both HA backbone MW (40 kDa, 200 kDa or 600 kDa) and Fab loading level. The sample names are given as HA backbone MW (kDA) followed by Fab loading level (%).

TABLE 6

SEC-RI-MALS characterization results of HA-G6.31.AARR starting materials

| Sample Name | Mn, kDa | Mw, kDa | Fab loading % |
|---|---|---|---|
| 40K 2.8% | 146 | 178.7 | 2.78 |
| 40K 2.9% | 149.4 | 182.4 | 2.85 |
| 40K 4.7% | 191.2 | 272.4 | 4.65 |
| 40K 6.3% | 305.9 | 354.8 | 6.31 |
| 200K 1.3% | 442.6 | 518.7 | 1.28 |
| 200K 2.5% | 664.3 | 813.1 | 2.45 |
| 200K 4.7% | 1106.2 | 1362.5 | 4.66 |
| 200K 6.2% | 1297.4 | 1739.3 | 6.17 |
| 600K 2.1% | 1730.6 | 2141.3 | 2.06 |

The polydispersity of HA-G6.31.AARR conjugates was evaluated experimentally using SEC-RI-MALS (FIG. 10). The polydispersity index was 1.58, 1.78, and 1.41 for HA40K, HA200K, and HA600K conjugates, respectively.

(ii) Conjugate Stability Under Physiological Stress

Figure 2:
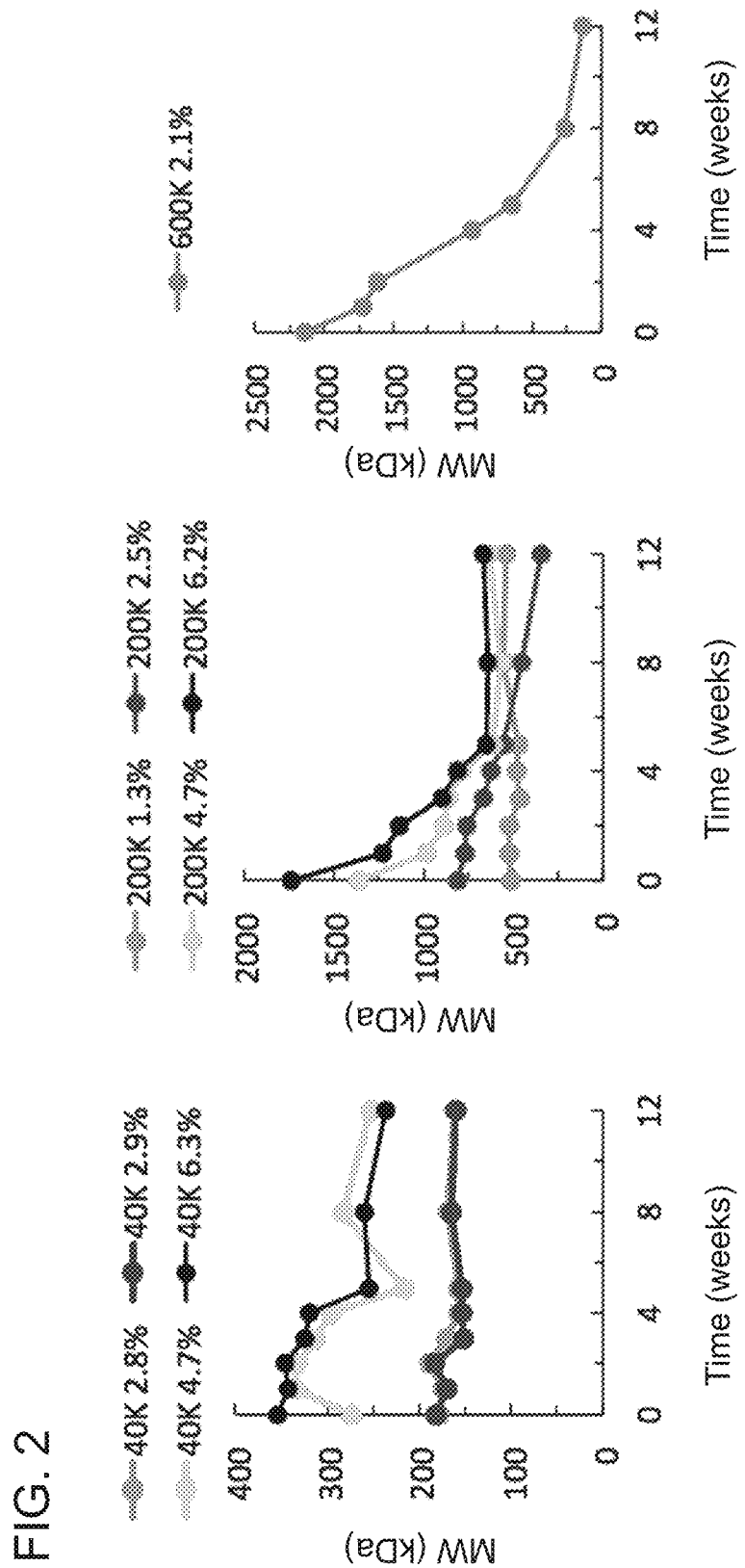
FIG. 2 is a series of graphs showing that HA-G6.31.AARR conjugates have differences in physical stability under physiologically relevant stress conditions as assessed by size exclusion chromatography (SEC) in-line with refractive index (RI) and multi-angle light scattering (MALS) detectors (SEC-RI-MALS). The series labels refer to the HA backbone molecular weight (40 kDa ("40K"); 200 kDa ("200K"); and 600 kDa ("600K") and Fab loading level.

Under physiological stress conditions, some HA-G6.31.AARR conjugates showed significant physical changes over extended incubation in PBSTN. This change is most clearly evidenced by shifts in the average molecular weight (Mw, weight-average molecular weight) with time, as shown in FIG. 2. While some samples did not change in Mw over the 12-week study, those that did all showed a decrease in Mw over time. The extent of Mw decrease was dependent both on the HA backbone molecular weight and the Fab loading level. In general, it was observed that precipitation occurred in samples where the HA molecular weight and Fab loading were higher.

Figure 3:
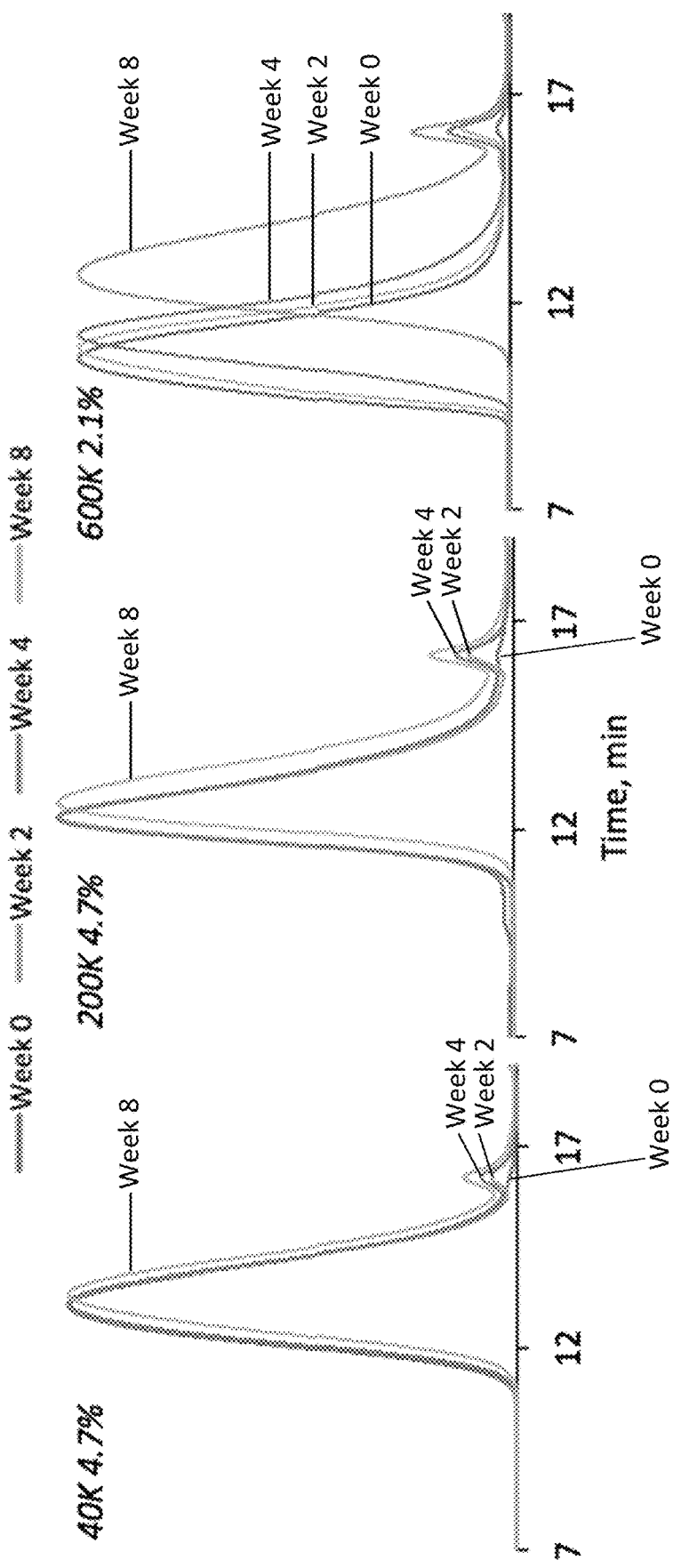
FIG. 3 is a series of graphs showing changes in SEC retention profiles over time for HA40K-G6.31.AARR-4.7% (left panel), HA200K-G6.31.AARR-4.7% (center panel), and HA600K-G6.31.AARR-2.1% (right panel), demonstrating that SEC retention times shift to later times (smaller hydrodynamic size), with the extent of this shift dependent on HA backbone molecular weight.

In order to understand this Mw shift, analysis of the SEC retention profiles of incubated HA-G6.31.AARR conjugates was performed. SEC retention times shifted to later times upon extended incubation, indicating that the average population of conjugate was becoming smaller progressively with time (FIG. 3). Because SEC retention time is defined entirely by the backbone HA molecular weight (and not by Fab loading), this observation indicated that either: (a) the entire population of conjugate molecules was getting smaller over time, or (b) a higher molecular weight subpopulation was precipitating out of solution, resulting in an apparent shift to smaller conjugates. These data are also summarized in Table 7, in which the differences between retention time at study start (T0) and week 12 are shown.

TABLE 7

SEC retention times of HA-G6.31.AARR stability samples at study start and at 12 weeks after exposure to physiological conditions

| Sample | Retention Time, T0, min | Retention Time, Week 12, min | Difference, min |
|---|---|---|---|
| 40K 2.8% | 13.272 | 13.267 | −0.005 |
| 40K 2.9% | 13.364 | 13.272 | −0.092 |
| 40K 4.7% | 13.125 | 13.349 | 0.224 |
| 40K 6.3% | 13.292 | 13.569 | 0.277 |
| 200K 1.3% | 11.986 | 11.848 | −0.138 |
| 200K 2.5% | 12.052 | 12.787 | 0.735 |
| 200K 4.7% | 12.31 | 12.448 | 0.138 |
| 200K 6.2% | 11.986 | 12.502 | 0.516 |
| 600K 2.1% | 10.692 | 13.627 | 2.935 |

These changes measured by SEC and MALS were paralleled by visual observations that higher HA backbone molecular weight and higher Fab loading samples contained visible precipitates at later time points. This observation supports the latter explanation for the observed shift in SEC retention profiles, i.e., that higher molecular weight subpopulations of HA were precipitating and leading to a shift in the average population remaining in solution.

Figure 4:
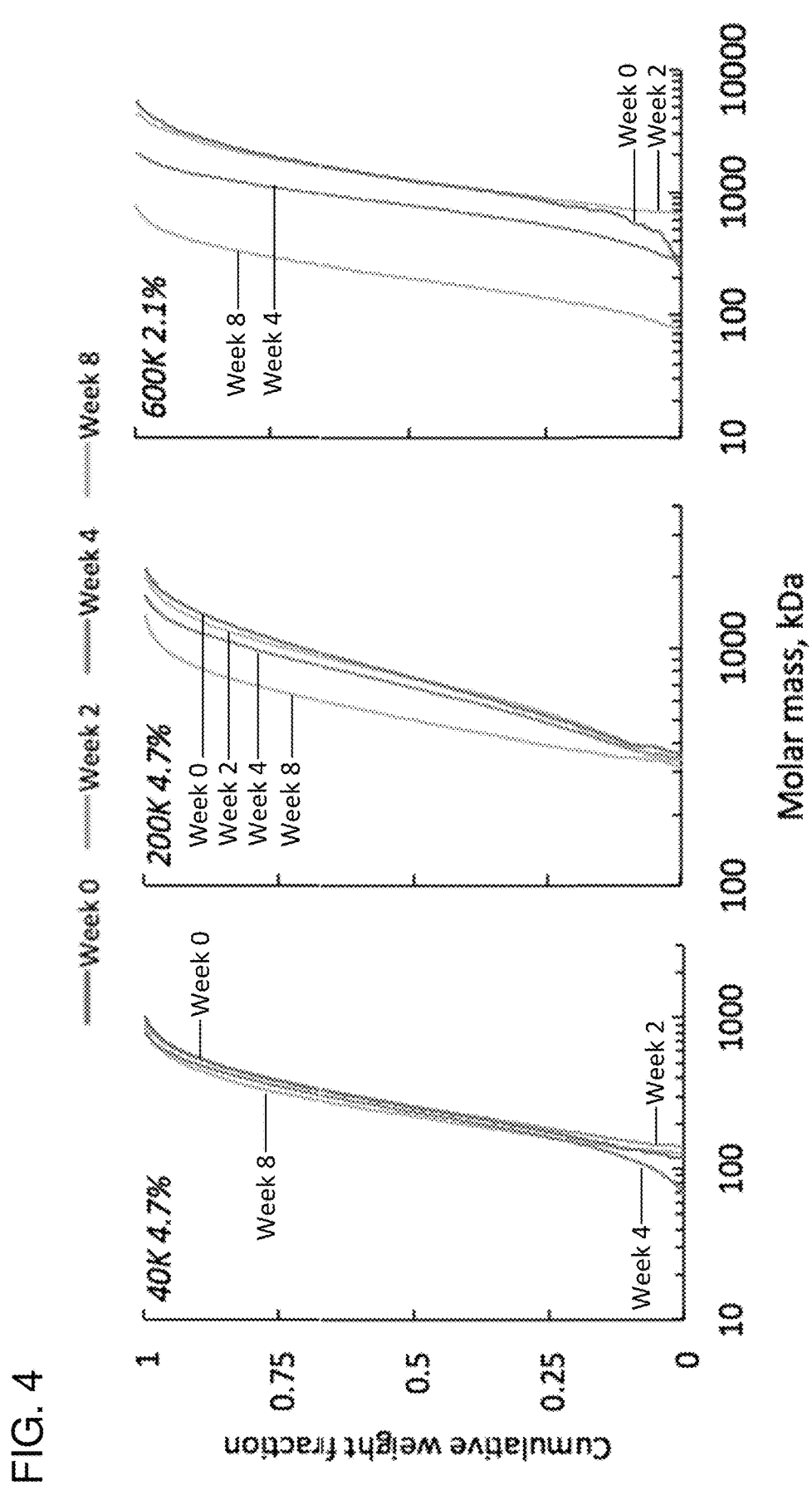
FIG. 4 is a series of graphs showing SEC-RI-MALS data plotted as cumulative weight fraction for HA40K-G6.31.AARR-4.7% (left panel), HA200K-G6.31.AARR-4.7% (center panel), and HA600K-G6.31.AARR-2.1% (right panel).

Further supporting this hypothesis is a re-analysis of SEC-RI-MALS data examining the distribution of HA-G6.31.AARR conjugates with respect to molecular weight, as shown in FIG. 4. For the 40K HA backbone sample (left panel), the overall distribution of conjugate molecules with respect to molecular weight did not change appreciably upon extended exposure to physiological conditions. For the 600K HA backbone sample (right panel), there was a continuous shift of all population fractions to smaller molecular weights, indicating that a broad population of conjugate molecules was precipitating out of solution. For the 200K HA backbone sample (center panel), the shift in population fractions occurred primarily in the higher molecular weight conjugate molecules. This indicates that in the 200K HA backbone sample there was a mixed population of relatively stable and unstable conjugate molecules. With time, the higher molecular weight conjugate molecules (relatively unstable subpopulation) precipitated out of solution, leaving only the relatively stable subpopulation remaining in solution.

(iii) Monodisperse HA Conjugates

Based on the understanding that within the polydisperse HA200K-G6.31.AARR population, only the higher MW subpopulations are driving the physical instability and precipitation, we hypothesized that switching from a polydisperse HA backbone to a monodisperse HA backbone could result in a more stable antibody conjugate.

Standard commercially-available HA is produced by a multi-step process in which: (a) HA is synthesized by bacterial fermentation resulting in extremely high MW HA (Mw 1-4 MDa), (b) the HA is purified from cell culture, and (c) HA is chemically degraded in a controlled manner resulting in random scission of HA molecules. This final step of the process is critical to the production of lower molecular weight HA that would otherwise not be feasible by fermentation alone. However, the random scission degradation process also results in a broad (i.e. polydisperse) distribution of HA molecular weights.

HA can also be synthesized at commercial scale via a synchronized chemo-enzymatic process (see Jing et al. *J. Biol. Chem.* 279:42345-42349, 2004; Jing et al. *Anal. Biochem.* 355:183-188, 2006; and U.S. Pat. No. 8,088,604, which are incorporated herein by reference in its entirety). In this process, a purified hyaluronan synthase enzyme is added to a mixture of small HA oligosaccharides (typically the HA tetramer, HA4) and the uridine diphosphate (UDP) saccharides UDP-glucuronic acid and UDP-N-acetylglucosamine. The hyaluronan synthase enzyme extends the oligosaccharide fragments using the available sugars in an alternating manner resulting in synchronized polymerization of HA. The molecular weight of the resulting HA polymer can be controlled by the ratio of HA substrate (e.g. HA4) to sugars in the starting reaction. The result of this process is highly monodisperse HA polymers.

Figure 5:
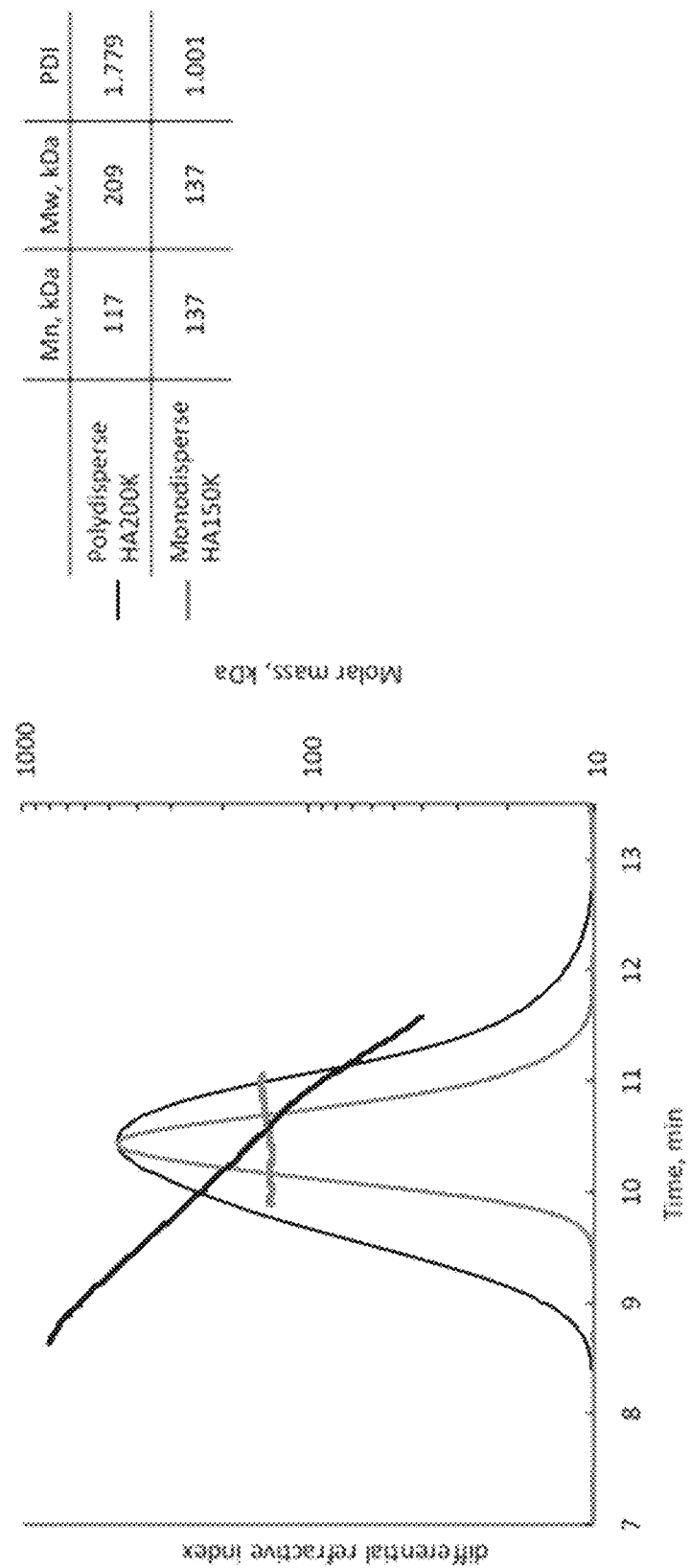
FIG. 5 is a graph showing the results of SEC-RI-MALS characterization of commercial polydisperse HA (black) and monodisperse HA (grey), demonstrating the difference in mass distributions between the two production techniques. The table in the right panel shows the Mn, Mw, and PDI values determined by this analysis.

For comparison, SEC-RI-MALS characterizations of polydisperse and monodisperse commercial HA of similar size were compared in FIG. 5. Most notable is the difference in polydispersity index, which was 1.779 for polydisperse HA200K and 1.001 for monodisperse HA150K. This lower level of polydispersity for monodisperse HA is considered to provide several key advantages from the perspective of HA-protein conjugates: (a) easier analytical characterization because elimination of the HA polydispersity leaves differences in protein loading levels as the only source of heterogeneity in the sample; (b) elimination of lower and higher molecular weight HA backbones in the overall population, which may eliminate the instability and precipitation observed in the higher molecular weight HA backbone subpopulations within HA-G6.31.AARR conjugates; and (c) potential reduction of the viscosity of the formulated HA-antibody conjugate.

Figure 6:
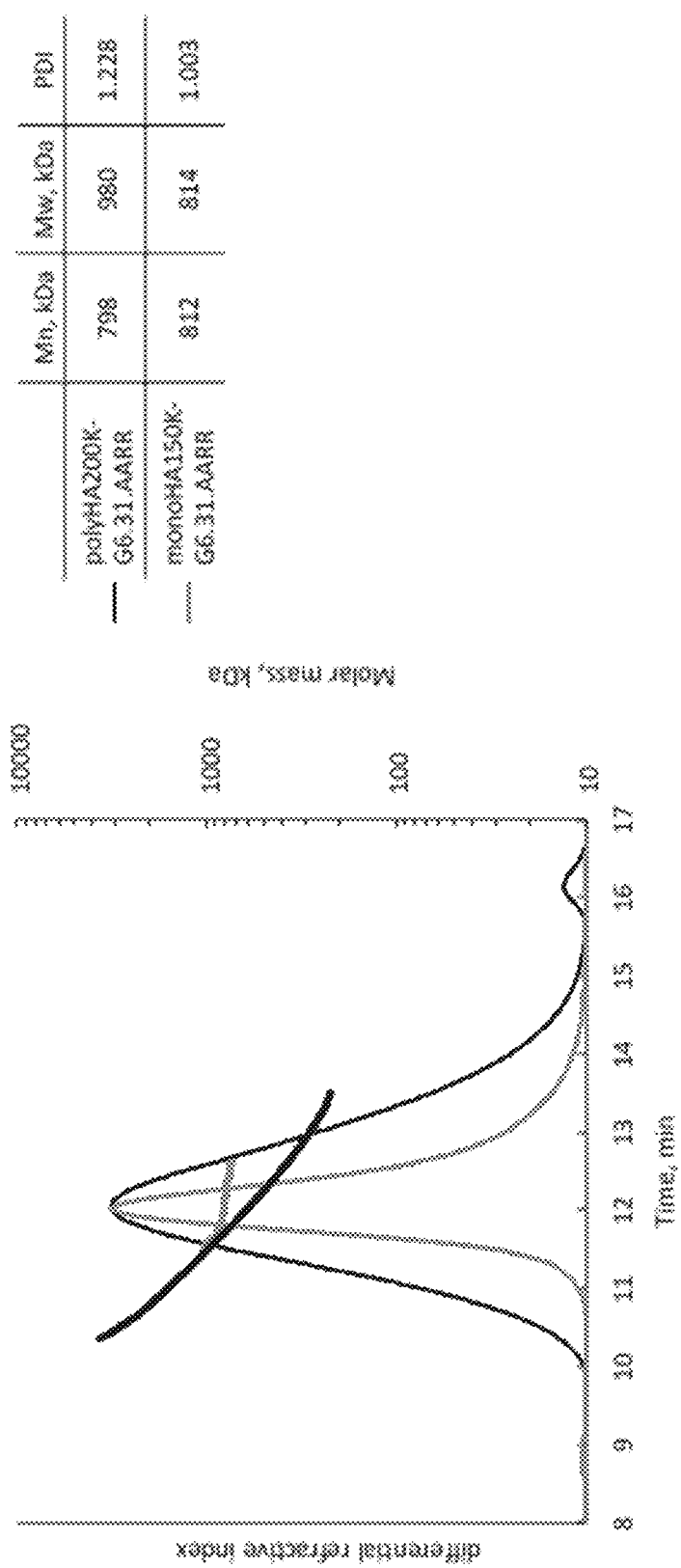
FIG. 6 is a graph showing the results of SEC-RI-MALS characterization of polydisperse HA200K-G6.31.AARR (black) and monodisperse HA150K-G6.31.AARR (grey), demonstrating the difference in mass distributions. The table in the right panel shows the Mn, Mw, and PDI values determined by this analysis.

In the context of using polydisperse and monodisperse HA starting materials to prepare G6.31.AARR conjugates, the same difference in polydispersity was observed: polydisperse HA200K-G6.31.AARR had a polydispersity index of 1.228, while monodisperse HA150K-G6.31.AARR had a polydispersity index of 1.003 (FIG. 6). It is expected that this monodispersity will improve HA-G6.31.AARR conjugate stability due to the absence of the higher HA backbone molecular weight subpopulation, which was presumed to be responsible for the instability and precipitation observed under physiological stress of polydisperse HA-G6.31.AARR conjugates.

Example 2: Optimized Fab Loading and Cysteine-Engineered Sites for Linear HA Antibody Conjugates Covalent conjugation of monoclonal antibodies (mAbs) or antibody fragments (Fabs) to a polymer scaffold can be performed through a wide variety of chemistries, ranging from amine chemistry (direct amidation through solvent-accessible lysine residues) to chemo-enzymatic conjugations using substrate-recognizing enzymes such as transglutaminase. Recently, thiol-maleimide conjugation chemistry has gained significant interest because it provides several key advantages over other approaches: (a) it is site-selective, reacting only to reduced, solvent-accessible cysteine residues, (b) it is an extremely rapid reaction, (c) maleimide-containing linkers are readily available and are typically easily accessed synthetically, (d) cysteine residues can typically be easily incorporated into a protein structure, and (e) the thiol-maleimide conjugation can be performed near neutral pH in aqueous conditions.

In order to produce a Fab that is amenable to maleimide conjugation, one strategy is to produce a Fab-C, in which the heavy chain sequence is extended through the hinge peptide to either the first or second hinge disulfide cysteine position and truncated at that cysteine residue (FIG. 7). In practice, this approach can potentially introduce a number of complications that impact conjugation to a polymer scaffold. The primary consequence of the spatial proximity of this free cysteine residue to the interchain disulfide bond is thiol scrambling, in which these three nearby cysteine residues can form three possible disulfide configurations. The three possible disulfide configurations are illustrated pictorially in FIGS. 8A-8C. In each configuration, a different cysteine residue is reduced, making it the potential site of conjugation to the maleimide-containing polymer backbone. The consequence of this is heterogeneity in the site of attachment between the Fab and the HA backbone, which may have consequences from the perspective of product quality, Fab stability, or safety of the conjugated material.

We hypothesized that relocating the free cysteine residue from the flexible, spatially proximal hinge sequence to a further surface location on the Fab could reduce or eliminate these conjugation variants. This approach is similar in nature to that employed by THIOMAB™ cysteine engineered monoclonal antibodies, in which surface residues are mutated to cysteines for later conjugation. In the Fab format, we term the surface-mutated cysteine-containing Fabs as "ThioFabs."

Protein-polymer conjugates produced using thiol-maleimide chemistry also can suffer from deconjugation of the protein from the polymer backbone through a reverse-Michael addition reaction. This can result in slow release of free protein from the polymer backbone in a pH- and temperature-dependent manner. This behavior is also influenced by the local chemical environment around the cysteine residue and the structure of the maleimide-containing linker (e.g. presence of electron-withdrawing groups or amines). Based on findings on reverse-Michael susceptibility of different cysteine locations in THIOMAB™ development (see Shen et al. *Nat. Biotechnol.* 30:184-189, 2012), we also predicted that moving the free cysteine from the hinge peptide to a surface location would reduce the rate of reverse-Michael free Fab release from a polymer backbone. We also investigated the rate of reverse-Michael deconjugation of a model polyethylene glycol (PEG)-maleimide polymer on Fab-C and ThioFab format molecules under physiological conditions.

(A) Materials and Methods (i) Materials

Lys-C enzyme was purchased from Promega (Catalog #V1671, Madison, WI), hyaluronidase (recombinant human PH20, also referred to as HAase) enzyme was purchased from Halozyme (San Diego, CA), N-ethylmaleimide (NEM) was purchased from Sigma Aldrich (St. Louis, MO). Defined methoxy polyethylene glycol maleimide (d-mPEG4-Mal, Part #10745) was purchased from Quanta Biodesign (Plain City, OH).

(ii) Limited Lys-C Digestion of G6.31.AARR.Fab-C

A limited Lys-C digest was performed on G6.31.AARR.Fab-C samples. Compared to a more traditional Lys-C digest of a protein, the "limited" Lys-C digest is performed with a reduced quantity of Lys-C enzyme and under non-denaturing conditions. This results in selective digestion of the hinge peptide portion of the G6.31.AARR.Fab-C molecule (KTHTC (SEQ ID NO: 61)), which is cleaved after the lysine residue. There were four samples of G6.31.AARR.Fab-C tested with different conditions: (a) +NEM, −Digest, (b) +NEM+Digest, (c) −NEM, +Digest, and (d) −NEM, −Digest.

For each sample, to 500 μg Fab-C in 500 μL of 10 mM histidine-acetate+150 mM sodium chloride (pH 5.5) was added 50 μl of 1M Tris+10 mM NEM (pH 7.5); the NEM was omitted for −NEM samples. Samples were incubated for 30 min at 37° C. to cap any free thiols. Lys-C enzyme was then added to +Lys-C samples at a mass ratio of 1:500 Lys-C:Fab-C. Samples were incubated for 30 min at 37° C. After digestion, samples were frozen to quench the reaction and analyzed by RP-UPLC-TOF.

(iii) Limited Lys-C Digestion of HA200K-G6.31.AARR

To 500 μg (on a protein basis) of HA200K-G6.31.AARR in 500 μL of 10 mM histidine-acetate+150 mM sodium chloride buffer (pH 5.5) was added 50 μL of 1M Tris (pH 7.5). Lys-C enzyme was added at a mass ratio of 1:500 Lys-C:Fab-C. Samples were incubated overnight at 37° C. After digestion, samples were frozen to quench the reaction and analyzed by RP-UPLC-TOF.

(iv) Hyaluronidase digest of HA200K-G6.31.AARR 500 μg (on a protein basis) of HA200K-G6.31.AARR was diluted in 500 μL of 10 mM histidine-acetate+150 mM sodium chloride (pH 5.5). HAase was added at 10 units (U) per 1 μg HA in the conjugate. The reaction mixture was incubated at 37° C. for 4 h. After digestion, samples were frozen to quench the reaction and analyzed by RP-UPLC-TOF.

(v) Reverse-Michael-mediated deconjugation of model G6.31.AARR-PEG conjugates G6.31.AARR.Fab-C, G6.31.AARR.A140C, G6.31.AARR.L174C, and G6.31.AARR.K149C were buffer exchanged into 10 mM phosphate (pH 6.5) 150 mM NaCl 2.5 mM EDTA at between 0.2 and 0.5 mg/mL and d-mPEG4-Mal was added at a 20-fold molar excess. The reaction was incubated at room temperature for 2 h followed by purification by desalting on PD-10 columns (GE Healthcare, Pittsburgh, PA) into PBS (pH 7.4). The conjugates were then concentrated to 1 mg/mL by centrifugal ultrafiltration and spiked with oxidized glutathione (GSSG) to a final concentration of 2 mM. Constructs were incubated at 37° C. and samples were pulled periodically for analysis by RP-UPLC-TOF.

(vi) Reverse-Phase Ultra Performance Liquid Chromatography Time of Flight (RP-UPLC-TOF) Mass Spectrometry (MS) Analysis Intact masses of samples were obtained by liquid chromatography-mass spectrometry (LC/MS) analysis using an Agilent 6230 electrospray ionization (ESI)-time-of-flight (TOF) mass spectrometer in line with an Agilent 1290 ultraperformance liquid chromatography (UPLC) system. Approximately 2.5 µg of protein was injected per sample and desalted by reverse-phase ultra performance liquid chromatography (RP-UPLC) for direct online MS analysis. The resulting spectra were deconvoluted to zero-charge state using the MassHunter workstation software/Qualitative Analysis (Agilent Technologies Inc., Santa Clara, CA).

(B) Results (i) Disulfide Status in G6.31.AARR.Fab-C

Figure 8C:
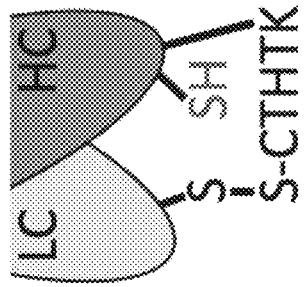
FIGS. 8A-8C are a series of schematic diagrams showing that the flexibility and spatial proximity of the hinge sequence can lead to rearrangement into three possible disulfide states leaving three different cysteine residues available for conjugation.
Figure 8B:
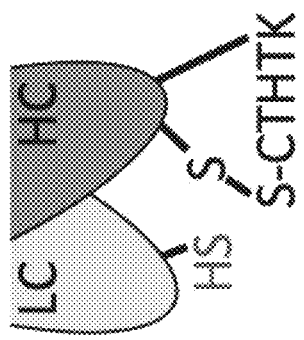
Figure 8A:
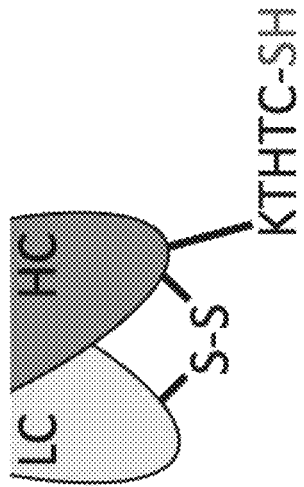

To confirm whether the three disulfide states shown in FIGS. 8A-8C exist in G6.31.AARR.Fab-C and are maintained in a dynamic thermodynamic equilibrium, we conducted a series of experiments using maleimide capping using NEM and limited Lys-C digests to probe both the instantaneous status of the three cysteine residues and their ability to re-arrange dynamically.

Figure 9:
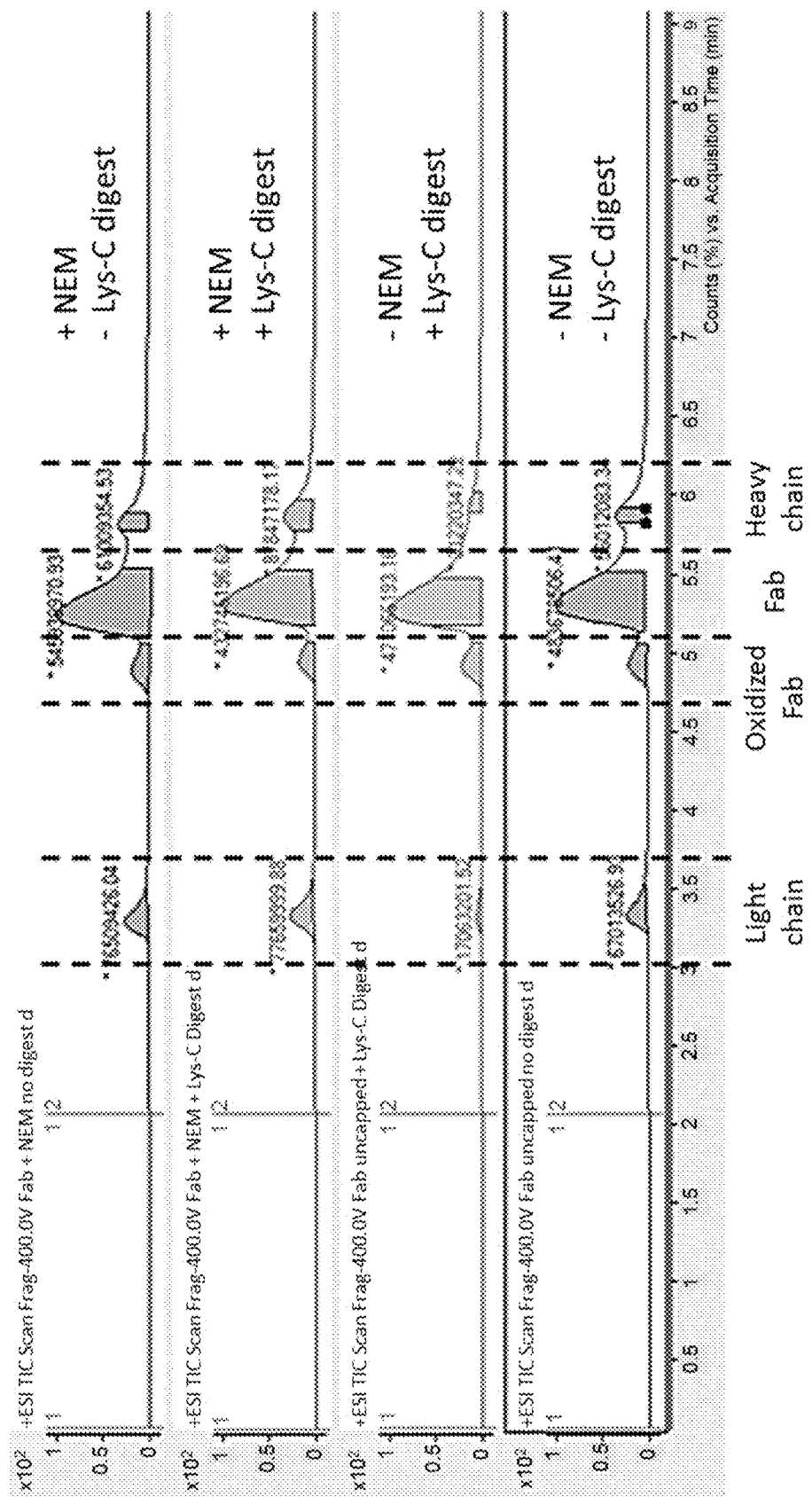
FIG. 9 shows a series of graphs showing the results of a series of maleimide capping and limited Lys-C digestion experiments performed on G6.31.AARR.Fab-C and analyzed by reverse phase ultra performance liquid chromatography time-of-flight (RP-UPLC-TOF) mass spectrometry. The numbers over the peaks are total ion counts for that peak and are a measure of peak area.

In the first experiment, G6.31.AARR.Fab-C was capped with NEM (freezing the disulfide status due to elimination of any free thiols) and then was subjected to a limited Lys-C digest, cleaving the heavy chain hinge peptide sequence before the intended free cysteine residue (FIG. 9, second chromatogram). Upon denaturing analysis on RP-UPLC-TOF, species associated with the three disulfide statuses presented in FIGS. 8A-8C were observed: (a) intact Fab minus hinge peptide (associated with FIG. 8A); (b) light chain plus NEM and cyclized heavy chain (associated with FIG. 8B); and (c) light chain plus hinge peptide and heavy chain minus hinge peptide plus NEM (associated with FIG. 8C). This experiment concretely demonstrated that G6.31.AARR.Fab-C does not exist in a homogeneous state but contains three distinct species with different disulfide configurations and, consequently, reactive cysteine residues.

In the second experiment, G6.31.AARR.Fab-C was subjected to a limited Lys-C digest without NEM capping, leaving the cysteines the possibility to rearrange dynamically (FIG. 9, third chromatogram). In this experiment, nearly all of the RP-UPLC-TOF analyzed protein was in the same state: Fab minus hinge peptide. Given the findings of the first experiment, this second set of data indicates that the three free cysteines rearranged dynamically and on a relatively fast time-scale (30 min experimental duration). After cleavage of the hinge peptide by Lys-C, the three possible disulfide states "scramble" between the three cysteine residues dynamically. If at some point in time the correct interchain disulfide is formed, the hinge peptide sequence is left to release into solution since it was previously cleaved by Lys-C. The result is that the sample is driven towards complete correctly-formed interchain disulfide through this rearrangement process.

These two experiments confirmed that G6.31.AARR.Fab-C can exist in three distinct states with regard to the three proximal cysteine residues and that their relative abundances are defined by a dynamic thermodynamic equilibrium. This latter finding is important because it indicates that no reprocessing step could completely eliminate the two incorrect disulfide configurations, since given any short period of time the three cysteines would re-scramble to form the three variants observed in the first experiment.

(ii) Conjugation Variants in HA-G6.31.AARR.Fab-C Conjugates

While these three disulfide variants exist in G6.31.AARR.Fab-C, it remained to be shown that they also exist as variants in HA-G6.31.AARR conjugates. To elucidate the exact location of conjugation of individual G6.31.AARR.Fab-C molecules to HA-maleimide, we used two enzymatic digestion procedures. The first, a limited Lys-C digest, cleaved G6.31.AARR at the hinge peptide preceding the intended free heavy chain cysteine residue. In correctly conjugated G6.31.AARR molecules, this treatment should release free intact G6.31.AARR into solution. However, analysis of digested samples by denaturing RP-UPLC-TOF identified an additional species in solution: free light chain plus cleaved hinge peptide (FIG. 10A). The presence of this species confirmed that a population of G6.31.AARR.Fab-C was conjugated to HA through the heavy chain cysteine normally occupied by the interchain disulfide, presumably originating from the disulfide variant depicted in FIG. 8C.

The second enzymatic digestion procedure kept all conjugations intact, but exhaustively digested the HA backbone using hyaluronidase (HAase). This permitted not only analysis of free molecules in solution, but also conjugated proteins with small HA oligosaccharides covalently attached. This method permitted direct observation of the conjugated species on an individual level. In this experiment, G6.31.AARR molecules correctly conjugated to HA through the intended heavy chain terminal cysteine were observed; however, direct evidence of conjugation through the disulfide variant depicted in FIG. 8B was also found. This was supported by two observations: (a) the presence of free cyclized heavy chain molecules in solution; and (b) the presence of HA oligosaccharides with covalently attached maleimide linker plus light chain (FIG. 10B). The presence of these species confirmed that a population of G6.31.AARR.Fab-C was conjugated to HA through the light chain cysteine normally occupied by the interchain disulfide, presumably originating from the disulfide variant depicted in FIG. 8B.

These two digestion experiments confirmed that disulfide rearrangement does lead to variations in the site of attachment between G6.31.AARR.Fab-C and HA-maleimide. This observation is expected to apply to any maleimide-containing polymer backbone used for conjugation and any Fab-C containing this configuration of three cysteine residues in close proximity.

(iii) Designing a Free Cysteine-Containing Fab for More Homogeneous Conjugation

The data described above show that three conjugation variants exist when attaching a Fab-C molecule to a maleimide-containing polymer backbone. This conjugation heterogeneity is caused by the existence of three distinct disulfide configurations in thermodynamic equilibrium, with each configuration leaving a different cysteine residue available to affect conjugation. That these three disulfide configurations are possible is likely influenced by several factors including the proximity of the intended free hinge cysteine residue to the interchain disulfide and the flexibility of the hinge peptide sequence to which the free cysteine is attached.

To avoid having the free cysteine scramble with the interchain disulfide, we envisioned moving the free cysteine further from the interchain disulfide. Therefore, we truncated the hinge sequence as typical for a standard Fab format molecule and mutated surface residues of the Fab to cysteine residues. The sites were chosen such that they were sufficiently far from the HVRs so as not to negatively impact antigen binding and were sufficiently far from the interchain disulfide to prevent scrambling.

For an initial screening study, three locations were chosen based on previous reports from THIOMAB™ development to meet these criteria: LC-K149 (EU numbering), HC-A140 (EU numbering), and HC-L174 (EU numbering). Each site was mutated to a cysteine residue and the hinge peptide was terminated immediately before the first hinge disulfide cysteine (i.e., KTHT; SEQ ID NO: 87).

Figure 11:
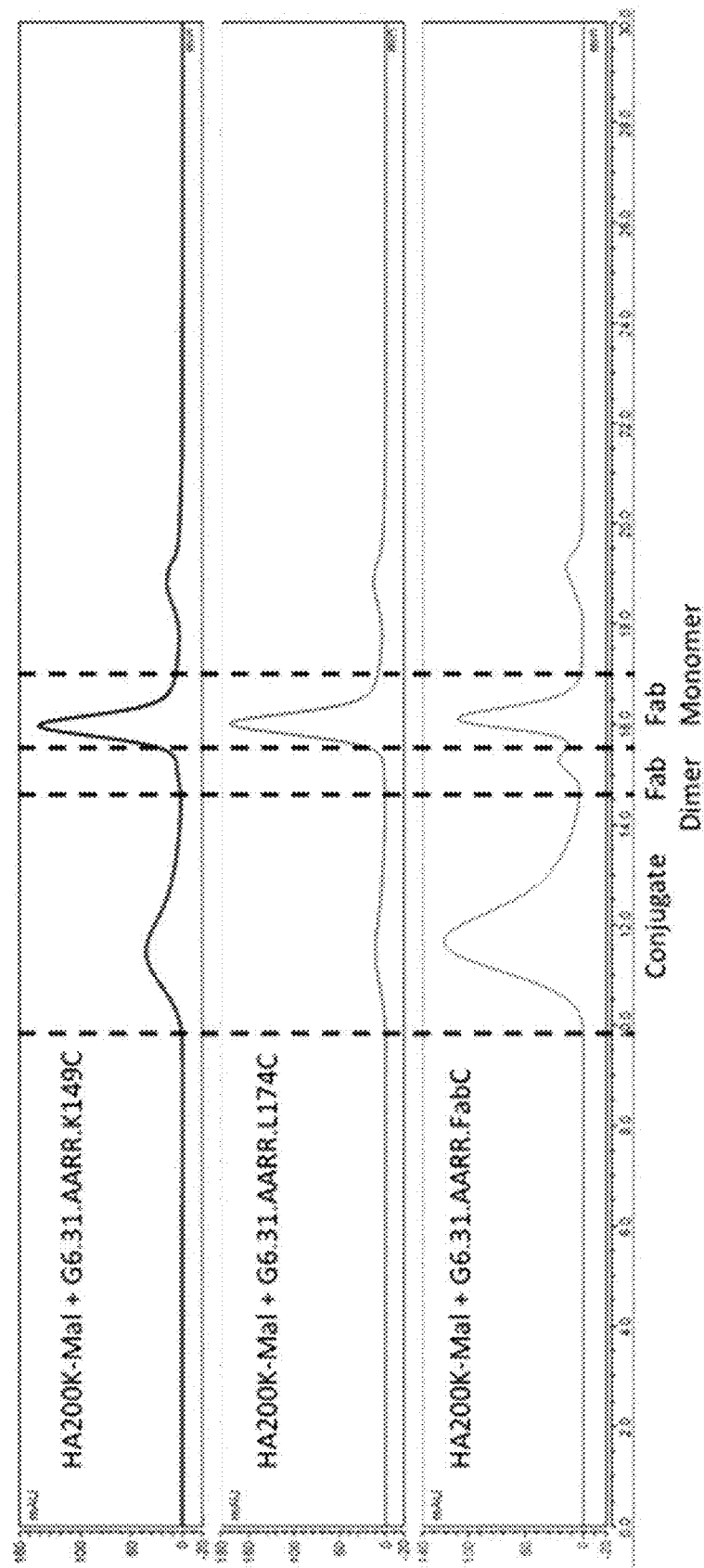
FIG. 11 is a series of graphs showing that conjugation of G6.31.AARR ThioFabs to HA200K-maleimide proceeded normally compared to G6.31.AARR.Fab-C, although the conversion of Fab to conjugate was lower for the ThioFab samples.

To confirm that these cysteine sites were still reactive to HA-maleimide, we performed pilot conjugations under typical conditions (10 mM phosphate (pH 6.5), 150 mM NaCl, and 2.5 mM EDTA) and assessed the products by SEC-RI-MALS after overnight incubation. Conjugation proceeded normally with generation of HA-G6.31.AARR conjugates at the correct retention time compared to a G6.31.AARR.Fab-C conjugation reaction control (FIG. 11). The only major difference noted in the ThioFab samples was lower conversion of Fab to conjugate. This is likely caused by the relatively low pH of the conjugation reaction (pH 6.5), which may be better suited to the pKa of the hinge cysteine compared to that of the ThioFab engineered cysteine residues. It is expected that increasing the pH of the conjugation reaction will improve yields for the ThioFab conjugations.

(iv) Reverse-Michael Addition Susceptibility of Fab-C and ThioFab Formats

Figure 12:
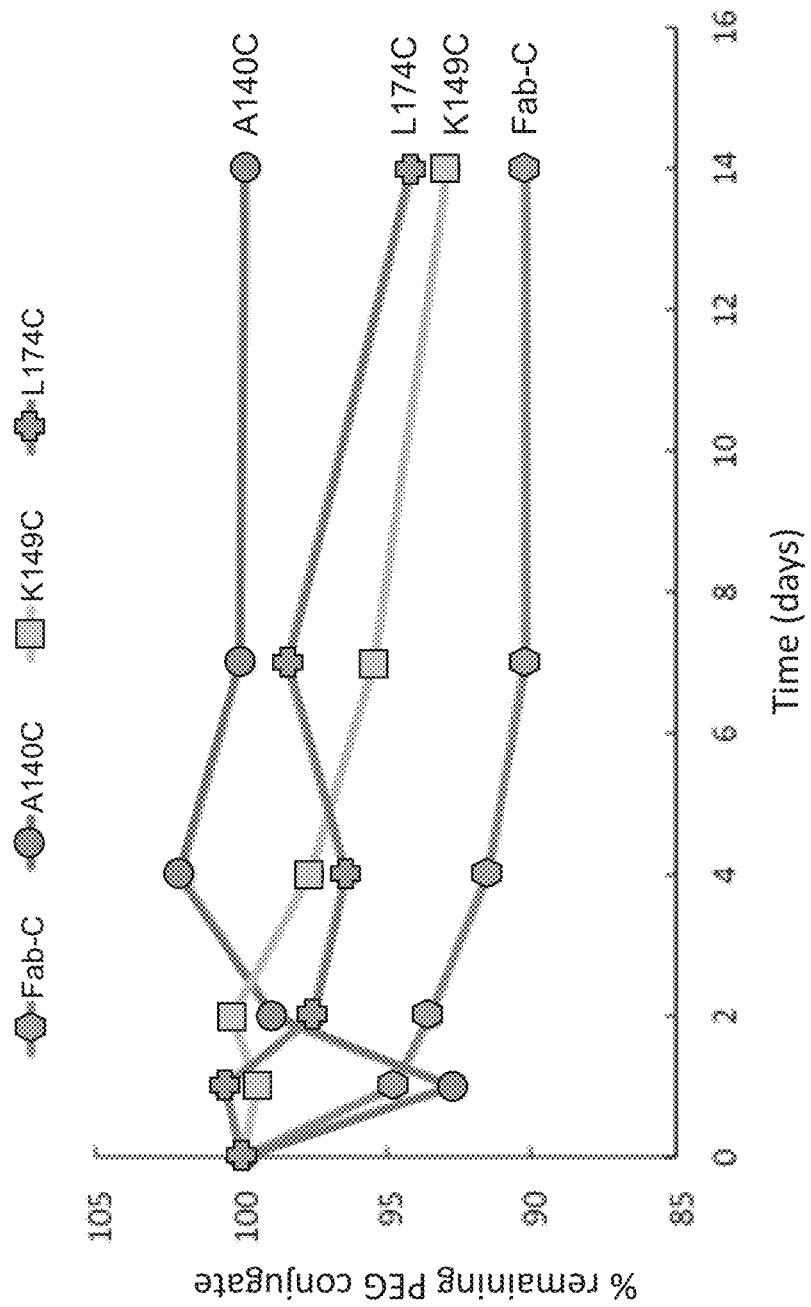
FIG. 12 is a graph showing deconjugation of a model polyethylene glycol (PEG)-maleimide polymer from G6.31.AARR of different formats in PBS+2 mM oxidized glutathione (GSSG) at 37° C. as assessed by RP-UPLC-TOF.
Figure 14:
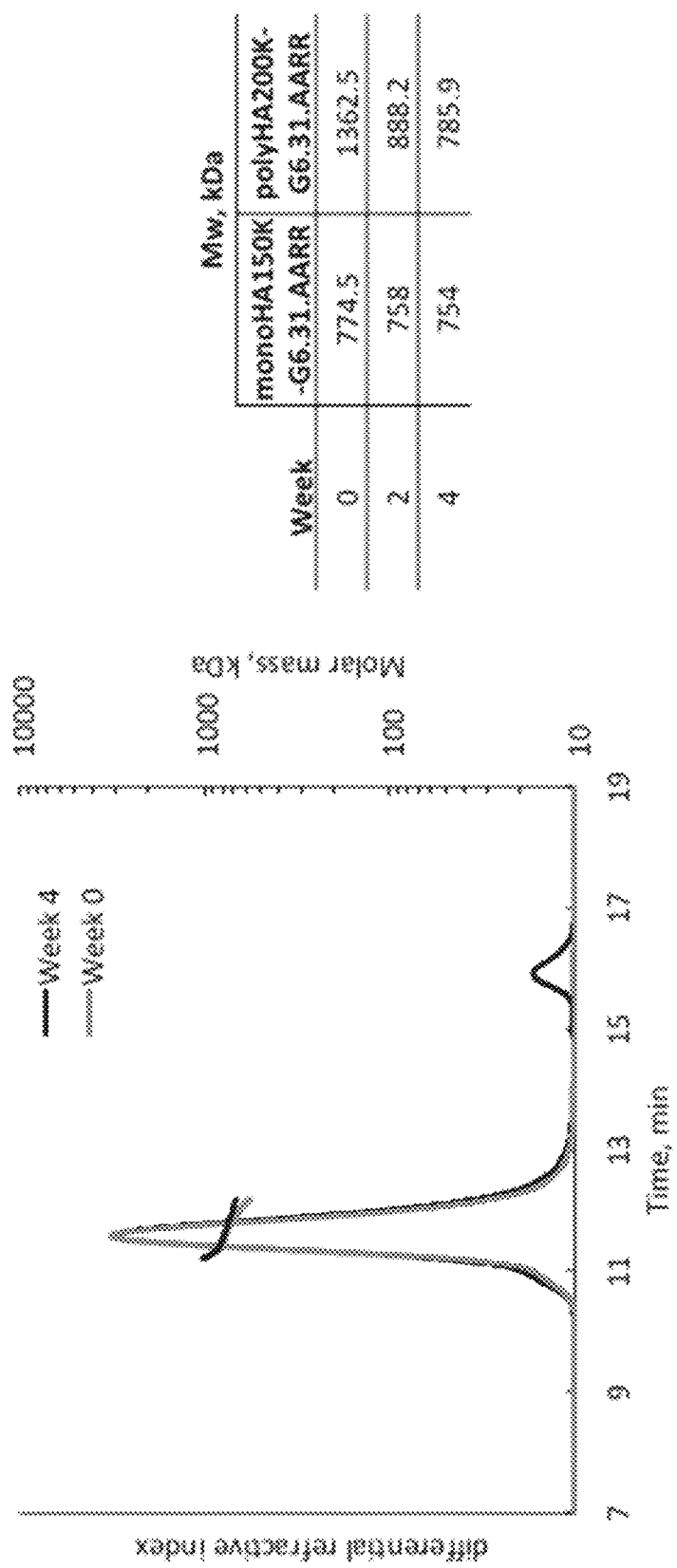
FIG. 14 is a graph showing that HA-G6.31.AARR conjugates produced from monodisperse HA show improved physical stability under physiological stress at four weeks compared to HA-G6.31.AARR conjugates of similar size produced from polydisperse HA. The table in the right panel shows Mw (kDa) at weeks 0, 2, and 4.

G6.31.AARR in Fab-C and ThioFab formats were conjugated to model PEG-maleimide constructs and incubated in PBS at 37° C. with GSSG to act as a free thiol trap (i.e., preventing reverse-Michael addition of released free thiol with PEG-maleimide) followed by periodic analysis by RP-UPLC-TOF. In Fab-C-PEG constructs, significant reverse-Michael deconjugation was observed over the first seven days, resulting in a 9.8% loss of intact conjugate (FIG. 12). ThioFab conjugates showed variable levels of improvement over Fab-C with the A140C variant showing nearly no deconjugation out to 14 days, the L174C variant showing 5.9% deconjugation, and the K149C variant showing 7.1% deconjugation over the same time. These data suggest that cysteine mutation variants may be protective against reverse-Michael-mediated protein deconjugation and may provide a significant advantage over the Fab-C format in retaining intact protein-polymer conjugates.

Example 3: Exemplary Anti-VEGF Antibodies for Use in the Antibody Conjugates of the Invention Any of the anti-VEGF antibodies described herein can be used to prepare antibody conjugates as described in Examples 1 and 2. For example, any anti-VEGF antibody described in International Patent Application No. PCT/US2016/053454 can be used. Table 8 describes exemplary anti-VEGF antibodies that can be used, as well as the amino acid sequences of the VH and VL domains for each antibody. Table 9 describes the VL HVR amino acid sequences for the anti-VEGF antibodies described in Table 8. Table 10 describes the VH HVR amino acid sequences for the anti-VEGF antibodies described in Table 8. In particular embodiments, the anti-VEGF antibody G6.31 AARR (also referred to herein as "G6.31.AARR") is used.

TABLE 8

VH and VL amino acid sequences for exemplary anti-VEGF antibodies

| Antibody Name | Variant VH (SEQ ID NO) | Variant VL (SEQ ID NO) |
|---|---|---|
| G6.31 WT | G6.31 WT (SEQ ID NO: 42) | G6.31 WT (SEQ ID NO: 38) |
| LC-N94A | G6.31 WT (SEQ ID NO: 42) | N94A (SEQ ID NO: 41) |
| LC-N94A.LC-F83A | G6.31 WT (SEQ ID NO: 42) | N94A.F83A (SEQ ID NO: 12) |
| LC-N94A.LC-F83A.HC-A40E.HC-T57E (G6.31 AAEE) | A40E.T57E (SEQ ID NO: 40) | N94A.F83A (SEQ ID NO: 12) |
| N94A.F83A.N82aR.Y58R (G6.31 AARR) | N82aR.Y58R (SEQ ID NO: 11) | N94A.F83A (SEQ ID NO: 12) |
| HCcombo | HCcombo (SEQ ID NO: 33) | G6.31 WT (SEQ ID NO: 38) |
| HCLC2 | HCcombo (SEQ ID NO: 33) | LCcombo2 (SEQ ID NO: 35) |
| HCLC4 | HCcombo (SEQ ID NO: 33) | LCcombo4 (SEQ ID NO: 37) |
| HCLC5 | HCcombo (SEQ ID NO: 33) | N94A.F83A (SEQ ID NO: 12) |
| HCLC3 | HCcombo (SEQ ID NO: 33) | LCcombo3 (SEQ ID NO: 36) |
| HCLC1 | HCcombo (SEQ ID NO: 33) | LCcombo1 (SEQ ID NO: 34) |
| R19HCcombo | R19HCcombo (SEQ ID NO: 51) | G6.31 WT (SEQ ID NO: 38) |
| R19HCLC2 | R19HCcombo (SEQ ID NO: 51) | LCcombo2 (SEQ ID NO: 35) |
| R19HCLC4 | R19HCcombo (SEQ ID NO: 51) | LCcombo4 (SEQ ID NO: 37) |
| R19HCLC5 | R19HCcombo (SEQ ID NO: 51) | N94A.F83A (SEQ ID NO: 12) |

TABLE 9

VL HVR Sequences for Antibodies from Table 8

| Antibody Name | HVR-L1 | HVR-L2 | HVR-L3 |
|---|---|---|---|
| G6.31 WT | RASQDVSTAVA (SEQ ID NO: 8) | SASFLYS (SEQ ID NO: 9) | QQGYGNPFT (SEQ ID NO: 23) |
| LC-N94A | RASQDVSTAVA (SEQ ID NO: 8) | SASFLYS (SEQ ID NO: 9) | QQGYGAPFT (SEQ ID NO: 10) |

TABLE 9-continued

VL HVR Sequences for Antibodies from Table 8

| Antibody Name | HVR-L1 | HVR-L2 | HVR-L3 |
|---|---|---|---|
| LC-N94A.LC-F83A | RASQDVSTAVA (SEQ ID NO: 8) | SASFLYS (SEQ ID NO: 9) | QQGYGAPFT (SEQ ID NO: 10) |
| LC-N94A.LC-F83A. HC-A40E.HC-T57E (G6.31 AAEE) | RASQDVSTAVA (SEQ ID NO: 8) | SASFLYS (SEQ ID NO: 9) | QQGYGAPFT (SEQ ID NO: 10) |
| N94A.F83A.N82aR.Y58R (G6.31 AARR) | RASQDVSTAVA (SEQ ID NO: 8) | SASFLYS (SEQ ID NO: 9) | QQGYGAPFT (SEQ ID NO: 10) |
| HCcombo | RASQDVSTAVA (SEQ ID NO: 8) | SASFLYS (SEQ ID NO: 9) | QQGYGNPFT (SEQ ID NO: 23) |
| HCLC2 | RASQDVSTAVA (SEQ ID NO: 8) | SASFLYS (SEQ ID NO: 9) | QQGYGAPFT (SEQ ID NO: 10) |
| HCLC4 | RASQDVSTAVA (SEQ ID NO: 8) | SASFLYS (SEQ ID NO: 9) | QQGYGAPFT (SEQ ID NO: 10) |
| HCLC5 | RASQDVSTAVA (SEQ ID NO: 8) | SASFLYS (SEQ ID NO: 9) | QQGYGAPFT (SEQ ID NO: 10) |
| HCLC3 | RASQDVSTAVA (SEQ ID NO: 8) | SASFLYS (SEQ ID NO: 9) | QQGYGAPFT (SEQ ID NO: 10) |
| HCLC1 | RASQDVSTAVA (SEQ ID NO: 8) | SASFLYS (SEQ ID NO: 9) | QQGYGAPFT (SEQ ID NO: 10) |
| R19HCcombo | RASQDVSTAVA (SEQ ID NO: 8) | SASFLYS (SEQ ID NO: 9) | QQGYGNPFT (SEQ ID NO: 23) |
| R19HCLC2 | RASQDVSTAVA (SEQ ID NO: 8) | SASFLYS (SEQ ID NO: 9) | QQGYGAPFT (SEQ ID NO: 10) |
| R19HCLC4 | RASQDVSTAVA (SEQ ID NO: 8) | SASFLYS (SEQ ID NO: 9) | QQGYGAPFT (SEQ ID NO: 10) |
| R19HCLC5 | RASQDVSTAVA (SEQ ID NO: 8) | SASFLYS (SEQ ID NO: 9) | QQGYGAPFT (SEQ ID NO: 10) |

TABLE 10

VH HVR Sequences for Antibodies from Table 8

| Antibody Name | HVR-H1 | HVR-H2 | HVR-H3 |
|---|---|---|---|
| G6.31 WT | DYWIH (SEQ ID NO: 1) | GITPAGGYTYYADSVKG (SEQ ID NO: 53) | FVFFLPYAMDY (SEQ ID NO: 3) |
| LC-N94A | DYWIH (SEQ ID NO: 1) | GITPAGGYTYYADSVKG (SEQ ID NO: 53) | FVFFLPYAMDY (SEQ ID NO: 3) |
| LC-N94A.LC-F83A | DYWIH (SEQ ID NO: 1) | GITPAGGYTYYADSVKG (SEQ ID NO: 53) | FVFFLPYAMDY (SEQ ID NO: 3) |
| LC-N94A.LC-F83A. HC-A40E.HC-T57E (G6.31 AAEE) | DYWIH (SEQ ID NO: 1) | GITPAGGYEYYADSVKG (SEQ ID NO: 21) | FVFFLPYAMDY (SEQ ID NO: 3) |
| N94A.F83A.N82aR.Y58R (G6.31 AARR) | DYWIH (SEQ ID NO: 1) | GITPAGGYTRYADSVKG (SEQ ID NO: 7) | FVFFLPYAMDY (SEQ ID NO: 3) |
| HCcombo | DYWIH (SEQ ID NO: 1) | GITPAGGYEYYADSVEG (SEQ ID NO: 22) | FVFFLPYAMDY (SEQ ID NO: 3) |
| HCLC2 | DYWIH (SEQ ID NO: 1) | GITPAGGYEYYADSVEG (SEQ ID NO: 22) | FVFFLPYAMDY (SEQ ID NO: 3) |
| HCLC4 | DYWIH (SEQ ID NO: 1) | GITPAGGYEYYADSVEG (SEQ ID NO: 22) | FVFFLPYAMDY (SEQ ID NO: 3) |

TABLE 10-continued

VH HVR Sequences for Antibodies from Table 8

| Antibody Name | HVR-H1 | HVR-H2 | HVR-H3 |
|---|---|---|---|
| HCLC5 | DYWIH (SEQ ID NO: 1) | GITPAGGYEYYADSVEG (SEQ ID NO: 22) | FVFFLPYAMDY (SEQ ID NO: 3) |
| HCLC3 | DYWIH (SEQ ID NO: 1) | GITPAGGYEYYADSVEG (SEQ ID NO: 22) | FVFFLPYAMDY (SEQ ID NO: 3) |
| HCLC1 | DYWIH (SEQ ID NO: 1) | GITPAGGYEYYADSVEG (SEQ ID NO: 22) | FVFFLPYAMDY (SEQ ID NO: 3) |
| R19HCcombo | DYWIH (SEQ ID NO: 1) | GITPAGGYEYYADSVEG (SEQ ID NO: 22) | FVFFLPYAMDY (SEQ ID NO: 3) |
| R19HCLC2 | DYWIH (SEQ ID NO: 1) | GITPAGGYEYYADSVEG (SEQ ID NO: 22) | FVFFLPYAMDY (SEQ ID NO: 3) |
| R19HCLC4 | DYWIH (SEQ ID NO: 1) | GITPAGGYEYYADSVEG (SEQ ID NO: 22) | FVFFLPYAMDY (SEQ ID NO: 3) |
| R19HCLC5 | DYWIH (SEQ ID NO: 1) | GITPAGGYEYYADSVEG (SEQ ID NO: 22) | FVFFLPYAMDY (SEQ ID NO: 3) |

The upper hinge region of the Fab heavy chain of any of the antibodies listed above, for example, G6.31 AARR, can be mutated to remove reactivity to anti-IgG1 hinge autoantibodies that has been reported in the literature. See, e.g., Brerski et al., *J. Immunol.* 181:3183-3192, 2008 and Brerski et al., *mAbs* 2:3, 212-220, 2010. Thus, the C-terminal amino acid of G6.31 AARR heavy chain can be either a T (wild-type (WT) version) or L (variant version that lacks reactivity to anti-human IgG Fab). The full-length heavy chain amino acid sequence of wild-type G6.31 AARR is SEQ ID NO: 48. The full-length heavy chain amino acid sequence of the variant version that lacks reactivity to anti-human IgG Fab is SEQ ID NO: 49. The full-length light chain amino acid sequence for both G6.31 AARR and the variant version that lacks reactivity to anti-human IgG Fab is SEQ ID NO: 50.

The amino acid sequences of the G6.31.AARR.LC-K149C cysteine engineered antibody variant light chain and heavy chain are shown below (LC-C149 is in bolded and underlined font).

```
Light chain (LC):
                                       (SEQ ID NO: 89)
DIQMTQSPSSLSASVGDRVTITCRASQDVSTAVAWYQQKPGKAPKLLIY

SASFLYSGVPSRFSGSGSGTDFTLTISSLQPEDAATYYCQQGYGAPFTF

GQGTKVEIKRTVAAPSVFIFPPSDEQLKSGTASVVCLLNNFYPREAKVQW

CVDNALQSGNSQESVTEQDSKDSTYSLSSTLTLSKADYEKHKVYACEV

THQGLSSPVTKSFNRGEC.

Heavy chain (HC):
                                       (SEQ ID NO: 90)
EVQLVESGGGLVQPGGSLRLSCAASGFTISDYWIHWVRQAPGKGLEWVA

GITPAGGYTRYADSVKGRFTISADTSKNTAYLQMRSLRAEDTAVYYCAR

FVFFLPYAMDYWGQGTLVTVSSASTKGPSVFPLAPSSKSTSGGTAALGC

LVKDYFPEPVTVSWNSGALTSGVHTFPAVLQSSGLYSLSSVVTVPSSSL

GTQTYICNVNHKPSNTKVDKKVEPKSCDKTHT.
```

The amino acid sequences of the G6.31AARR.HC-A1400 cysteine engineered antibody variant light chain and heavy chain are shown below (HC-C140 in bold underline font).

```
LC:
                                       (SEQ ID NO: 91)
DIQMTQSPSSLSASVGDRVTITCRASQDVSTAVAWYQQKPGKAPKLLIY

SASFLYSGVPSRFSGSGSGTDFTLTISSLQPEDAATYYCQQGYGAPFTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

HC:
                                       (SEQ ID NO: 92)
EVQLVESGGGLVQPGGSLRLSCAASGFTISDYWIHWVRQAPGKGLEWVA

GITPAGGYTRYADSVKGRFTISADTSKNTAYLQMRSLRAEDTAVYYCAR

FVFFLPYAMDYWGQGTLVTVSSASTKGPSVFPLAPSSKSTSGGTCALGC

LVKDYFPEPVTVSWNSGALTSGVHTFPAVLQSSGLYSLSSVVTVPSSSL

GTQTYICNVNHKPSNTKVDKKVEPKSCDKTHT.
```

The amino acid sequences of the G6.31AARR.HC-L174C cysteine engineered antibody variant light chain and heavy chain are shown below (HC-C174 in bold underline font).

```
LC:
                                       (SEQ ID NO: 93)
DIQMTQSPSSLSASVGDRVTITCRASQDVSTAVAWYQQKPGKAPKLLIY

SASFLYSGVPSRFSGSGSGTDFTLTISSLQPEDAATYYCQQGYGAPFTF

GQGTKVEIKRTVAAPSVFIFPPSDEQLKSGTASVVCLLNNFYPREAKVQ

WKVDNALQSGNSQESVTEQDSKDSTYSLSSTLTLSKADYEKHKVYACEV

THQGLSSPVTKSFNRGEC.

HC:
                                       (SEQ ID NO: 94)
EVQLVESGGGLVQPGGSLRLSCAASGFTISDYWIHWVRQAPGKGLEWVA

GITPAGGYTRYADSVKGRFTISADTSKNTAYLQMRSLRAEDTAVYYCAR

FVFFLPYAMDYWGQGTLVTVSSASTKGPSVFPLAPSSKSTSGGTAALGC
```

-continued

LVKDYFPEPVTVSWNSGALTSGVHTFPAVCQSSGLYSLSSVVTVPSSSL

GTQTYICNVNHKPSNTKVDKKVEPKSCDKTHT.

Example 4: HA-G6.31.AARR Conjugates Produced from Monodisperse HA Show Improved Physical Stability Under Physiological Stress Relative to HA-G6.31.AARR Conjugates Produced from Polydisperse HA (A) Materials and Methods Monodisperse HA synthesized by chemoenzymatic means using the *Pasteurella multocida* hyaluronan synthase (PmHAS) was from Hyalose (Oklahoma City, OK). All other chemicals and reagents were from Sigma Aldrich (St. Louis, MO).

Monodisperse HA (monoHA, Mw 137 kDa, RH 21.2 nm) was modified with N-(2-aminoethylmaleimide) as previously described to contain 4.0% maleimide groups. G6.31.AARR.Fab-C was then conjugated to the monoHA-maleimide backbone as previously described and purified by SEC on a HILOAD® SUPERDEX® 200 µg column with PBS pH 7.4 running buffer. The conjugate fractions were pooled and confirmed by SEC-RI-MALS.

Purified monoHA-G6.31.AARR was concentrated by ultrafiltration to 5 mg/mL (on a Fab basis) in PBS, spiked with sodium azide and polysorbate 20 (PS20) to final concentrations of 2 mM and 0.01%, respectively, and incubated at 37° C. At sampling time points, samples were withdrawn and diluted to 1 mg/mL in a buffer containing 10 mM His-HCl (pH 5.5), 150 mM NaCl, 10% (w/v) trehalose, and 0.01% polysorbate 20, and then assayed for soluble protein concentration ($A_{280}$), turbidity ($A_{450}$), SEC retention time, and molecular weight (Mn and Mw by SEC-RI-MALS).

(B) Results

HA-G6.31.AARR conjugates produced using monodisperse HA showed vastly improved physical stability out to four weeks as compared to HA-G6.31.AARR conjugates produced with similar sized polydisperse HA at the same Fab loading level (FIG. 14). The molecular weight (Mw) of monoHA-G6.31.AARR decreased slightly from week 0 to week 2 and week 4, but this loss could be entirely accounted for by loss in free Fab due to reverse-Michael deconjugation, as commonly observed for thiol-maleimide conjugated proteins. There was also no discernable shift in SEC retention time for monoHA-G6.31.AARR, indicating that the physical size of the conjugate was not changing over time.

These results clearly support the hypothesis that, within a population of HA-G6.31.AARR conjugates produced from a polydisperse HA starting material, the high molecular weight HA-based subpopulation is responsible for the physical instability observed after physiological stress. Removing this subpopulation by homogenizing the HA starting material (i.e., starting from a monodisperse HA) results in a more stable conjugate molecule that is less prone to precipitation under physiological stress conditions. These data further support using HA-G6.31.AARR conjugates produced from a monodisperse HA material as therapeutic agents for in vivo use.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. A method of treating an ocular disorder, the method comprising administering an effective amount of an antibody conjugate comprising (i) an antibody that specifically binds to vascular endothelial growth factor (VEGF) and (ii) a hyaluronic acid (HA) polymer covalently attached to the antibody, wherein the HA polymer has a polydispersity index (PDI) of between 1.0 and 1.1, or a pharmaceutical composition thereof to a subject in need of such treatment.

2. The method of claim 1, wherein the ocular disorder is age-related macular degeneration (AMD), diabetic macular edema (DME), diabetic retinopathy (DR), or retinal vein occlusion (RVO).

3. The method of claim 1, further comprising administering to the subject an effective amount of a second agent, wherein the second agent is selected from the group consisting of an antibody, an anti-angiogenic agent, a cytokine, a cytokine antagonist, a corticosteroid, an analgesic, and a compound that binds to a second biological molecule.

4. The method of claim 1, wherein the antibody conjugate or the pharmaceutical composition is administered intravitreally, ocularly, intraocularly, juxtasclerally, subtenonly, superchoroidally, topically, intravenously, intramuscularly, intradermally, percutaneously, intraarterially, intraperitoneally, intralesionally, intracranially, intraarticularly, intraprostatically, intrapleurally, intratracheally, intrathecally, intranasally, intravaginally, intrarectally, topically, intratumorally, intraperitoneally, peritoneally, intraventricularly, subcutaneously, subconjunctivally, intravesicularly, mucosally, intrapericardially, intraumbilically, intraorbitally, orally, transdermally, by inhalation, by injection, by eye drop, by implantation, by infusion, by continuous infusion, by localized perfusion bathing target cells directly, by catheter, by lavage, in cremes, or in lipid compositions.

5. The method of claim 1, wherein the HA polymer has a PDI between 1.0 to about 1.07.

6. The method of claim 5, wherein the HA polymer has a PDI of about 1.05.

7. The method of claim 1, wherein:
the HA polymer has a molecular weight between about 100 kDa and about 250 kDa;
(ii) the HA polymer is a linear HA polymer;
(iii) the antibody conjugate has a hydrodynamic radius between about 10 nm and about 60 nm; and/or
(iv) the antibody conjugate has an ocular half-life that is increased relative to a reference antibody that is not covalently attached to the HA polymer.

8. The method of claim 1, wherein the antibody specifically binds to a biological molecule selected from the group consisting of vascular endothelial growth factor (VEGF); IL-1β; IL-6; IL-6R; IL-13; IL-13R; PDGF; angiopoietin; angiopoietin 2; Tie2; S1P; integrins αvβ3, αvβ5, and α5β1; betacellulin; apelin/APJ; erythropoietin; complement factor D; TNFα; HtrA1; a VEGF receptor; ST-2 receptor; and a protein genetically linked to AMD risk.

9. The method of claim 8, wherein the antibody comprises the following six HVRs:
(a) an HVR-H1 comprising the amino acid sequence of DYWIH (SEQ ID NO: 1);
(b) an HVR-H2 comprising the amino acid sequence of GITPAGGYTRYADSVKG (SEQ ID NO: 7);
(c) an HVR-H3 comprising the amino acid sequence of FVFFLPYAMDY (SEQ ID NO: 3);
(d) an HVR-L1 comprising the amino acid sequence of RASQDVSTAVA (SEQ ID NO: 8);
(e) an HVR-L2 comprising the amino acid sequence of SASFLYS (SEQ ID NO: 9); and
(f) an HVR-L3 comprising the amino acid sequence of QQGYGAPFT (SEQ ID NO: 10).

10. The method of claim 8, wherein the antibody comprises (a) a VH domain comprising the amino acid sequence of SEQ ID NO: 11; (b) a VL domain comprising the amino acid sequence of SEQ ID NO: 12; or (c) a VH domain as in (a) and a VL domain as in (b).

11. The method of claim 10, wherein the antibody comprises (a) a VH domain comprising the amino acid sequence of SEQ ID NO: 11 and (b) a VL domain comprising the amino acid sequence of SEQ ID NO: 12.

12. The method of claim 8, wherein the antibody comprises:
(a) a heavy chain comprising the amino acid sequence of SEQ ID NO: 48 and a light chain comprising the amino acid sequence of SEQ ID NO: 50; or
(b) a heavy chain comprising the amino acid sequence of SEQ ID NO: 49 and a light chain comprising the amino acid sequence of SEQ ID NO: 50.

13. The method of claim 8, wherein:
(i) the antibody is capable of inhibiting the binding of VEGF to a VEGF receptor;
(ii) the antibody binds human VEGF (hVEGF) with a Kd of about 2 nM or lower;
(iii) the antibody has a melting temperature (Tm) of greater than about 83.5° C.; and/or
(iv) the antibody has an isoelectric point (pI) of lower than 8.

14. The method of claim 1, wherein:
(i) the antibody is monoclonal, human, humanized, or chimeric;
(ii) the antibody is an antigen-binding antibody fragment;
(iii) the antibody is a monospecific antibody; and/or
(iv) the antibody is a cysteine-engineered antibody.

15. The method of claim 14, wherein the antibody fragment is selected from the group consisting of Fab, Fab-C, Fab'-SH, Fv, scFv, and (Fab')$_2$ fragments.

16. A method for treating an ocular disorder, the method comprising administering an effective amount of a pharmaceutical composition to a subject in need of such treatment, wherein the pharmaceutical composition comprises an antibody conjugate comprising (i) an antibody that specifically binds VEGF and (ii) an HA polymer covalently attached to the antibody, wherein the HA polymer has a PDI of 1.05, and wherein the antibody comprises (a) a VH domain comprising the amino acid sequence of SEQ ID NO: 11 and (b) a VL domain comprising the amino acid sequence of SEQ ID NO: 12.

17. The method of claim 16, wherein the ocular disorder is AMD, DME, DR, or RVO.

18. A method for treating an ocular disorder, the method comprising administering an effective amount of a pharmaceutical composition to a subject in need of such treatment, wherein the pharmaceutical composition comprises an antibody conjugate comprising (i) an antibody that specifically binds VEGF and (ii) an HA polymer covalently attached to the antibody, wherein the HA polymer has a PDI of 1.05, and wherein the antibody comprises (a) a heavy chain comprising the amino acid sequence of SEQ ID NO: 48 or SEQ ID NO: 49 and (b) a light chain comprising the amino acid sequence of SEQ ID NO: 50.

19. The method of claim 18, wherein the ocular disorder is AMD, DME, DR, or RVO.

20. The method of claim 1, wherein the HA polymer has a PDI between about 1.0001 and about 1.06.

21. The method of claim 7, wherein the HA polymer has a molecular weight between about 100 kDa and about 250 kDa.

22. The method of claim 21, wherein the HA polymer has a molecular weight between about 150 kDa and about 200 kDa.

* * * * *